(12) United States Patent
Akerley et al.

(10) Patent No.: US 7,838,502 B2
(45) Date of Patent: Nov. 23, 2010

(54) **COMPOSITIONS AND METHODS TO MODULATE *H. INFLUENZAE* PATHOGENESIS**

(75) Inventors: Brian J. Akerley, Millbury, MA (US); Sandy M. Wong, Millbury, MA (US)

(73) Assignee: University of Massachusetts Medical School, Shrewsbury, MA (US)

( * ) Notice: Subject to any disclaimer, the term of this patent is extended or adjusted under 35 U.S.C. 154(b) by 349 days.

(21) Appl. No.: 11/123,761

(22) Filed: May 6, 2005

(65) Prior Publication Data

US 2006/0252719 A1 Nov. 9, 2006

(51) Int. Cl.
*A01N 43/04* (2006.01)
(52) U.S. Cl. .................................................. 514/44 A
(58) Field of Classification Search ............... 435/252.1
See application file for complete search history.

(56) References Cited

U.S. PATENT DOCUMENTS

| | | | | |
|---|---|---|---|---|
| 5,034,506 | A | 7/1991 | Summerton et al. ......... | 528/391 |
| 5,684,144 | A * | 11/1997 | Romeo ....................... | 536/23.7 |
| 6,096,720 | A | 8/2000 | Love et al. ................... | 514/44 |
| 6,335,185 | B1 | 1/2002 | Rancourt et al. ........... | 435/91.4 |
| 6,537,815 | B2 | 3/2003 | Romeo ....................... | 435/471 |
| 6,783,930 | B1 | 8/2004 | Pelletier et al. ............. | 435/5 |
| 2003/0216346 | A1 | 11/2003 | Sakuri et al. ................ | 514/44 |
| 2003/0224377 | A1 | 12/2003 | Wengel et al. .............. | 435/6 |
| 2003/0235577 | A1 | 12/2003 | Shapiro et al. ........... | 424/94.65 |
| 2004/0052840 | A1 | 3/2004 | Kubota et al. ............... | 424/468 |
| 2004/0219585 | A1 | 11/2004 | Bakaletz et al. ............. | 435/6 |
| 2004/0266004 | A1 | 12/2004 | Terada et al. ................ | 435/455 |

FOREIGN PATENT DOCUMENTS

| | | |
|---|---|---|
| EP | 0 431 523 A2 | 6/1991 |
| WO | WO 95/24929 | 9/1995 |
| WO | WO 99/14226 | 3/1999 |
| WO | WO 00/56746 | 9/2000 |
| WO | WO 00/66604 | 11/2000 |
| WO | WO02077183 A2 * | 10/2002 |

OTHER PUBLICATIONS

Akerley et al. "A genomescale analysis for identification of genes required for growth or survival of *Haemophilus influenzae*," *Proc Natl Acad Sci USA* 99:966-971 (2002).
Barcak et al., "Genetic systems in *Haemophilus influenzae*," *Methods Enzymol* 204:321-342 (1991).
Begley et al. "Thiamin biosynthesis in prokaryotes" *Arch Microbiol* 171:293-300 (1999).
Bouchet et al., "Host-derived sialic acid is incorporated into *Haemophilus influenzae* lipopolysaccharide and is a major virulence factor in experimental otitis media," *Proc Natl Acad Sci USA* 100:8898-8903 (2003).
Campagnari et al., "Lipooligosaccharide epitopes shared among gram-negative non-enteric mucosal pathogens," *Microb Pathog* 8:353-362 (1990).

Chatterjee et al., "Inactivation of rsmA leads to overproduction of extracellular pectinases, cellulases, and proteases in *Erwinia carotovora* subsp. *carotovora* in the absence of the starvation/cell density-sensing signal, N-(3-oxohexanoyl)-L-homoserine lactone," *Appl Environ Microbiol* 61:1959-1967 (1995).
Choe et al.,"Identification of the regulatory sequence of anaerobically expressed locus *aeg-46.5*," *J Bacteriol* 175:1165-1172 (1993).
Compan et al., "Interaction of six global transcription regulators in expression of manganese superoxide dismutase in *Escherichia coli* K-12," *J Bacteriol* 175:1687-1696 (1993).
Conley et al., "Lack of IgA subclass restriction in antibody response to phosphorylcholine, beta lactoglobulin and tetanus toxoid," *Immunology* 53:419-426 (1984).
Costerton et al., "Bacterial biofilms: a common cause of persistent infections," *Science* 284:1318-1322 (1999).
Cotter et al., "Oxygen, nitrate, and molybdenum regulation of *dmsABC* gene expression in *Escherichia coli*," *J Bacteriol* 171:3817-3823 (1989).
Cox et al.,"Structural analysis of the lipopolysaccharide from the nontypable *Haemophilus influenzae* strain SB 33," *Eur J Biochem* 268:5278-5286 (2001).
Cui et al., "Identification of a global repressor gene, *rsmA*, of *Erwinia carotovora* subsp. *carotovora* that controls extracellular enzymes, N-(3-oxohexanoyl)-L-homoserine lactone, and pathogenicity in soft-rotting *Erwinia* spp.," *J Bacteriol* 177:5108-5115 (1995).
Cunningham et al., "Co-regulation of lipoamide dehydrogenase and 2-oxoglutarate dehydrogenase synthesis in *Escherichia coli*: characterisation of an ArcA binding site in the *lpd* promoter," *FEMS Microbiol Lett* 169:403-408 (1998).
Donlan et al., "Biofilms: survival mechanisms of clinically relevant microorganisms," *Clin Microbiol. Rev* 15(2):167-193 (2002).
D'Mello et al., "Role of bacterial Mn-cofactored superoxide dismutase in oxidative stress responses, nasopharyngeal colonization, and sustained bacteremia caused by *Haemophilus influenzae* type b," *Infect Immun* 65:2700-2706 (1997).
Dunne W., "Bacterial adhesion: seen any good biofilms lately?," *Clin Microbiol Rev* 15(2):155-166 (2002).
Ehrlich et al., "Mucosal biofilm formation on middle-ear mucosa in the chinchilla model of otitis media," *JAMA* 287:1710-1715 (2002).
Esposito et al., "The complete nucleotide sequence of bacteriophage HP1 DNA," *Nucleic Acids Research* 24:2360-2368 (1996).

(Continued)

*Primary Examiner*—Mark Navarro
(74) *Attorney, Agent, or Firm*—Medlen & Carroll, LLP

(57) ABSTRACT

The present invention discloses novel signaling pathways controlling the pathogenesis of the human respiratory bacterium, *Haemophilus influenzae*. The lipooligosaccharide-phosphorylycholine (LOS-PC) cell surface epitope of *H. influenzae* enhances pathogenesis but also increases bacterial susceptibility to innate and adaptive immunity and the administration of therapeutic compounds. Modulation of the LOS-PC epitope may be affected by an interaction between environmental conditions (i.e., for example, oxygen tension) and genetic regulation of precursor biosynthetic pathway activity. LOS-PC epitope display increases under microaerobic conditions and decreases under aerobic conditions. This is consisent with a bacteria's propensity to initiate pathogensis under low oxygen conditions. Pathogenesis may be prevented by disrupting the role of the putative *H. influenzae* homologue of CsrA, that downregulates galU expression. Disrupting CsrA repression of galU expression resulted in increased LOS-PC epitope display.

5 Claims, 18 Drawing Sheets

OTHER PUBLICATIONS

Evans et al.,"Haemin and nicotinamide adenine dinucleotide requirements of *Haemophilus influenzae* and *Haemophilus parainfluenzae*," *J Med Microbiol* 7:359-365 (1974).

Fleischmann et al., "Whole-genome random sequencing and assembly of *Haemophilus influenzae* Rd.," *Science* 269: 496-512 (1995).

Folkerts et al., "Induction of guinea pig respiratory airway hyperreactivity by *Haemophilus influenzae*: role of histaminergic and cholinergic receptor systems," *Agents Actions* 17:399-400 (1986).

Gregoriadis G., "Liposomes for drugs and vaccines" *Trends in Biotechnology* 3:235-241 (1985).

Greiner et al., "Nontypeable *Haemophilus influenzae* strain 2019 produces a biofilm,containing *N*-acetylneuraminic acid that may mimic sialylated O-linked glycans," *Infect Immun* 72: 4249-4260 (2004).

Harada et al., "Adherence of *Haemophilus influenzae* to nasal, nasopharyngeal and buccal epithelial cells from patients with otitis media," *Eur Arch Oto-Rhino-Laryng*, 247:122-124 (1990).

Heeb et al., "Regulatory RNA as mediator in GacA/RsmA-dependent global control of exoproduct formation in *Pseudomonas fluorescens* CHA0," *J Bacteriol* 184:1046-1056 (2002).

Herbert et al., "Aerobic growth deficient *Haemophilus influenzae* mutants are non-virulent: implications on metabolism," *Int J Med Microbiol* 293:145-152 (2003).

Herbert et al., "Signature Tagged Mutagenesis of *Haemophilus influenzae* identifies genes required for in vivo survival," *Microb Pathog* 33:211-223 (2002).

Hood et al., "Use of the complete genome sequence information of *Haemophilus influenzae* strain Rd to investigate lipopolysaccharide biosynthesis," *Mol Microbiol* 22:951-965 (1996a).

Hood et al., "DNA repeats identify novel virulence genes in *Haemophilus influenzae*," *Proc Natl Acad Sci USA* 93:11121-11125 (1996b).

Hood et al., "Sialic acid in the lipopolysaccharide of *Haemophilus influenzae*: strain distribution, influence on serum resistance and structural characterization," *Mol Microbiol* 33: 679-692 (1999).

Ji et al., "Regulated antisense rna eliminates alpha-toxin virulence in *Staphylococcus aureus* infection," *J Bacteriol* 18(21):6585-6590 (1999).

Ji et al., "Identification of critical staphylococcal genes using conditional phenotypes generated by antisense RNA," *Science* 293:2266-2269 (2001).

Kernodle et al., "Expression of antisense *hla* fragment in *Staphylococcus aureus* reduces alpha-toxin production in vitro and attenuates lethal activity in a murine model," *Infect Immun* 65:179-184 (1997).

Lawhon et al., "Global regulation by CsrA in *Salmonella typhimurium*," *Mol Microbiol* 48:1633-1645 (2003).

Leon et al., "Specificity for phosphorylcholine of six murine myeloma proteins reactive with *Pneumococcus* C polysaccharide and beta-lipoprotein," *Biochem* 10:1424-1429 (1971).

Lynch et al., "Transcriptional control mediated by the ArcA two-component response regulator protein of *Escherichia coli*: characterization of DNA binding at target promoters," *J Bacteriol* 178:6238-6249 (1996).

Ma et al., "Molecular characterization of global regulatory RNA species that control pathogenicity factors in *Erwinia amylovora* and *Erwinia herbicola* pv. *gypsophilae*," *J Bacteriol* 183:1870-1880 (2001).

Macfadyen et al.,"Life in mucus: sugar metabolism in *Haemophilus influenzae*," *Res Microbiol* 147:541-551 (1996).

Mansson et al., "Structural analysis of the lipopolysaccharide from nontypeable *Haemophilus influenzae* strain 1003," *Eur J Biochem* 269:808-818 (2002).

Mansson et al.,"Structural diversity in lipopolysaccharide expression in nontypeable *Haemophilus influenzae*. Identification of L-*glycero*-D-*manno*-heptose in the outer-core region in three clinical isolates," *Eur J Biochem* 270:610-624 (2003).

Marra et al., "*Streptococcus pneumoniae* causes experimental meningitis following intranasal and otitis media infections via a nonhematogenous route," *Infect Immun* 69:7318-7325 (2001).

Mizu et al., "Antisense oligonucleotides bound in the polysaccharide complex and the enhanced antisense effect due to the low hydrolysis," *Biomaterials* 25:3117-3123 (2004).

Murphy et al.,"Biofilm formation by nontypeable *Haemophilus influenzae*: strain variability, outer membrane antigen expression and role of pili," *BMC Microbiol* 2:7 (2002).

Nakamura et al., "Evidence of antisense tumor targeting in mice," *Bioconjug Chem.* 15:1475-80 (2004).

Nesper et al., "Characterization of *Vibrio cholerae* O1 El tor *galU* and *galE* mutants: influence on lipopolysaccharide structure, colonization, and biofilm formation," *Infect Immun* 69:435-445 (2001).

Nielsen et al., "Sequence-Selective Recognition of DNA by Strand Displacement with a Thymine-Substituted Polyamide" *Science* 254:1497 (1991).

Nizet et al., "A virulent nonencapsulated *Haemophilus influenzae*." *J Infect Dis* 173:180-186 (1996) {Erratum, 178:296 1998}.

Pessi et al.,"The global posttranscriptional regulator RsmA modulates production of virulence determinants and *N*-acylhomoserine lactones in *Pseudomonas aeruginosa*," *J Bacteriol* 183: 6676-6683 (2001).

Palacios et al., "Role of p38 mitogen-activated protein kinase in middle ear mucosa hyperplasia during bacterial otitis media," *Infect Immun* 72:4662-4667 (2004).

Rioux et al.,"Isolation and characterization of mini-Tn*10* lipopolysaccharide mutants of *Actinobacillus pleuropneumoniae* serotype 1," *Can J Microbiol* 45:1017-1026 (1999).

Risberg et al.,"Structural analysis of the lipopolysaccharide oligosaccharide epitopes expressed by a capsule-deficient strain of *Haemophilus influenzae* Rd," *Eur J Biochem* 261:171-180 (1999).

Romeo et al., "Identification and molecular characterization of *csrA*, a pleiotropic gene from *Escherichia coli* that affects glycogen biosynthesis, gluconeogenesis, cell size, and surface properties," *J Bacteriol* 175:4744-4755 (1993).

Romeo, T., "Global regulation by the small RNA-binding protein CsrA and the non-coding RNA molecule CsrB," *Mol Microbiol* 29:1321-1330 (1998).

Sabnis et al., "Pleiotropic regulation of central carbohydrate metabolism in *Escherichia coli* via the gene *csrA*," *J Biol Chem* 270:29096-29104 (1995).

Schneerson et al., "Age-related susceptibility to *Haemophilus influenzae* type b disease in rabbits," *Infect Immun* 4:397-401 (1971).

Schweda et al.,"Characterization of the phosphocholine-substituted oligosaccharide in lipopolysaccharides of type b *Haemophilus influenzae*," *Eur J Biochem* 267:3902-3913 (2000).

Shao et al., "Overexpression and biochemical characterization of beta-1,3-*N*-acetylgalactosaminyltransferase LgtD from *Haemophilus influenzae* strain Rd," *Biochem Biophys Res Commun* 295:1-8 (2002).

Sharetzsky et al., "A novel approach to insertional mutagenesis of *Haemophilus influenzae*," *J Bacteriol* 173:1561-1564 (1991).

Shaw et al., "Natural antibodies with the T15 idiotype may act in atherosclerosis, apoptotic clearance, and protective immunity," *J Clin Invest* 105:1731-1740 (2000).

Skowronek et al., "Comparison of HP1c1 and S2 phages of *Haemophilus influenzae*," *Acta Microbiol. Pol.* 35:227-232 (1986).

Smith et al., "Frequency and distribution of DNA uptake signal sequences in the *Haemophilus influenzae* rd genome," *Science* 269:538-540 (1995).

Smith et al., "DNA uptake signal sequences in naturally transformable bacteria," *Res Microbiol* 150:603-616 (1999).

Stenfors et al., "Abundant attachment of bacteria to nasopharyngeal epithelium in otitis-prone children", *J Infect Dis* 165:1148-1150 (1992).

Stephens et al., "Pathogenic events during infection of the human nasopharynx with *Neisseria meningitidis* and *Haemophilus influenzae*," *Rev Infect Dis*, 13:22-23 (1991).

Sundararajan et al., "Biochemical observations on *E. coli* mutants defective in uridine diphosphoglucose," *Proc Natl Acad Sci USA* 48:2187-2193 (1962).

Swords et al., "Non-typeable *Haemophilus influenzae* adhere to and invade human bronchial epithelial cells via an interaction of lipooligosaccharide with the PAF receptor," *Mol Microbiol* 37:13-27 (2000).

Valverde et al., "RsmY, a small regulatory RNA, is required in concert with RsmZ for GacA-dependent expression of biocontrol traits in *Pseudomonas fluorescens* CHA0," *Mol Microbiol* 50:1361-1379 (2003).

Vander Horn et al.,"Structural genes for thiamine biosynthetic enzymes (*thiCEFGH*) in *Escherichia coli* K-12," *J Bacteriol* 175:982-992 (1993).

Weilbacher et al., "A novel sRNA component of the carbon storage regulatory system of *Escherichia coli*," *Mol Microbiol* 48: 657-670 (2003).

Weiser et al., "The molecular mechanism of phase variation of *H. influenzae* lipopolysaccharide," *Cell* 59:657-665 (1989).

Weiser et al.,"Decoration of lipopolysaccharide with phosphorylcholine: a phase-variable characteristic of *Haemophilus influenzae*," *Infect Immun* 65:943-950 (1997).

Weiser et al., "Phosphorylcholine on the lipopolysaccharide of *Haemophilus influenzae* contributes to persistence in the respiratory tract and sensitivity to serum killing mediated by C-reactive protein," *J Exp Med* 187:631-640 (1998).

Weissborn et al.,"UTP: alpha-D-glucose-1-phosphate uridylyltransferase of *Escherichia coli*: isolation and DNA sequence of the *galU* gene and purification of the enzyme," *J Bacteriol* 176:2611-2618 (1994).

White et al., "Hemin Biosynthesis in *Haemophilus*," *J Bacteriol* 85:842-850 (1963).

Williams et al.,"Bacteriophage HP2 of *Haemophilus influenzae*," *J Bacteriol* 184:6893-6905 (2002).

Wong et al.,"Inducible expression system and marker-linked mutagenesis approach for functional genomics of *Haemophilus influenzae*," *Gene* 316:177-186 (2003).

Yang et al.,"Coordinate genetic regulation of glycogen catabolism and biosynthesis in *Escherichia coli* via the CsrA gene product," *J Bacteriol* 178:1012-1017 (1996).

Walker et al.,"Biotinylation facilitates the uptake of large peptides by *Escherichia coli* and other gram-negative bacteria," *App. Envir. Microbiol*. 71:1850-1855 (2005).

\* cited by examiner

A.
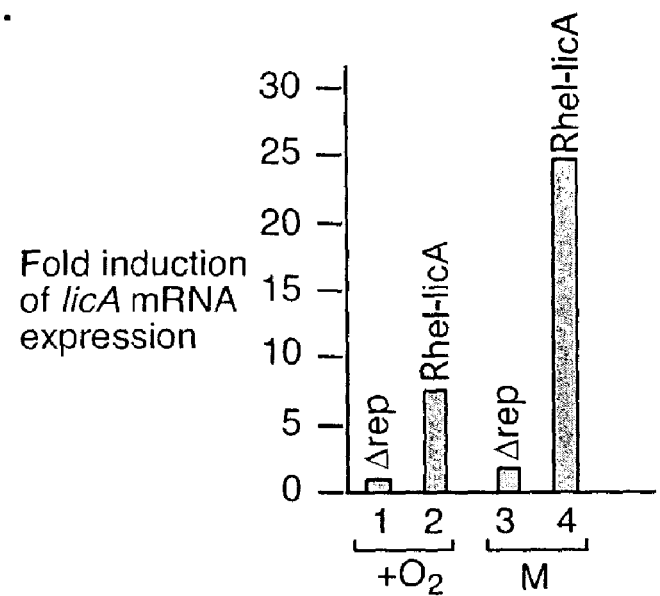
B.
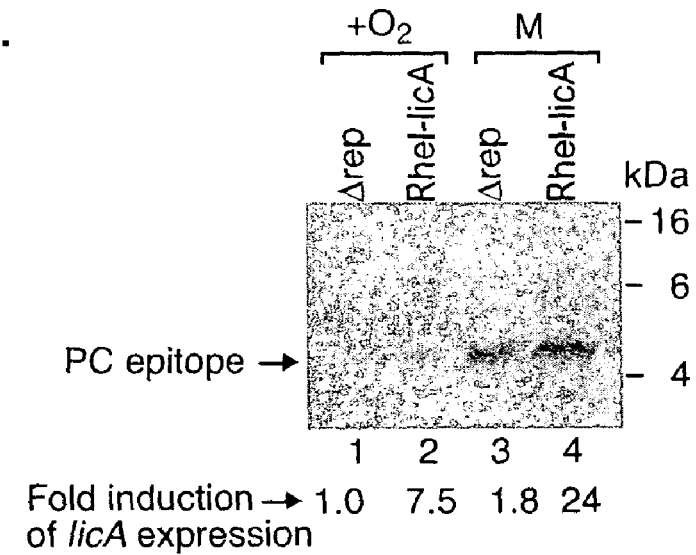
Figure 4

A

H. influenzae Rd KW20 csrA:
ATGTTAATCTTAACTCGTAAAGTTGGCGAAAGTGTACTTATTGGAGATGA
TATTTCTATCACGGTTTTGAGTGTACGTGGAAACCAAGTTAAACTCGGTG
TTGAAGCGCCTAAAGAAGTATCCGTTCACCGAGAAGAAATTTACCAACGA
ATTAAACAAACGAAAGATGAACCCTATTTAGGTTCCTCTTAG

B

H. influenzae Rd KW20 CsrA (64 amino acids predicted):
MLILTRKVGESVLIGDDISITVLSVRGNQVKLGVEAPKEVSVHREEIYQR
IKQTKDEPYLGSS

Figure 8

ACTAGTTATTGCTCCAGTTGTTAGTTTTCACACTTTAAAAAAGGCTTTCAATTATAAAATCT
TTCTCCATTATTACGTTTTTTCACAACTGTGATCCACGCCACAGTTGCAAATAATCAACATA
GAAAAATTAAATAACATAATTGATGAAAAGTTAGTTTTTCACAAAAATACGAAAAATTTCA
TCACCTAGAGAGGAATTCCATATGG<u>G</u>AAGAGCGGCGCGCC<u>GCTCTTC</u>GTAA<u>GGATCC</u>
            not in xylA       SapI               SapI          BamHI

Figure 9

```
   1 cttcctcccc cgccgaattt acgttaaaaa tttgtgtttt ttcagttaga tttcaaaata
  61 aaaattaatc taacttattg aagtaaaaga gatcattaat gcaactgaat agagaactta
 121 actgtaaaaa tttcaatctt tttcatcatt tttcacttaa aatagatcat tgataataag
 181 aataacaaga taacctaatg attttaaat tgttttaaa ttttccgtgt gaaatatgag
 241 agtaattgat ttcagttaat tgactggcgg ttatcgccat tgtttaaaga taggtttaaa
 301 agtaaagata aaaactagat attataacc gccactttgt cgccagttga atattattgg
 361 tgggtcgtga aggattcgaa ccttcgacca acggattaaa agtccgctgc tctaccgact
 421 gagctaacga cccaattaga tgattttaaa gtaaattta aatctttgg attggtgttt
 481 aaatggtgcc cgaagccaga cttgaactgg cacgcctcga aaggcgaggg attttaaata
 541 ccatagttaa accagtataa acaataactt atagcaacat taattgcttg ctcgtgcaaa
 601 taagggcata taaggtaaa tataagacag aaccgccagc caatcgccag taaaatagag
 661 gaaaaagtac aagggatttt ttgaaaaaca atcccttttt actgtgcagg attagaaagc
 721 gggttgaatt tgaccgcact ttctaagtgc gaaggggcga agtgcgcata acgcatcgtc
 781 atttcgatag ttgaatgacc gaggatttct ttcaacacta aaatattccc accgttcatc
 841 ataaaatggc tggcgaacgt atggcgcaaa acgtgggtta gttgcccttt gggtaactca
 901 atttcagcac gcaaaacagc attttcaaag gattcgtaag catcattgaa taatctgcca
 961 cgctttttcg gtagcatatc gaacaattct ttactgatcg gcacggtcct attttcttt
1021 gatttcgtat tcacgaacgt gattttatac ggcataactt gtgattgggt cagtgtttcc
1081 gcctcactcc aacgtgcacc agttgccaaa caaattcgta caatcaagcc caaatcaggg
1141 ttgcgggagt tatcgcactc agctaataaa cggtaaatat cccgctcata taaaaacgct
1201 agttctgttt ctcgttcttt aaataagcgc acaccgtcaa ggggattttc agctgtccac
1261 tttcgcaatg atttcagttc gttaaacacc gcccgcaaat aagcgtgttc acggtttact
1321 gtggcttctt tcgggggatt gtttttattt accgaaaatt ccccatcaag gcggcgtttg
1381 cggtagtcgg caaagatttc agcgttaaat tcattggcag gcggatcgcc caagttcgcg
1441 cacaagttct ttagtttggc taaacgtgcc tcaccgtctg acaacgtttt accgtgcaaa
1501 tcaaaccatt cctgcacata aaaacttaat gcgggcaagt cgcttgattc caaaacttgt
1561 acggaatcaa ccgcacttgt cgtttgttct tggcttgat tgtaaaaacg tagcgcatcg
1621 cctttggtta aaaaccattt gcgtaaccgc ttccgtttta cataaacttc cgcaagccat
1681 ttaccgtttt ttgtgtcttt gcgaactgcc attactcaac ttcaggaaat ttaggtaaag
1741 atttaaacca ctctttacca tatttatcaa taagtgtttt catgtgggcg tcaagatcat
1801 ttgattcttt acttttagtc ttagggtaaa attttgattt ctttatatta tccatattgc
1861 agttttttac atcatttca caaactttat taagaacatc atcgggaaaa tcagttgcta
1921 tgagcgacag catacccctcc atttgtgatt ggggtttata atcctggcta tctgccttta
1981 acaaattttc ttttatggga tttaagattt tatctaagaa ttgttcggta aatatgcatt
2041 gattaaaact aagcgaatct aaagaaaact catcacacct acacatcaaa tcaacagtat
2101 cgttctttga taattctaaa attttaggat ctttctcatt gactttaaaa tgagcacttc
2161 caatcattga attttttatt tttgatatga taaaggcgtt gccaaaagca tcttctttaa
2221 tctgattaat ggttgttttt attctcaaat tttatctttt atattttta ttagctgcca
2281 attcattatt tgtatagtct gaataaattt catctaccga taaaacattg ccagaaacat
2341 ggcttttatt actcttcaat acataattct taaaatattc aagagaattg ctaataaaaa
2401 gttctttaga atggctgaac gctaatatag agttggaaga aatgaggatt aaaacaagca
2461 aaaatattt acgcatatta tttacctatc ttctacaaat ctgtttagaa cgagaaaaccg
2521 atccatcatt acaaataaac ttgccaccgg aacaatgcga aacgccgcct ttttacctg
2581 agcaaggctc acgcccacgc gcatctgcca tattggcaac cataaagaat gagcttgcaa
2641 ttaaaactgt tgaaattaat tttttcatta catttctcc attttaagaa tcaccttccc
2701 caccacatca atatcactca attcacattc aaaactgaat ttgccaccgt ccacacggat
2761 ttttcctgca ggtaacacag tgatataacg gataagatgg gagttttcga cgatgacgaa
2821 gtattcgcca tccactaaat tgccgtaatc gctagtggca aagtaggtgc gattgtcttc
2881 atcaatacga aacacttgt cataactttc acggctgtc aaattcgta agtaaggcaa
2941 aagaaagggt ttattttcca ttatgaaaga ttttccgctt tctagtttta ttgcatgaaa
3001 atatttcagg tagtctgaat tatcgaaaat cggctcattt ccataggcca cataatccaa
3061 tcttgcgccc gtttcttttca cgcaacggat cactaattct gcaggaaaaa aaccacgttt
3121 agcccaagtg ccaaaggtac tgtgaggcat tccaagatgt tcagctaata atttctatt
3181 cgcaaaacca tacgcttcca ttatgcgaga ataacatcc ttgccaccga taaattcttt
3241 catttagcaa attgacctta atattttat tgacagggtc aaatgacccg aagtatattt
3301 aaggggtcaa atgacccaaa ggtaatatat accattattt acagatggag gagtttaagc
3361 aatgaacggc caaatgcaa tttgtataaa tgtacagatc cacgcgcctt acgtcacgtt
3421 gaagaaatat gctgagctta ctgggctttc gttagacaaa gtgcgaaaga tgagagcggc
3481 aggcgaactg cctattgcag ataaaaagc ggaaagaggt tcagtgttag tgaatttaat
3541 cgcgattgcc aaacaggcgg caaaacaaga ataaaaacc acacaaagt gcggtcacaa
3601 aaaacaaggt ttttgaacg ttggctatgc caacggctgc gaagcagcga acaatcctta
3661 caaggattgt gagtaatttc caaaagattt tagttataag gggaagacaa tgactaaatc
3721 atcattcacg ttttctttc aagaattcg aagaaaaca aatttaacca acgaagaaat
3781 tcaagaaaga ttcgctattc ttcagtatca ggcagaagtc gagcgagata ccactcaaga
3841 tcatcagcag ctttcggcga ttttgcgaa atggcgtgaa aactgcccac gcaaacaagc
3901 taataacgat gagacaactt cccaatatac gggagcagaa catcaagcaa ttcgggattt
3961 gtttgcttca ctgaagcaat cagtgcgtga agctcattct ctacatcatc aatcacatca
4021 gggtgacgtg caagtccacg caaaaggcaa cccatcacgc gttcttgaag tgccagttgt
```

Figure 10A

```
4081 aaatgctgct gatgaatctg tgcttgcata tcttgaagcg ttttttgcat ctgatcgttc
4141 atcttctgaa ctccttaaat taagtaatcg tttattcaat ttagggcaag catacaacaa
4201 aacaggtaaa taaaaaagcg agggcgcggc aatgtatgtg tctgaaaacg aaagtgcggt
4261 agaaaaatgg catcgtttaa acggtgtgcc catgtcgaaa gcaagaaata gcgaagaaac
4321 cttgcatgaa atgggcttga gtaaatatcc cactgaacgc gcttttaatc atctttccga
4381 tgagcaaaaa ggcatgttaa aagcgttagc agatattgaa ccttttgaag attacatctc
4441 gcccgatctg actggcgata agttatggca ttacaacgaa aaaggcattg ataaattaac
4501 caaagcattt cacgccatgt cagcacttcg cacgccttt ccgcacgctt taacccgtcg
4561 tgattttac aatatcgacc cacacacaag ggggaaataa tggcaacgaa aaaccgaacc
4621 attatcaaaa aatatgctga tcgctggcac aaagaagcct gtcatttata cgcaaaatgg
4681 ctcaacgcaa aacgccaagg cgatgaagaa gccgcaaatt attatttcag caaatatatt
4741 acggctggag acaactggat caactacacc aaatttgccc attaaggaaa actcttatgc
4801 aagaacacat tattgattta tctgaacgtt atgcccttaa gttaaacgaa aaccacgttt
4861 atatcctgta caaaattgaa ctcaatgaaa acggcactta tcagcgcaaa ggcggcgcag
4921 tatgtaagga tttaccttcc ttgttggaca agctgattta ctgtgaattg atgaatgaga
4981 aagtagaaac tcttgaagat atgcgcaacg tgctacacgc cattcacagc gaagtaacac
5041 gcatcgccga aattcaagcc acttatgcac aggcataaac ccttttttac ccatatctat
5101 taatttaatt catacaaaat aaatatttat gactaaattt aatctagagc aagcattaca
5161 aggtgcgcca gtccgtctta caacggttt taaagcttat attttttgcgg atgtgagctt
5221 gcttgctatt aatgaaccat acccactgat tggcggatat gcctattcga tcagttcatt
5281 ttacgacaat caagaacatc aacgatttga agaatgccgt tgggcaaaag acggcaaatg
5341 tgatcgttta agcgcattag ggtcgattgc tgggatgtgg gaagattagc tatgcaatca
5401 atgtgggaac aacaacgcaa caacaacctc actgccaaaa atgcacacat ggcggtggtt
5461 gcctgtgaac gttatcaagc cgcagaaaat gggcataaat ttgcaccgca cac tttactgcct
5521 tttgatgaaa gctgctatac gccactacag ctagaattat tcgccacaaa ccctgttgat
5581 tttgagttta tcgaacaaaa acttgaaaac ctcccacgcc aacgtcagcg tgaatatttc
5641 cgtaaacttt atcttaaagc ctatcgctct gtaaaagacg atggctcgat tgtgtttgcc
5701 ctcggcaata acaacgtcg atatgccaat gattatttgc gcaatgtatt agatgtgcgt
5761 ttacaaaaag tcttttcaca atacaacgtg aacgtagatt ttttgcaagc gttcatcaac
5821 accccacact ggttgttatc tgtcaaagat gaaatgcaac aagccgtgca gttctccacc
5881 gtaccaaccc gtgaagaact tgccaaacac tacaacgaat tacattacag cggttttcat
5941 tttcgactgt taggcaccca acaaaagcaa aaacaattac ctttctattt aatcaccgaa
6001 agcaaattga aaaaaatggc gtatgaaatg gcaacggcat ttattcgatt tcaatgtgat
6061 tgctcccact ttttaaaaaa tggcatcgaa aaagacaacg agggcgacat tcaaggctat
6121 ttctatcagc tctataaatg gtgtggcgaa atcgcctttt ctgcaggttt caaaatccct
6181 cactgggaaa aaatagaaaa tgacaaacgc atcaaagccg aacatattga tagcacttta
6241 attcgcttga cgtgcgaaaa atggtggttt aagcaaatgc gagacataca aaaacgtatg
6301 gtcgagcata tcgctattgc ctgtcggcgag gtgcgcgcca atgccgccag ttatatctct
6361 aatcaaagtt ccaagaatg gcaactgcaa caacgcaaga atcacgatta cttgcgtgcg
6421 atgattattg agaacatcga cacccagaa gaacaggtcg agcttttcga catgttcttg
6481 aaatcatctt ctaacccagc attacgcaga aatgaaatga tggtgcgctt gcgtggtttg
6541 gaagagtggg cagaagaaaa caacaatgaa gccttatttt taaccctcac tgcgccatca
6601 tcattccacg caggaaacgg caataagaaa tggttggggg tgaatccacg cgagacacaa
6661 aattatctaa acaaagtgtg gcaacagttc cgtgcgttat tgtcgaaacg taatattaaa
6721 ttttacggta tgcgagtggc agagccgcac aaagacggca cgccacactg gcatgcgcta
6781 gcttatgtgc cagcagaaca taaagaagaa gtcatccgct tatttaaaca aaaagcccta
6841 gaattagacg gcaatgaaaa aggcgcagca aacaccgct gcaaagtgga aaaatgcgac
6901 aaaacaaaag gcagcgcaac ggcgtacatt gccaaataca ttgcgaaaaa tattgacggt
6961 tttgcccttg ctggcgaagt gtcagatgaa gacccgacac taagcctaca cgacaatgcc
7021 ttgcgtgttc gtgcagtgc gagcgttgg ggcattcgtc agttccaatt ctacggcggc
7081 gcatccattt gtgtttggcg tgaattcgc cgattaatca gcggtcaagc cgatgatgaa
7141 attatcaata aagcccaagc agccgcaggc atcgcgaatg actatgcggc atatatggaa
7201 attcaaggtg gtgcgcttgc taaacgtgct gatcaaccta tcaagctcga ttatgaaact
7261 aaaacctgcta taaatatgg cgaacaacgc aaagccatta ttggtttagc gaatagattc
7321 agcctaaaac aagtcatttc acgcaccaaa aaatggcaaa ttaaaaaacg cccacaagat
7381 tttgcacaac gcacagaatc tatggttgag cgtagctcaa ccgctaacaa tagcgcacgc
7441 agtgcgcttt ggacttgtgt cagtaactgt aaccgctcaa atcttgagca aaagatcaaa
7501 ttactgcac aaccgatctg cacaccactt agcgcacaaa aattagacta tttattcaag
7561 tataaacggc taaccataga taaatataca gccttagaac tcaccgaaaa cgatgtgcag
7621 ttagtgaaac ggaatcaaaa catgatgacg tcccttcc ctgtgccaag aaaccttcaa
7681 aaactcaaaa attttcataa aaacaacgt attcaatagg agaaacgca atgaataaaa
7741 gaaacagaa acaaatcagc cgaatcttag cagcaaaacg tgtaaaaaag tgcggtcaaa
7801 ttgatctgaa aaatttacaa gcgcaagtct gggatcttgc tgtgcaatcg caacaaaccg
7861 caagttgggt aaaaacacaa ggcgaaacta atcgtcgtat ttgtcgctat ttttcaaaag
7921 aaatagaacg gcttgagcga cgtaatatgc ctggttattt tgaattaatt ctgcttgcga
7981 ttgctgcagg gtttatcggt ggtgtagtgg gtctttttc gtggttatta gcaattcttt
8041 gagtaaaaat aatgaacaaa tccaatacca aaaaatcaga taaagactta tgggcgacac
```

Figure 10B

```
 8101 cttggtgggt tttccattat gcagaacaat atttcaacat aaaatttgat ttagatacat
 8161 gtgccatgga acacaacact aaagtgaaaa actttatcac cccagaacaa aacacgctaa
 8221 cagcagattg gcaagggcgt tactgttgga tgaatccgcc ttatagtaac ccgttgccct
 8281 ttgtcttacg tgctatttcg caaagcgtgt tacataacaa aacggtggtg atgttgctta
 8341 atgtggacgg atcaacaaaa tggttcgata tgtgtgtgcg taatgcaaaa gaaatcgtgt
 8401 atatcaccaa ttctcgtatt cctttcatca ataacgaaac aggcgaggaa actgaccaaa
 8461 acaataaacc gcaaatgctg gtgctatttg agccaaaagc accttacggc agtttgaaat
 8521 cgtcttatgt gtcgttgcat gaaatgaaag aaaaagagat gttgcaataa tttttttaaaa
 8581 aagtggttat tatacctata aaatagttgt tttatttttt taagtgggta taataaccac
 8641 cattgaaagg caagagggag aaacagtgga tagcaaaaca gcaataaaaa tgatagaaga
 8701 ggacggttgg tatttagata gagttaaagg tagtcatcat caatacaaac atcctacaaa
 8761 aaagggaacg gtcacgattc cccacccaag gaaagacttg gggcatttag aaaaaagcat
 8821 taaaaaacaa gcggggcgt aaagcccccc ttataagaat aggagaaaaa atgttatacc
 8881 cgatttgtat cgaaaaagta aatgatggtt atgtggtatc tgtgccagat gtgccaggct
 8941 gttttctgc tggggatacc ttatcagaag cgatgttaaa cgcaaagaa gcaatctctt
 9001 ttcacattga agggatgtta gaagatgatg aagaattgcc taaatctaac ccaatagaac
 9061 aatatattaa tcagcccgaa tataaagatt ttattgtcac tgttgttgat gtagatttaa
 9121 ctcatttaat gggtaaggca gaaaaaatta atattacggt tccagcgtta ttactgcacc
 9181 gcattgatca gtttattgcc acccatccag aatataagaa tagaagtaac tttttgtctc
 9241 aactagcaac aaatagatta ctttctgcat aataaaagcc gctatttcta gcggctttt
 9301 attcatctaa tatcttcctt aaattagttt tttcttcttc tgaaagtttg cttaaaacta
 9361 gttcaagtaa tttatcttta gttaattgc tacttcgtgt tgtgtggcta aattccatat
 9421 tcatgacaaa tctgtgaccg cacagggggt tttacacgc acaataatat cttgtaaatt
 9481 cactgtgtat ccgttcagat ctttcgatta ctgatttcgc attgcaaaca gcgcagtaaa
 9541 tatctgttgt tcttgccatt ttccccaaag ccatcacaaa ataactgca aataattata
 9601 tcaatgaatg gcttttgta caggttaaaa acaaaaatta ttttgcgaaa ttttgttcgc
 9661 ggaacttaat ttttaataag ttttttgattt ctggatcttg atttattgtt tctgcaataa
 9721 tctcttgtaa tggcattact tcatcatagt gatacacttc acgatatttc aacggatcgc
 9781 caagcccgcc cgtatttgtc ggaataatac cacttaaacc tgcagggaat cggtgtgcgg
 9841 ttagcacatc ttgtgcagag atgtttttga tattcgcaaa ttcatctttt gtcccagtgt
 9901 cgccaatagg aatcactttt aacccgtcag gatgaccgtt cgcaatattc acaaacatgg
 9961 aacggaagtt tccaactccc ttagattcac tgatctttct tgcgatctct tcttccattt
10021 cttcggttaa gtcgggatct gtggagtaca aataaagcc catatgcgca ccattgctaa
10081 aatagcgacg gcgaaatact gtcgcatcag aatttagcaa tgctgattga ataccgccta
10141 cataatcggg cgatccataa acttgttgca tagggtcgta aagtttaata aagataatat
10201 ctttcgcatc atagcgatag atttcttgtg cggtatcata aagcgatttt ttcattaaat
10261 aagaatagcc gccatcttta cgcacgcgta aataaaggct agataacggc acaagacgca
10321 ccacttgccc aaacccatta cgcacttta aaagccccac atcaccaaac tgaattaagt
10381 taaggcaaag tgcacgcata tccatacgag ataatgcttt gccgccttcg tagagggagc
10441 tcaccatatt ggcacgacta tgcagaattc cgccgtgttg tgcgttttgg tgtggtagtt
10501 ttgccagtgc atggcgattt actggtggta aatagcaatt gtaattttca tcaaagccta
10561 tgccgacata atctagtgca ggcgaggcac tgatttcatt taatgaaaaa gtgcggtcat
10621 taattgggc aataacaatc ccttttttat tgtctgtttt tacattagtt ttcatttagt
10681 acgctcccatc cgcgacgttt gcgaggttta tcacttaagg atttttttatt aatggcgtta
10741 caaatggcaa aaaacacatc ggcgtgctgt gttttcacag tgcgttcagc cgtaaatgtc
10801 atcgtattgc cacttttggt tgattggtgc ttaatcatta aaaagctcgg tacaatatct
10861 aattcgcttt cgctccactc aatttgccca tgctcaacca aatcatgtac tttcagcacc
10921 atacccgtct tactttctgg gttgtaaata atggcagtgg cggcacggcg tgcaaactct
10981 ttaccaact cataaacccc atagcccacg cctgtggcat caatgccgat gtaagtcata
11041 ttgtatttt cataaagggc acgaatttga ttggcttgat agacatagga aagtccattc
11101 cattgataac gtgcaagcac gcgatatttc tcactgggta aggctggcgg agcaataatc
11161 acaaaacttg ccccatcgcc actgtgtgcg gggtcgaatc cgcccaaac ttcacgatca
11221 ccaaagggc gatccgcttt cgggttaaag tctttccatt tcgaaatatc tacaccacat
11281 tttaaaagtt gatgaacggt gaaaatagaa tccgcatcat caatccaaac gcacatataa
11341 agctgattaa acgcatattt gctatagcgt tgtttcagtt tttcaatgtt aaataacgtg
11401 cccgcaccgc ctttagtgc gtcttcaatg gttaccacat aacgccactg accatctgga
11461 caaagtcgcc caccgtcacg caattctgca aagttggga atggcacgtt tttgcgttta
11521 gggtcgccat ctcgcaagtt atcgccactc cagaacgaat aagattcgtg gaatttgaa
11581 gacggtgtgc tgaaatagt ttcgcgcgta ttcgcgtgtg ttgccatcgc agaagccaca
11641 tcattgaatc gttggaaatc tcgaatccat gcgtattcgt caccatacac atggccactg
11701 ttaccttgtg acgtgttttt gttggtcgat aaaaaatgca gttccgcgcc attgcttaaa
11761 ataatcgggt tgccagtcag ctcaacaccg aaatattccc tcgccatctt cacaatgtaa
11821 tttttaaaga tttctgcttg ccgtttactg gcggataaga aaatttgatt gtcaccgctg
11881 aaaattgcat cttccaacgc ttcaaaacta aaataatagg tcgcccaat tggcgcgat
11941 tcagaatat tgcgcacatc gtggtgcttg ttagcgcgga tgtgttttg ataatcaaat
12001 aacgaatcaa taaacggctg gcacatttcg ggcgagacgt gggaaatatc atttttttacc
12061 cgcttttttct ttttatgttc gtcaccatcg ccactatcgg caaaggaacg atcactgctg
```

Figure 10C

```
12121 gaaacatcgg cagaattgac cgcgcttttt gctgtcactt tagctaccgt tgcggcacgt
12181 tgcttttat actgaatatc tttatcgatc agggcttcaa gttctttgat ttcttgatca
12241 cttttgtttt cacgttctgt cagcgtaata atgcgtaacg caattaattc ttcaatcccg
12301 ctttcgctga ttaaattgcg ccagttgtat ttttccgccc aatagtaaat cgggcgtgtg
12361 ctatttaaac ctaattctc agcgatctct ttcggcgtgt atttttttaa atataaaaac
12421 tttgccgcat aaatcacttc gtcatcgtag cgttttgttt ttctttttct tagcttagat
12481 tccgtcattt tttatcttgc tgttgttttg tggatgtatt gtggcaacaa aaaccgcaaa
12541 aatttaatgg caagatttgg atatcttcgg atatagcacg ttatccgtct atatccgaag
12601 atatccaaat tttgcccagt gattttgtaa aaagatcgg caaaaatgac cgcacttaag
12661 caaacaaagc gaaacgcag gcattttaa aatgaataaa tcaaaactaa aaactgattt
12721 tatttgtatc gctacatcgg gctacaccgt ggacggccgc caaatcaccg cccaagaatt
12781 gcacgaaatg gcagaaacct acgatcccga acactacact gcgaatctat ggccagaaca
12841 tcgtcgttgg ttcaatatgg gacaagtgat cgagctgaaa accgaagaaa acgaaaaagg
12901 cgaaactcaa cttttgcca tcatcgcacc caataaagaa ttaatcgaat caaccgtgc
12961 aggacaatac ttattccacca gtattgaaat taccccgaat ttccgcaaca gcggaaaagc
13021 ctacttatca ggtttaggtg taacagattc cccagcatcc ataggtacta cagaattaaa
13081 atttttcaat gttgaacaaa aaggcagtgt ttgcggtgaa tttatcaaag tagatttttc
13141 tgcaaagaa gatgttgaag aagataaggc attacgcacc ttagcgaatg cttttaaaaa
13201 gttatttca tcttccaccc aaacggaaga acaactaact cccaataaca acaataataa
13261 agaggacgat gcaatgaacg ataaacagtt cgagcaacta attgaggcgg tgaatggttt
13321 aggcgcaaaa attgacaatc attttcagc caaagtagaa accaaagaac caaaaaacaa
13381 accagaagaa aagaaagatg aacagccgca aagcgtaaca gcagagcagt tcaatcaact
13441 tttaacaacg gttcaggcgt tggataaaaa attcaacgaa ttaagccaag aacaaaccac
13501 tgtgccaagc ggtgtaccaa cagtagaaaa cgaaaatgtt tatagcttaa acggttacaa
13561 catcgactta tcaaaaggat tctaacaatg aataaacaag cgtattacgc cctagcggca
13621 gcattagcga aacactttaa tcaacctctt gattcagtgt tgcgtggaga agtttttgca
13681 cttaaagcac ctgaagcagc attattgggc gaaaacattc aacagcgttc tgatttcttg
13741 aaaggaatta acatggtgca agttgcgcat actaaaggta ctaaattatt cggtgcaacc
13801 gaaaaaggcg taaccggtcg taaacaacaa ggccgaaacc ttgcaacatt agatcactct
13861 caaaacgggt atgagttatc cgaaaccgat agcggcattt tagtgaattg gtcgttattt
13921 gattcattcg caattttcaa agaccgtctt gtagaactt acagcgaata tttccaaaac
13981 caagttgccc ttgatattt gcaaattggc tggaatggtc aaagcgtggc gactaacact
14041 acaaaaacgg atttatcaga tgtgaataaa ggctggttga aactttaca agaacaacgt
14101 gcagccaact ttatgaccga atctacaaaa tcctcaggca aaattaccat ttttggtgat
14161 aacgccgatt acgcgaatct tgatgattta gcctttgact taaacaagg cttagatttc
14221 cgtcatcaaa accgtaatga cttagtcttc cttgttggtg cagacttagt cagcaaagaa
14281 acgaaactca ttcagcaaaa acatgctta accctacgg aaaaagctgc attaggttca
14341 cataacttaa tgggctcatt cggtggaatg aatgccatta ccccaccaaa cttcccagca
14401 cgtgctgcag cagtgacaac ccttaaaaat ttaagtgtgt acaccgagc tgaaagtgta
14461 cgtcgctctt tacgtaacga tgaagataaa aaggtttgg tgacatctta ctaccgacaa
14521 gaaggctatg ttgtggaaga tttaggttta atgactgcaa tcgaccacac caaagtgaaa
14581 ttaaacggcg aagtatagga attaacaata aatgggaatg cgagattttc aacgccaaat
14641 gcaggcacta gcagaaatta atcaagtatc agagagcatt acacaacaaa gtgcggttgc
14701 gactcacggt aatgattatg ccgtgcttga aatcgcctta caaaatgatg tgaacgcagt
14761 acgcgcattc tcgacacgtg ccgaaaaatt agattacaag cgtgaccgct ttttgccgaa
14821 gtggttgccc tttgtgaatg aatatttaga taaaggggca atttatcaga atgattactt
14881 ggtttattgc attgtgtatt tgtttgacat tgctgatttt gaccgagcct tgtcactggc
14941 tgaaaaagca attgagcaaa atcaatctat gccgcaaggg tggcaaacca cattgccaaa
15001 ctttgtcgca gaccaaattt acaactggac cgataaaacc gcctcagcag gtcaatccgt
15061 ggagccatat ttttcacaaa cttttaaaaa cgtggcgacc cagtggaagt tgcacgaaat
15121 tgtcacggca agtggctca aattagcggc ggcactgctt ttacgcagtc cacaaggcaa
15181 agtacaagcc agtggtattg atgatgccga aacacttgtg ctggctatcc aattgtgtaa
15241 ccgcacttc caactcaatc agaaagcggg tgtaaaaaat atgattgagc gttgtgtcat
15301 gcgtttaaac gcattggcaa aatcgggtaa atatgaccca caagtcttc cccaagtggc
15361 aggcttgagt tggaatcaa gtcaaattaa ttttgatctt gtgataaaaa aactcactgc
15421 ctgcccactc caaacagcg aggaaggcaa tgtttaacgg cagaacgcaa gattacgacg
15481 ataccgtcat cacaaataac ggcttttggt cggatattta tgttgaagag tttcaaaagc
15541 aacgcgccat tccattacaa attcctgtgg aatggtgaa aacggcactc attgccgcca
15601 tgcaaggcgt taatttagat cttcgcgaag ttgaagaaaa tcaccgtaaa agtgcggtca
15661 attctgtgca agaaatttca acacagcgga ttaatggcga aaactacgct gaaacccttt
15721 ataaaaaagc ggtctttgcc cgagcaaaag cggaactatt acccgaattt aacacccttt
15781 cagggcgtga gattcatcaa aatcgtgatt acgtggtcga gcaaaaagc ctattggcag
15841 aggcaaccca cgctatccgc acattgaaag gtaaaaaacg gggatcggta tggctgctgt
15901 aaagaaaatg ctgtatcagc aactcactga ttttttgctc accaaattgc cgaaacgcta
15961 ccacggcaat ttttatagtt ggatggaaaa cggaaagctg gtgaaccaag gcaagcaagt
16021 gaccàataat gggatcgaaa tttgtcatat tcaatgac ggtattctgt ttttaacga
16081 atttcctttt aaggaaatat caccggctta cttaatggca ttaattcaaa tttggctcaa
```

Figure 10D

```
16141 tgaaaatgac gatatgcgcg attgtctcga caattacgaa acgccctttg acattgaaat
16201 tattaatgat gatgtggctg atatgagttt taccattagt tttcaagagc cattaaccgc
16261 cattgaagac aaaaacggcg aattggacat tgataacaag aaatatagct tatcgactat
16321 tgatgtttgg atcgcaaaag aaatagaact tgaggcgata gtagatgcaa attaggctcg
16381 gattaaagca agaagattta gatgcctttg ttagagattt acgtacatta aacttaaccg
16441 gaaaacaaaa gaaaaaaatt cttacctgga cattaggtgc aataaagcgt aaatctcaaa
16501 aaaacatcag agaacaacac tcaccagatg gaacagcctg ggaaaagcgc aagcccgtag
16561 atggtgaaat caaaaataaa cgattgttaa aaaagttct tcgttatgct tcaattcttg
16621 cagaagaacg aggaaaaggg cgaatttact ataagaatcc attaacaggt gaaatcgcac
16681 aaaaacaaca agacggattt acagagcatt ttagagttt tgcaacggac aaaaacaaaa
16741 atggttcagg caatgaccgt gccacaatta gacaagccca aaaattaaga tcattggggt
16801 atagaaaacg taacgggaaa aatagacagg gaaaaacaaa ataccggctt tataccatta
16861 aagaaattcg tgaaagatta acgaggacat gggcgagtat ggagatccgc cgcttagaaa
16921 ataaagtgaa tgcaggcaac ggaaaaacaa actgggaaat tcatgtacca gcaagaccat
16981 tcttagatac aagagaaaaa gaaaacgtag atattctacg agaaattaca ctgaagtttt
17041 tatcaggtga atacaaataa aaaataaccc cgaatcacgg caatgattcg aggttgtaaa
17101 cccttacaa accattaacc aataaggagt taattaatat gaatgattat attcaattta
17161 tccaactaat caaggagatt ccacgatga acaacgctta tttactcttt gcattattac
17221 tgattgctat tgcagtgtgg cgttcgcctg aaattatccg tgcttggatt gaatacaaga
17281 agttttctaa aaaataaatt ttttatcaca accataagag gacagtaacg aatgttccca
17341 tctgtacaaa ttaacgccct taatcagtta agtggcgaaa ccaaggaaat tgaacgccac
17401 gcattatttg ttggcgtagg caccactaat caaggaaagt tattggcatt aacgcccgat
17461 tctgattttg acaaagtatt tggcgaaacc gataccgact taaaaaaaca agtgcgtgcg
17521 gcaatgctta atgctgggca aaactggttc gcacacgtgt atatcgcaca agaagacggt
17581 tacgactttg tcgaatgtgt gaaaaaagcc aatcaaaccg cctcttttga atattgtgtc
17641 aatactagat atttaggcgt agataaagca agtattggca aactgcaaga atgctatgca
17701 gaactacttg ctaaattcgg tcgtcgtacc ttctttatcc aagctgtaca aggtattaat
17761 catgatcaat ctgacggtga aacatgggat caatatgtac agaaacttac cactttgcaa
17821 caaaccattg tcgccgacca cgtttgctta gtgccttat tatttggcaa tgaaacaggc
17881 gtattggcag gcgattagc aaatcgtgcc gtcaccgtgg cagacagccc agcacgggta
17941 caaacaggcg cgttagtgag cctaggcagt gccaataaac cactggataa agacagaaac
18001 gagcttactc ttgcgcattt aaaatccctt gaaaccgcgc gttattctgt gccgatgtgg
18061 tacccgatt atgacggcta ttactgggca gacggtcgca cgttagatgt agaaggggc
18121 gattatcaag tgattgagaa cctgcgtgta gtggataaag tggcgcgtaa agtgcgttta
18181 ttagcgattg ggaaaattgc agatcgttct tttaactcca caacatcaag cacggaatat
18241 cacaaaaatt atttcgccaa accgcttcgt gatatgagca aatccgcaac catcaacggc
18301 aaggatttcc caggcgaatg tatgccaccg aaagatgatg ccatcacgat tgtatggcaa
18361 agcaaaacca agtaaccat ttacatcaag gttcgcccttt acgattgccc gaaagagatt
18421 acggcaaata ttttcttaga tttagacagc ttaggagagt aaacaatgga acgtattagt
18481 ggaatgagtt ttgacttcta tttattcggg ttgcctattc atgcagagtc tatcagttta
18541 tccattacag ataatagtac cgttgtacaa acacgtggaa ttccagatgg ttgggtaagc
18601 ggtgatgtgg cagcagaagg cgaaattgaa ttagatgcaa aaaatttctc aaaattatca
18661 gctgcagccg ccgcagcagg aagttatcgc agtttacccg aaacggattt taccttcttt
18721 gcacaacgtg gtgggattcg cgacaaagtg gaaacctttg gcaataagat tattttaacg
18781 gatgtgttaa atatcgatcc gaagggcggg gctaaatcca tgaaaaaact aaaatatttt
18841 gtgacaagcc cagattttgt acgtattaac ggggtatcgt attttatctga tgaagataca
18901 cgcgatcttc tcggctaagc gaatttaggg gctgactgtg ctgacgtata acaataataa
18961 acaagcaagt gcggtcagtt tcctaaatgt tttaaggaaa ttttatgaat agcaaaatag
19021 atagcacaat tccgtttatt ggctcactca ctgcgcttat tcaggatat agcttgcatg
19081 aatgggcatc attattcggt atttatttg gtgcggtttc agtgtggatc gcttaccgaa
19141 aatacaaaga agacgtacaa gcacgcaaag atgaattagc ctacaaaatg ttggtagcaa
19201 aaattgaagc aaaaaaatta gggatagcaa tagatgagta aaaaatttgg tgcaatgatt
19261 ttatgttcag ccgcagctgt cgcagccgct tttttgccc agcagaaagg cttaccaacg
19321 caacaacaaa atcaaattag cccaaaagcg gtgtcaatga ttgtgaattt agaaggttgc
19381 gtgcgtaatc cgtacaaatg ccctgctgat gtgtggacaa atggagttgg aaacacctat
19441 aacgtagata aaaccaaaat tttaaccatt gatgaagtag caaccgattt acgccaaaac
19501 atcaaagagg ctgaaaattg cattaatgcc gattttaacg gcagaaagat gaatcaagat
19561 caatatgatg caatgacctc actcgccttt aatgtgggct gtggcaacat caaaacctat
19621 tacagcaaaa cccaaggtaa acgtgtcgca accacgattt atcgcgcagc acaagcggaa
19681 aactggatat taatgtgtaa tcgtattgaa gattttaaca aatcaggcgg acgtgtgcta
19741 aaaggcttac aaaaccgcag agcaaaagaa aaagccctat gtttggggga ataatggaat
19801 ttaaagcctt atttatcggt gtattttga tggtgtttgt gggttgtatt ggttctacct
19861 tgcactataa aaagcaagca gaaaccaccg cacttttact aaacaaagt gaacaaacca
19921 tcaaacaaaa taaagtgatg ttgcaacggt atgaaacaca aaatgcaaaa ttgacttctc
19981 aactcaacca agcaaacaaa aaagccgaac aacgcagcca acaactaaag gacgtgctac
20041 acaatgcaga aaataaaaat tggacttatg gccgcgtgcc taacgatgtt gctggcgtgc
20101 tcaaccaccg cacccaagcc aaataatatt cggttgattt gcccacaaac caccgaatgc
```

Figure 10E

```
20161 agagcattaa gcgtgaatat tcgcactaac ggcgatttag cagagggttt aaatcaagcc
20221 ttagaccgct tggagatttg cactacggct tatgcggcta tcaataagtg catcaccgat
20281 ttcaacaacc aaaacagaaa ccaaaaggaa aactaaaaat ggaaaaaaca caagcgcaat
20341 cattgttaga aaaacttact ggaaatctta aagattccgt cacattaaat gttgcaggcg
20401 ttgattttac ctttattcga gataacgcgg cttacgatca aatgttaaat gacattgaaa
20461 gtaacaataa agtgacacct atcaaagatt atttactggc gattgttgcg cgcgaacaaa
20521 aagaggcatt gcttgaaatt attcacgtgc caacactggc ggcacagcta gcagcgaaag
20581 taaatgaagt gtttgtgcca gaaattcaaa ttaccgtaaa aaactaacgg agcgtgtggc
20641 aagtatcgag cgcaacgggt tatcacaagc cattgcgcta cgtatgcact atttaccaca
20701 cgccgataac agcgactaca acttagcacg cgcaatatgg ttacacaaac agtattttga
20761 acaacaggca aacgccgtcg caagcggtat cgccaaagtc ttttaggatt tcattatgtc
20821 agcagcacaa gggcttgaat atatcatcag cttaacagac caactttcag caccgttgaa
20881 aggggtcatg aagtctattg atgatttggg caaacgtggc gaagcagcaa tgaaaaaaat
20941 cgggctgggt gtggcaggta ttgtcggtgc aggctttgcc ttaaaaagtg cgctagatcc
21001 cgccattgag ttaaatcgcg ccataggcga agttcgctcc cttggggttg ccgatgatgc
21061 gttagagaaa ctaagcaaaa ctgcccttaa tttttccagt caatatggcg aaagtgcggt
21121 gaatttttgtg cgatcttctt acgatattca atcagcgatt gcagggctaa atggtaacga
21181 attagccgaa tttacccaaa catcaaattt attagccaag ggcacaaaag ccagcgcagc
21241 gaccattacc aattatatgg gcacaatgta cggtattttt gctgaagatg ccgccaaact
21301 aggaaatgca aattgggtaa ataaaattgc agggcagact gcccttgcgg tgaaaatgtt
21361 taaaacctca ggcgatggaa tgagtgcggc atttacctcg ttaggcgcag ccgcaaaagc
21421 cgcaaaaatt gatgtagcag agcaatttgg cgtgttaggt aacttacaag ccacaatgag
21481 cggaagcgaa gcagggacaa aatacaaagc cttttagct ggcgtgagtg gtgcgcaaaa
21541 agaattaggc ttaagtttg ttgataccaa tggcgatatg ctagatatgg taaccattct
21601 taacaaaatt aaaggtaaat ttggcgctaa cttagatgtc gcacaagcaa caaaactgaa
21661 aaaagccttt ggcagtgatc aagcggtcga tttaattaaa ttactcttgc cgaaaacgaa
21721 agaattaaaa aataacatcg ccgctattac aaaagtcagc gacacaaaag ccttggcaca
21781 aatggctcgt tcaatggttg atccttggtc gcgccttagt caaattataa cgggtgtcaa
21841 aacggcaatt ggggcgaaa tattgaaaaa acttgatcct attatgcaca agtggcaga
21901 tctaggacaa aaatttattg attggctcaa aacctataaa aatattgcac gctggattgg
21961 ttatgtaatg ggattactaa ttggatctgc gggagttgct gcagctatca cattatttag
22021 tgggttaatt ggtgtaatta aaatttttagg tatctcattg ttcacaattt tggcacctat
22081 tcttatttt accgctaaaa ttattttttgt agtagctatt gtttataaat ttcgtacaaa
22141 aattcttcaa tttattgatt catttgtaca aggttttaaa ttagctggcg tatcagttga
22201 accacttta aatgctattt atttaatttg gggagcattt aaaaaattcg gctcggcagt
22261 tatcaaatta tttgatttat ttccagattc atttcaaaca atattgacat tcaggatat
22321 cgcaacagtg gctggctttg ctgtgggaat ggtatttaat ggaattgttg ccgttattga
22381 attaattgca cggcaaattg aagcggtagc gactattttt agcaatgtcg ccgatgtcat
22441 tatcgccact tggcataatg tcattgatga ttggggaaagc aaaagtgcgt gggatatatt
22501 caaaggctta gcgacaggaa ttggtcaaat ttttacaacg attttaaaag ggattaaaga
22561 tcaatttatc aatacgatta attggattat tgataaagtc aatatagtca gtgggaaaat
22621 tggctttgaa ttacctaaaa ttccgaatac ttggttaagt gatgatgcac aggtaacaac
22681 agtaaccgct gcgtcaaata tctcaagttt aggattaaac gctgcagtag ataatacatc
22741 ctggagaaaa tccccaagta ttgatttacc aaatagccta aaccacaat taaattcaat
22801 gcctcaagga tctgtaacaa aaacattgac acaaaaccgc acagaacaac gcaccgtaaa
22861 ctatggtggt gtcactatca atagtaacaa cagtgaagaa atttggcaga aattgcgcaa
22921 taaagaacag ttagcagcag ggtgataaat ggaaaaactt taccttgatt tactgattac
22981 gggcgaaaac attacgctag atagcggcaa tcagccgtta atttgcgata accgaatatc
23041 tattgcgcaa gatattaaac acgccatttt agaaagtgga ttggcgacac aacttatcgc
23101 agagcgttcg cgcattttac gccgcgatat tattttgcaa atggtgttat tggttgaaga
23161 agatgtgcgc ttgattccag gtactgtttc cattagcgaa gaacgtttag ggcagttatt
23221 tattaccgct gaaacttatg aatttgggcg acttgatgaa ttggagttac gtttaaatga
23281 gtgaaaattt taaacaaatg ttagctgaaa gtggattgcc cacagaagaa acgcaaatcc
23341 gacaagaatt tgaacgctta accgaaaaag aagggttaat cactaataca agccgaatga
23401 gtccattctg gcgattaatc actgctattg cggttaagcc tgtgaagtgg ctgacagatc
23461 attttaattgc tgaaatctg ccgaatttat ttgtaaaaac ggcaaaagac agttggttac
23521 aaattcaagc ctgggcagtg ggcttagatt ttaaagccgc aacaaaagca gaaggcgtcg
23581 tgcattttac aaaagaaagc gatgtaaccg atctgacaat taaagcgggc acagtgattc
23641 agacagagcg tattaatgat gtgattttcc gtttgattgt cacgcaagaa accattattc
23701 ctcaaggtgt gttgcgtgcg cctgtgccag taatcgcaga gcaggctggc gcaaatttca
23761 atttggctgc aggttattac cgtatttgc cagaatctat cgcaggggta agtgcggtag
23821 aaaatttaga agattggcta acatcgccag gtgctgacag agaaactaac gacgaattac
23881 gagaacgtta tcgcacgcaa ttttcgagtg ttgggcaaca ccatattgac agtgtttaca
23941 aaggcatgat tgcgaaagtc gccgccttat cggtggacag aatttatttt aaacacgatg
24001 caccacgtgg gccaggtaca gcaaacgctt atttgttatt ggacacgggt gtaaccagtc
24061 agccgtttat tgataaagtc aatcgccatg tacgtgacga gggttttcat ggacacggtg
24121 acgatttaat ttgctacgcc atgccagaaa ctaaacacaa tttaacgtgc gccatttact
```

Figure 10F

```
24181 tccagccatc tatttttgtc ggcgatgtgc gtaaacaaga aatcgtgcaa caagtggaaa
24241 atatgatccg ctgcgcattt cgcgaaaata ataattatgg cgtaacaagg acttaccctt
24301 ttagccgttt tagttggtcg aaattgggcg aggaaattca cgacaacatc agcgaaattg
24361 catctatcgt atgggggcaa atcgacattc aaagcgagtt atctattcca cgcattcagc
24421 aattatccgt cacagtccaa aagtaagggg caaaaatgaa aataaaattg ccctttttgga
24481 tggataaagg cgaattaagc aaaatcgctg tgctattcgg aaaatggtgg gattatgtgt
24541 taagtgcggt caaatttccc ttcaatattt tagatgaaga acactgcagt gaacgcattt
24601 taaatttaat cgcctatcca cgcgacgtag aacgatttga gggagagccg ttagagctat
24661 tccgcaagcg cgtgaaatat gcctttttaa atgcgaaaga tgctgcagt aaagcgggct
24721 ttatccgcat ttttgaacgc cttggcattg gctatgtaga aattgaagaa cggttcgata
24781 gggaaaattg ggatgtgatc aaaattcgaa tcagtgattc acaattagca aagaaaacag
24841 aattactcaa tttaatcatt cgaaaatatg ccgcacttg tcggcgttat acctttgaag
24901 tgatcactaa agaaaccgta agtatttatc acggcgaatt taaccatgat caccaaagtt
24961 tttatgtgaa agtaaacgga taataacaat aataagaggt ttatttatgg ctagtttaat
25021 tacgccacaa tttgaacgct acgttgcaga acaaactatt gcacgtggca cagtacagtt
25081 tgatgaattt atttttgcca catcccagg tttaaatgag aacaatcttg cgcaatatct
25141 cactatgccg acatcggcac aaattgtaca tcgccaagcc gtatcgcaaa gtggcgtgat
25201 taatgaaaat gccgttgtgt attctgtgac gattggtact gaagtcggcg attttgattt
25261 caatttatt ggtttgatta atcgttctaa aaatctttta gctgttgcgg tgcaaaccga
25321 tacagtgaaa aaaatccgaa ataaaaatgc tgtgcaaggc aacagtatta cgcgcaatat
25381 gcttttagaa tttagtggcg caaaagctct aacgggcatt aatgtcaatg cgaacacttg
25441 gcaaattgat tttactgtgc gactacatgg acttgatgaa aaaattcgtt taaccaatcg
25501 tgatctgtat ggcagagcag tattttcga tgatagtttt ctggttaaac gtaaaacagg
25561 caatcaattt acgattcaac caggcacggc ttatgttgaa ggcgttcgta tggatttatc
25621 cgcactttat aacctcacag caaacaattt gccatgtcca gtttatgccg atctagtaca
25681 tcattgcacc gtaacggag aataccaaac cgaaattaag tatctcaccc aatcaaaagc
25741 agattatgta gatactgcaa accgccaaca ttatgtacaa attctggcgg atattgatag
25801 ccaaggcaat gtgacagatc gccgcttgct ttcgccgttt ttaggcatga atccgctcac
25861 attagatgac acaaccgaaa cacccaaga taaatggggt catacgcaca agttaccaat
25921 tgccagcatc acaaaaaaag gcattgtgca actaagctca gctactaaca gcaacagcga
25981 aaccgaagct gcaacatcaa aagccgtgaa aaccgcctat gacaaagcag tagaagccaa
26041 aactacggcg gacggtaaag tggggttaag tggcaatgaa gaaatagcgg gggataaatt
26101 attccgtagc cagactaaat tccaaaatg cgtgttgatt tctgcaaata aaggacactg
26161 ggataatggg tataaagtct atattggtgc agattctgat aatgcacatc tggtatttgg
26221 cgatgataca ttgagattac acggctcaaa tcatcgtatt tcgtataata attatcatct
26281 tttccatgag ggctacaaac ctcgttttaa cgaacatatt ataaacaaac ctaatacact
26341 tgcaggctat ggtattggga attttaaagt agaacaaggg cagggcgatg ccaatggcta
26401 taaaccgat ggcaattatt acttagcaag cggtcaaaat ctacccgaaa atggggcatg
26461 gcatattgaa gtagttagcg gtgggcaac aaatgcggtg cgtcaaattg cacgtaaagc
26521 aaatgataac aaaatcaaaa cacgcttttt taatggctca aattggtcag aatggaaaga
26581 gacaggcggc gacggcgtgc ctattggtgc ggtggtgtca tttcctcgtg cggtaactaa
26641 tcccgttggt ttttttaaaag ccgatggcac gacatttaac caacaaacct ttcccgattt
26701 ataccgcact ttgggcgaca gcaaccaact tcctgattta actcgtagcg acacaggcat
26761 gacggcttat tttgccgtgg ataacattcc tgcaggctgg attgccttg attcaatcag
26821 aacaaccgtt acacagcaaa attaccccga gttatatcgt cacttagtcg gtaaatatgg
26881 ttctcttttca aatgtgccat tagctgaaga ccgatttatt agaaatgcat caaacaattt
26941 atcggttggt gaaacgcaaa gtgacgagat taaaaagcac gttcacaaag tgagaacaca
27001 ctgggttaat tcaagtgata gtaatatttt ttatgacaaa acgaaaacag ttatagattc
27061 acgattacgc actgcaacta caactgatga taatctcagt gataatgat ttatgcatcc
27121 gctattagat agcccaatgg caacaggtgg aaatgaaact cgccctaaat cattaatcct
27181 caaattatgc atcaaagcca ttaacagcct tgatgacgtg caattctggg tgaaggcttt
27241 cggtgttgtt gaaaatgcag gggtgcttga tgcgggtaca cttgcgcaaa atatgcaaag
27301 tgttgaacaa aaaatagaag agaataaaca atcaactttg cgagaaatca ccaatgcaaa
27361 agctgatata aatcagcaat ttttgcaggc acaaaagaat ttatctcaaa ttggcacatt
27421 aaaaaaagtc tgggaaggta gcgtgagtac tgggtcaatt actatatcag agagttgcta
27481 tggcaaaacg ttaattttttt atattcagac agcagatgat caaagtaatt acggtgattc
27541 cattgaaata gtcagttttg aagcggggtgc agaagatgaa ggcggaggtc gtttgactag
27601 tattcgtgaa atagtatcca aatataatta tcgccaagta gtacccaaag agttcactgt
27661 gtatattgct ggtgacggta aaactataac cattggccaa cttgatgcac gttctataaa
27721 acgtatttat attcgataaa ggagcgttaa atgaaagtct attttttaaa agaaaatttg
27781 aatagttatc aaattttccc tattccgcaa aacttaaatg attttgtgga aatggaagta
27841 gaaaacgaat cagagcttga gactaaacaa cttatttatt ttaaaagtca atacattcta
27901 gttgatagac aaccaacaga attacacaaa tggaacggaa acagctggat tgtcgatgaa
27961 aaaagaaaa ctgaaattaa gcgtaaactc attaaaaatc tagttgatag cattgatgat
28021 acagcggcta acattagtgc aagatgaca aggtttgccg aagatataa ggagcgagaa
28081 gctgccgcta ttgcctttaa agaagcaaat tttactggcg aagtaagcat ctatatatca
28141 agtttgcaa ctgtcgcagg acttgataat aaatcagcaa cattgctaat tttaaaacag
```

Figure 10G

```
28201 gctgaaggat tacgaacact gcaagaacaa ctcgcggtgc agcgtatgcg taagtatgag
28261 ctcaagcacg aagaattgag tgaagaagaa ttacagcaaa ttcataatga cattatcaga
28321 aaaatgaaag cattagcgga ggctcaacaa tatccagaag gttttaaaac taatgaattt
28381 taggtgatgt ttaatatgtg gaaacaacaa aaactaaaat tatccccaca ggcaaaaaca
28441 acattacaaa acgcacaaaa ggggattatt tccccttttt cgctatctgt aagtggtact
28501 aaattaggtg tgcataattg gtcgcacggc atcaaagaaa aatcaaatca ctatttgtca
28561 cccgaaaatg ccgtgaaagc actggcggca aagttggtcg attatgccga tccgaatcgc
28621 cctaaaggtg tgcaggatgt tgtggtcatt atggtgacaa gtagcaatat tgatcagttt
28681 attgcagagt tggaaaaagt gcgtgagcta ttgccagagc caacatttaa gcaagcacta
28741 gactatgcga aatcaagtaa agatttacaa gaaacaaaaa tgataaaaac gccaactatg
28801 gcaagtccat cattttccaa tagtgccgat attacgccag gttccgcccg cacaatgcaa
28861 agtattttac gtaatgccac atccgcagcg gttgcggcac aaactaaaga tccgatggcg
28921 atgattgagg cgttaaaggc agccaaaaaa gaacgcgaca aagcgaataa cgaaaaagtt
28981 gaaaaaatgt tgaatacatc ggctaatatc tatgcttttg ttgtttcaga ttatcttgaa
29041 atcgcagaaa gtaaaatgaa agtgaatgtg ccaaagtcaa gcaatatatt taccacttgc
29101 gttatgttta ttggcgcaga tttaaccaat attagaggaa tgttgcaaaa tgcagaaacg
29161 taatcccagt gtacaacttg cactaaatgg cacgccaatt tatttaaaca atattttaat
29221 gtcggtttcg gtcaaacgtg aagaaaaaga catgagcggt caaaaatcaa gtaccaaaaa
29281 atcagataaa ggcgtaaaag ccaaagagtt aagcgtaacg gggtttattc catacaacag
29341 aaaagagtgg ctgacgcagc ttttcaattt agctgaggca gaaacgggta aaggcgagca
29401 aacaaaatat cgggtatctt gtactgtggc tgaagccgtg aatatgcgcg aagtgcaatt
29461 tagtggagag gtatccgcaa ctgagcaaaa tgggcagttg gggtggtcga tttcatttag
29521 gttgcgtgaa gtcaattccg ttgccgagaa aaaagaccag cgaaagaaaa accaaaggt
29581 aaaaactcaa ggtgagaacg caccagtagc aaaaagtgca ggtgaaaatt cggggaaatc
29641 tggagaagaa aacaagtcgg acgaaagaaa aggcttggca aagatttag atgattggat
29701 tggttcataa atgaaaatta taaaaacatg cattattgat gatgaagaat tggaacttgc
29761 tgatgaactt atcgttttag aacttaataa tacggggcgt gggtttgtca cggttcgcac
29821 agataaagat tgtatcggca aagtgcagt ttttgagatg ggagaatatg agcactatta
29881 caaatggttt gacggtattg ttgagcgtga acaaagtgcg gaaaacggct ataaaaaatt
29941 attcattcgt gaaaaagtgg cagtatttga aagccgtta aattgctctc atcgtcatat
30001 tactttgcgt gatttgtgtg cttggataac aagccaaaca aaatccccg tcaaggtgcc
30061 gcaggcagat tatgcggata cgccgatttc gttgtttact cacaacggca gcggttatca
30121 gcttttagcc aatattgggc gacaatatca aatagcagat tatatgtggc aacaatcgcc
30181 agacggctct ttgtttgttg gttcgcataa agattcacgc tgggcaggta agaatattga
30241 atttgacgaa agcatgacat taacaagcgg cagcaatgat atgaccattc cgattactgc
30301 tgctattcga ccaggtgcga ttatcaatgg caataaaatt cagaaagtag aattgtctgg
30361 cgatgattat gtgctttcgt gggaaaattt aggcaaagat ggtaagccag aacaaaaaag
30421 cccagaacgc cgccaaatgg aaaaaacatt ccccgaactg gctggcggtt atcatttgcc
30481 gaagtatgct aaagttgttg gtatagcaga tccctcaagc ggcggcgata tttccgatcc
30541 gttccgacca aaatatgctg tcgagttgca actactggac gaaaacggaa acgaggataa
30601 aacggtgcca gtttacccag ctgtgccttt gcctgtaaca agtacaggtt cacaaggtgg
30661 ggatttgcc tttcctgaag tgggcacaat ggttgaagtc ggttttgctt atgggcgaag
30721 tgatcagcct tttgtacgca ctatgttagc acaaggaaaa acagtaccga gtgttgcacc
30781 tggagaacaa ctcaagcagc aacgcccga agtgtatgag cgcaccgatg ccgcaggcaa
30841 taagattcgc gaaaccgatc agaagattac agataaatcc tttaacgac acatcgaaac
30901 agatagtgaa gtaaaacaaa ttggtacatc gacaaaaaca gtagattcag atagtacgca
30961 aactataggc ggaaataaaa ctgttagcgt attgggtagt atcaatgaca cgactgcaag
31021 caatcgtact gtgggaactg gtgggcacgt gtgcacgtt acaagaaaaa atcgtgggac tagcgcaacg
31081 tgtttcggac gaaaagaata aatttgtggc accgctaagt tatataggaa cagaaagtca
31141 gaatatttt agattgttag aggacactat tcagctatta ggcgaagttg cgagtgcagt
31201 ggcaacgcat acgcatagag gatcgccacc gccagatcaa gcaagcacat tcaaccagca
31261 ggcaaacaaa gcaaaaacaa tcaaaagtaa actcacgcct atcattgagt aacaaccgca
31321 attcatatca aaccaaagcc gcacaatgtt gcggcttttc tttatgtttc cgacatgtat
31381 gtcggaaaca tcagccacgg aaaatctaag ttattgttat aacaaataaa tctacgtaat
31441 aagcaatata aaacaattcc acggaaattt ttcacgtaaa aacacaaggc acggaaaatc
31501 cacttcct
```

Figure 10H

| Primer | Sequence[a] | Target/use |
|---|---|---|
| 1 | GAGAC<u>GGATCC</u>GTTTGCACAACTACGGGCTTA | Cloning of the 5' terminus of HP2 upstream of *attP* (*Bam*HI) |
| 2 | GAGACCG<u>CTCGAG</u>CGGATGGCTTGCGGAAGTTTATG | Cloning of the 5' terminus of HP2 upstream of integrase (*Xho*I) |
| 3 | GAGAGGA<u>AGATCT</u>CCCGGTCAAAATCTACCCGAAA | 3' terminus of HP2 (*Bgl*II) |
| 4 | GAGACG<u>GAATTC</u>CGCTTTAGTTTGCTCCGCAACC | Cloning of the 3' terminus of HP2 at position 29,742 (*Eco*RI) |
| 5 | GCTGCTCTACCGACTGAGCTA | Creation of a PCR probe to the early genes of HP1 + HP2 |
| 6 | AGACGGTGAGGCACGTTTAG | Creation of a PCR probe to the early genes of HP1 + HP2 |
| 7 | AAGGGGGAAATAATGGCAAC | Cloning of HP2 genes in the pR promoter group |
| 8 | AAAGGATTGTTATTGCCCC | Cloning of HP2 genes in the pR promoter group |

[a] Sequences run 5' to 3', with restriction sites listed in target use underlined.

Figure 11

COMPOSITIONS AND METHODS TO MODULATE *H. INFLUENZAE* PATHOGENESIS

GOVERNMENTAL SUPPORT

This work was supported in part by grants from the NIH (AI49437). Consequently, the United States Government may have certain rights to this invention.

FIELD OF INVENTION

The present invention relates to the modulation of bacterial pathogenesis. In one embodiment, bacterial pathogenesis is reduced by administering a therapeutic compound. In one embodiment, the therapeutic compound includes, but is not limited to, a drug, protein, or nucleic acid. In one embodiment, the therapeutic compound modulates bacterial pathogenesis by modulating a gene related to an *H. influenzae* lipooligosaccharide-phosphorylcholine (LOS-PC) epitope display. In one embodiment, the gene comprises the CsrA gene. In one embodiment, the gene is related to a non-typeable *H. influenzae* LOS-PC epitope display.

BACKGROUND

*Haemophilus influenzae* (*H. influenzae*) is a gram-negative, facultative aerobe that colonizes the respiratory tract of humans, the only natural host known for this bacterium. It is a common cause of otitis media, upper and lower respiratory tract infections, septicemia, and meningitis in children. During the course of infection, *H. influenzae* is likely to encounter varying environmental conditions such as the relatively high oxygen environment of the airway surface to sites lower in oxygen such as an interstitial location during traversal of the mucosal epithelium, entry into bloodstream, or spread to the middle ear.

Putative genes known to play a role in bacterial pathogenesis may include sodA (superoxide dismutase), lctP (L-lactate permease), and lpdA (dihydrolipoamide dehydrogenase), whose respective homologues in *E. coli* have been shown to be responsive to redox conditions. Compan et al. (1993); Lynch et al. (1996); and Cunningham et al. (1998). In infant rat models of *H. influenzae* infection, sodA was shown to be important for oxidative stress defense and for optimal nasopharyngeal colonization. D'Mello et al. (1997). Another enzyme, lctP, is required for *H. influenzae* survival in the bloodstream. Herbert et al. (2002). Further, lpdA, a component of the pyruvate and a-ketoglutarate dehydrogenases, is needed for aerobic growth in vitro and for bacteremia. Herbert et al. (2003).

*H. influenzae* virulence may result from gene expression modulation in response to environmental redox growth conditions as it transits between microenvironments within the host. What is needed are compositions and methods to reduce or eliminate the genetically directed colonization and pathogenesis of *H. influenzae* without affecting host cells.

SUMMARY OF THE INVENTION

The present invention relates to the modulation of bacterial pathogenesis. In one embodiment, bacterial pathogenesis is reduced by administering a therapeutic compound. In one embodiment, the therapeutic compound includes, but is not limited to, a drug, protein, or nucleic acid. In one embodiment, the therapeutic compound modulates bacterial pathogenesis by modulating a gene related to *H. influenzae* lipooligosaccharide-phosphorylcholine (LOS-PC) epitope display. In one embodiment, the gene comprises the CsrA gene. In one embodiment, the gene is related to a nontypeable *H. influenzae* LOS-PC epitope display.

In one embodiment, the present invention contemplates a method, comprising a) providing i) an oligonucleotide at least partially complementary to a portion of the coding region of the CsrA gene of *H. influenzae*; and ii) one or more *H. influenzae* cells comprising a CsrA gene; and b) administering said oligonucleotide to said one or more cells under conditions such that expression of said CsrA gene is reduced. In one embodiment, the one or more cells are in culture medium. In one embodiment, the one or more cells are in a host animal. In one embodiment, the host animal is a human. In one embodiment, the oligonucleotide is administered to said human at a dosage of between 0.01 µg to 100 g per kg of body weight. In one embodiment, the oligonucleotide is administered to said human at a dosage of between 1 mg to 500 mg per kg of body weight. In one embodiment, the oligonucleotide is administered to said human at a dosage of between 6 mg to 30 mg per kg of body weight. In one embodiment, the oligonucleotide is administered to said human once per day. In one embodiment, the oligonucleotide is administered to said human two or more times per day. In one embodiment, the oligonucleotide is administered to said human continuously. In one embodiment, the oligonucleotide is administered to said human continuously for a period of between 2 hours and 2 weeks. In one embodiment, the oligonucleotide is administered to said human continuously for a period of between 1 day and 1 week. In one embodiment, the oligonucleotide is completely complementary to said portion of said coding region. In one embodiment, the oligonucleotide is between 15 and 30 bases in length.

In one embodiment, the present invention contemplates a method, comprising a) providing i) an oligonucleotide at least partially complementary to a portion of the coding region of the CsrA gene of *H. influenzae*; and ii) one or more *H. influenzae* cells comprising a CsrA gene, said cells capable of expressing a phosphorylcholine epitope; and b) administering said oligonucleotide to said one or more cells under conditions such that expression of said phosphorylcholine epitope is increased. In one embodiment, the one or more cells are in culture medium. In one embodiment, the one or more cells are in a host animal. In one embodiment, the host animal is a human. In one embodiment, the oligonucleotide is administered to said human at a dosage of between 0.01 µg to 100 g per kg of body weight. In one embodiment, the oligonucleotide is administered to said human at a dosage of between 1 mg to 500 mg per kg of body weight. In one embodiment, the oligonucleotide is administered to said human at a dosage of between 6 mg to 30 mg per kg of body weight. In one embodiment, the oligonucleotide is administered to said human once per day. In one embodiment, the oligonucleotide is administered to said human two or more times per day. In one embodiment, the oligonucleotide is administered to said human continuously. In one embodiment, the oligonucleotide is administered to said human continuously for a period of between 2 hours and 2 weeks. In one embodiment, the oligonucleotide is administered to said human continuously for a period of between 1 day and 1 week. In one embodiment, the oligonucleotide is completely complementary to said portion of said coding region. In one embodiment, the oligonucleotide is between 15 and 30 bases in length.

In one embodiment, the present invention contemplates a method, comprising a) providing i) an oligonucleotide at least partially complementary to a portion of the promoter of the CsrA gene of *H. influenzae*; and ii) one or more *H. influenzae* cells comprising a CsrA gene; and c) administering said oligonucleotide to said one or more cells under conditions such that expression of said CsrA gene is reduced. In one embodiment, the one or more cells are in culture medium. In one embodiment, the one or more cells are in a host animal. In one embodiment, the host animal is a human. In one embodiment, the oligonucleotide is administered to said human at a dosage of between 0.01 µg to 100 g per kg of body weight. In one embodiment, the oligonucleotide is administered to said human at a dosage of between 1 mg to 500 mg per kg of body weight. In one embodiment, the oligonucleotide is administered to said human at a dosage of between 6 mg to 30 mg per kg of body weight. In one embodiment, the oligonucleotide is administered to said human once per day. In one embodiment, the oligonucleotide is administered to said human two or more times per day. In one embodiment, the oligonucleotide is administered to said human continuously. In one embodiment, the oligonucleotide is administered to said human continuously for a period of between 2 hours and 2 weeks. In one embodiment, the oligonucleotide is administered to said human continuously for a period of between 1 day and 1 week. In one embodiment, the oligonucleotide is completely complementary to said portion of said promoter. In one embodiment, the oligonucleotide is between 15 and 30 bases in length.

In one embodiment, the present invention contemplates a method, comprising a) providing i) an oligonucleotide at least partially complementary to a portion of the promoter of the CsrA gene of *H. influenzae*; and ii) one or more *H. influenzae* cells comprising a CsrA gene, said cells capable of expressing a phosphorylcholine epitope; and b) administering said oligonucleotide to said one or more cells under conditions such that expression of said phosphorylcholine epitope is increased. In one embodiment, the one or more cells are in culture medium. In one embodiment, the one or more cells are in a host animal. In one embodiment, the host animal is a human. In one embodiment, the oligonucleotide is administered to said human at a dosage of between 0.01 µg to 100 g per kg of body weight. In one embodiment, the oligonucleotide is administered to said human at a dosage of between 1 mg to 500 mg per kg of body weight. In one embodiment, the oligonucleotide is administered to said human at a dosage of between 6 mg to 30 mg per kg of body weight. In one embodiment, the oligonucleotide is administered to said human once per day. In one embodiment, the oligonucleotide is administered to said human two or more times per day. In one embodiment, the oligonucleotide is administered to said human continuously. In one embodiment, the oligonucleotide is administered to said human continuously for a period of between 2 hours and 2 weeks. In one embodiment, the oligonucleotide is administered to said human continuously for a period of between 1 day and 1 week. In one embodiment, the oligonucleotide is completely complementary to said portion of said promoter. In one embodiment, the oligonucleotide is between 15 and 30 bases in length.

In one embodiment, the present invention contemplates a composition comprising a bacteriophage capable of becoming incorporated into a *H. influenzae* bacterial cell, wherein said bacteriophage comprises a conjugated therapeutic compound. In one embodiment, the bacteriophage is selected from the group consisting of H1, H2, and S. In one embodiment, the therapeutic compound comprises a nucleic acid. In one embodiment, the nucleic acid comprises antisense mRNA. In one embodiment, the nucleic acid comprises sense mRNA. In one embodiment, the antisense mRNA hybridizes to the sense mRNA. In one embodiment, the sense mRNA encodes a CsrA protein. In one embodiment, the therapeutic compound comprises a protein. In one embodiment, the protein is encoded by a *H. influenzae* CsrA gene. In one embodiment, the protein is encoded by a homologue of said CsrA gene. In one embodiment, the therapeutic compound comprises a drug.

In one embodiment, the present invention contemplates a method, comprising: a) providing; i) a host having at least one symptom of a *H. influenzae* infection; ii) a composition comprising a therapeutic compound; and b) administering said composition to said host, wherein said symptom is reduced. In one embodiment, the method further comprises step (c) exposing said *H. influenzae* to an aerobic redox growth condition. In one embodiment, the composition further comprises a bacteriophage capable of becoming incorporated into a *H. influenzae* bacterial cell, wherein said bacteriophage is conjugated to said therapeutic compound. In one embodiment, the bacteriophage is selected from the group consisting of H1, H2, and S. In one embodiment, the therapeutic compound comprises a nucleic acid. In one embodiment, the nucleic acid comprises antisense mRNA. In one embodiment, the nucleic acid comprises sense mRNA. In one embodiment, the antisense mRNA hybridizes to the sense mRNA. In one embodiment, the sense mRNA encodes a CsrA protein. In one embodiment, the compound comprises a protein. In one embodiment, the protein is encoded by a *H. influenzae* CsrA gene. In one embodiment, the protein is encoded by a homologue of said CsrA gene. In one embodiment, the therapeutic compound comprises a drug.

In one embodiment, the present invention contemplates a method, comprising: a) providing; i) a host at risk for *H. influenzae* pathogenesis; ii) a composition comprising a therapeutic compound; and b) administering said composition to said host, wherein said risk for pathogenesis is reduced. In one embodiment, the method further comprises step (c) exposing said host to an aerobic redox growth condition. In one embodiment, the composition further comprises a bacteriophage capable of becoming incorporated into an *H. influenzae* bacterial cell, wherein said bacteriophage is conjugated to said therapeutic compound. In one embodiment, the bacteriophage is selected from the group consisting of H1, H2, and S. In one embodiment, the therapeutic compound comprises a nucleic acid. In one embodiment, the nucleic acid comprises antisense mRNA. In one embodiment, the nucleic acid comprises sense mRNA protein In one embodiment, the antisense mRNA hybridizes to the sense mRNA. In one embodiment, the sense mRNA encodes a CsrA. In one embodiment, the compound comprises a protein. In one embodiment, the protein is encoded by a *H. influenzae* CsrA gene. In one embodiment, the protein is encoded by a homologue of said CsrA gene. In one embodiment, the therapeutic compound comprises a drug.

DEFINITIONS

The term "LOS-PC epitope display" as used herein, refers to a membrane-bound complex comprising lipooligosaccharide-phosphorylcholine. The "LOS-PC epitope display" may provide a bacterium (i.e., for example, non-typeable *H. influenzae*, *H. influenzae* Rd, or modified strains thereof) with the ability to attach and colonize host tissue. The "LOS-PC epitope display" may also provide host immune defense recognition sites.

The term "TEPC-15" as used herein, refers to a specific monoclonal antibody having specificity for the LOS-PC epitope display.

The term "therapeutic compound" as used herein, refers to any pharmacologically active substance capable of being administered which achieves a desired clinical effect. Therapeutic compounds can include, but are not limited to, synthetic or naturally-occurring, drugs, hormones, proteins or peptides, nucleic acids, oligonucleotides or nucleotides, polysaccharides or sugars.

The terms "bacteriophage" and "phage", as used herein refer to a virus which can infect a bacterial strain or a number of different bacterial strains.

The term "incorporated into", as used herein refer to any process by which a nucleic acid sequence become part of the genome of a bacterial cell. Such a nucleic acid incorporation may result in a functional exon operably linked to a promoter such that transcription of the nucleic acid may occur under the proper inducing conditions.

The term "linker moiety" as used herein, refers to any molecule attached to a cell membrane binding site (i.e., for example, a LOS-PC epitope) that improves the binding capability of the membrane binding site. The linker moiety may change the binding capabilities by, for example, minimizing steric hindering or improving ionic strengths, etc.

The term "targeted" as used herein, refers to a molecular structure that provides a specific affinity for a particular cell type.

The term "protein" as used herein, refers to any molecular polymer comprising amino acids linked by covalent peptide bonds.

The term "CsrA gene" as used herein, refers to a specific genome locus that encodes a post-transcriptional repressor protein having an effect on carbon storage regulation. The genome locus may comprise *H. influenzae* genes including, but not limited to, a wild-type (i.e., for example, non-typeable *H. influenzae*), deletion or insertion mutants (i.e., for example, DCsrA from the strain 8Dkan as depicted in FIGS. 6 & 7 or the Drep mutant as depicted in FIGS. 3 & 4 etc) and the like.

The term "encoded by" as used herein, refers to the nucleotide sequence of any particular gene, that when transcribed and translated, results in a protein or peptide of a particular sequence.

The term "homologue" as used herein, defined as a gene or protein having a nucleic acid or amino acid sequence similar to a wild-type gene or protein. The homologue may comprise: i) regions of identity with the wild-type gene or protein, and ii) regions of non-identity with the wild-type gene or protein.

The term "gene" as used herein, refers to any nucleotide sequence comprising an open reading frame, promoter, a start codon, and a stop codon. Upon activation of the promoter, the gene functions to produce messenger RNA (mRNA) based upon the sequence of the open reading frame.

The term "wild-type" as used herein, refers to any gene or protein that represents a predominant naturally-occurring nucleic acid or amino acid sequence.

The term "mutant" or "mutation" as used herein, refers to any change in a nucleotide or amino acid sequence when compared to the wild-type sequence. Mutation include, but are not limited to, insertions, deletions, transpositions, substitutions (i.e., for example, a replacement), single point mutations (i.e., for example, one nucleic acid or amino acid). The present invention includes within this definition a "silent mutation" wherein a nucleic acid sequence change does not alter the translated protein amino acid sequence. A mutation may, however, be conservative, where the nucleic acid sequence does alter the translated protein amino acid sequence but does not substantially alter the protein's functionality. Conservative substitutions may occur within specified groups of amino acids and include, but are not limited to; i) glycine, alanine, valine, isoleucine, leucine; ii) aspartic acid, glutamic acid; iii) asparagine, glutamine; iv) serine, threonine; iv) lysine, arginine; and v) phenylalanine, tyrosine.

The term "oligonucleotide" as used herein, refers to any polymer molecule comprising nucleotide bases attached by phosphodiester covalent bonds. It should be understood that this term is essentially equivalent to "nucleic acid" or "nucleotides" or the like.

The term "mRNA" as used herein, refers to a ribonucleic acid resulting from gene transcription comprising the nucleic acid uracil.

The term "monocistronic" as used herein, refers to any nucleic acid encoding a single open reading frame such that it is translated into a single protein or peptide.

The term "multicistronic" as used herein, refers to any nucleic acid encoding multiple open reading frames such the it is translated into multiple proteins or peptides.

The term "repressor protein" as used herein, refers to any protein that binds to a gene such that transcription is reduced.

The term "post-transcriptional regulator protein" as used herein, refers to any protein that binds to a gene such that transcription is modulated.

The term "CsrA" as used herein, refers to a gene that produces a repressor protein affecting the central carbohydrate metabolism pathway (i.e., for example, galU).

The term "operon" as used herein, refers to an operably-linked genetic complex of closely linked genes that produces a single messenger RNA molecule in transcription and that consists of structural genes and regulating elements (as an operator and promoter) that participate in a common biochemical pathway (i.e., for example, the lid operon comprising genes licA, licB, licC, and licD).

The term "upregulate", "upregulating", or "upregulated" as used herein, refers to any alteration in gene activity such that mRNA transcript expression is increased with a concomitant increase in translated protein.

The term "downregulate", "downregulating", or "downregulated" as used herein, refers to any alteration in gene activity such that mRNA transcript expression is deceased with a concomitant decrease in translated protein.

The term "expression" as used herein, refers to the production of newly formed mRNA (i.e., for example, transcription) or newly formed protein (i.e., for example, translation) that results from gene activity. Expression may occur in vivo or in vitro.

The term "transcript" as used herein, refers to any nucleic acid comprising mRNA that ultimately acts either as a ribosomal substrate or a gene regulator.

The term "sense mRNA" as used herein, refers to any mRNA whose nucleic acid sequence is complementary to a DNA sequence.

The term "coding region" as used herein, refers to any region of an oligonucleotide, that when transcribed, generates an mRNA that may be subsequently translated into a functional polypeptide or protein.

The term "promoter region" as used herein, refers to any region of an oligonucleotide that regulates transcription of a coding region (i.e., for example, an xylA promoter as depicted in FIG. 9).

The term "antisense nucleic acid" as used herein, refers to any nucleic acid, regardless of length, that is complementary to a coding strand or mRNA of interest. The antisense molecule may inhibit the expression of only one nucleic acid, or, the antisense molecule may inhibit the expression of more than one nucleic acid. Desirably, the antisense nucleic acid decreases the expression or biological activity of a nucleic and or encoded protein by at least 20, 40, 50, 60, 70, 80, 90, 95, or 100%. Any antisense molecule can be administered (i.e., for example, to an individual cell or to whole animals) by various methods including, but not limited to, systemically via the bloodstream, locally via percutaneous injection or transdermal patch, intraperitoneally, surgical implantation devices (i.e., for example, polymeric sheet matrices, bandages, gels, foams etc.), rectal, intranasal etc. Desirably, a region of the antisense nucleic acid or the entire antisense nucleic acid is at least 70, 80, 90, 95, 98, or 100% complimentary to a coding sequence, regulatory region (5' or 3' untranslated region), or an mRNA of interest. Desirably, the region of complementarity includes at least 5, 10, 20, 30, 50, 75, 100, 200, 500, 1000, 2000 or 5000 nucleotides or includes all of the nucleotides in the antisense nucleic acid.

The term "antisense mRNA" as used herein, refers to any mRNA whose nucleic acid sequence is homologous to a DNA sequence and complementary to a sense mRNA sequence.

The term "hybridize" or "hybridization" as used herein, refers to any pairing of complementary nucleic acids. Hybridization and the strength of hybridization (i.e., the strength of the association between the nucleic acids) is impacted by such factors as the degree of complementary between the nucleic acids, stringency of the conditions involved, the Tm of the formed hybrid, and the G:C ratio within the nucleic acids.

The term "complementary" or "complementarity" refers to any polynucleotides (i.e., for example, a sequence of nucleotides such as an oligonucleotide or a target nucleic acid) that are related by the base-pairing rules. For example, for the sequence "A-G-T," is complementary to the sequence "T-C-A.". Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "stringency", as used herein, refers to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required when it is desired that nucleic acids which are not completely complementary to one another be hybridized or annealed together.

The term "primer", as used herein, refers to an oligonucleotide which is capable of acting as a point of initiation of synthesis when placed under conditions in which primer extension is initiated. An oligonucleotide "primer" may occur naturally, as in a purified restriction digest or may be produced synthetically. A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "host" as used herein, refers to any organism capable of becoming infected by $H.$ $influenzae$ or any strain or mutation thereof. A host may include, but is not limited to, chinchillas, mice, rats, rabbits, guinea pigs, or humans.

The term "infection" as used herein, refers to any condition where a bacterium (i.e., for example, non-typeable $H.$ $influenzae$ or a strain or mutation thereof) has attached to, and colonized, living tissue such that the bacterium grows, divides, and increases the physical area of colonization.

The term "symptom" as used herein, refers to any observable clinical parameter used in the diagnosis and treatment of a disease or sickness.

The term "risk factors" as used herein, refers to any physical or mental condition that predisposes a host to infection. Risk factors may include, but are not limited to, health status, psychological status (i.e., for example, stress), social status (i.e., for example, low socioeconomic status), living environment, age, or sex.

The term "administering" as used herein, refers to any method of providing a therapeutic compound to a host such that the therapeutic compound has its intended effect on the host. Administering may be performed by methods including, but not limited to, oral, transdermal, injection (i.e., for example, parenteral), rectal, nasal, or topical.

The term "symptom is reduced" as used herein, refers to any therapeutic treatment (i.e., for example, following administration of a therapeutic compound) whereby the clinical condition of the subject is improved but not completely eliminated. Where a symptom is said to be "reduced" it is indicated that the degree of such symptom (such as the degree of nausea or the amount of tissue infection) is diminished. The present invention is not limited to any particular quantitative level.

The term "aerobic redox growth condition" as used herein, refers to any environmental condition that results in an oxygenation level comparable to a bacterial suspension having a volume of approximately 5-150 ml, preferably 20-100 ml, and more preferably 50-75 ml incubated in a 500 ml Erlenmeyer flask exposed to standard cell culture aeration.

The term "microaerobic redox growth condition" as used herein, refers to any environmental condition that results in an oxygenation level comparable to a bacterial suspension having a volume of approximately 175-350 ml, preferably 200-300 ml, and more preferably 250-275 ml incubated in a 500 ml Erlenmeyer flask exposed to standard cell culture aeration.

The term "at risk for" as used herein, means any segment of the world population that has an increased risk for bacterial pathogenesis or infection (i.e., non-typeable $H.$ $influenzae$ and strains and mutations thereof). $H.$ $influenzae$ infection is most commonly found in children, but can occur at any age. Risk factors for $H.$ $influenzae$ include, but are not limited to, a recent history of otitis media (ear infection), sinusitis (infection of sinuses), pharyngitis (sore throat), or other upper respiratory infection or a history of a family members with an $H.$ $influenzae$ infection. Another significant risk factor includes race, wherein Native Americans are noted as susceptible.

The term "pathogenesis" as used herein, refers to any process regarding the origination and development of a disease (i.e., for example, non-typeable $H.$ $influenzae$ infection and strains and mutations thereof).

The term "bacterial virulence" as used herein, refers to the quality or state of infectivity. The virulence of a disease is also related to the relative capacity of a pathogen to overcome host defenses.

The term "colonization" as used herein, refers to bacterial attachment to host tissue as a precondition to infection.

The term "bacterial attachment" as used herein, refers to any stable contact between a bacterium's outer membrane and host tissue as a prelude to colonization and infection. Such contact may include, but is not limited to, adhesin glycoproteins, pili or fibre impregnation.

The term "modulate", "modulation", "modulating", "regulate, "regulation", or "regulating" as used herein, refers an alteration of the activity of a biochemical pathway or enzyme by an independent compound. Such a compound may include, but is not limited to, a drug, hormone, protein, nucleic acid, or an ion.

The term "phase variation" as used herein, refers to temporal alterations in protein and nucleic acid expression in a particular species or strain.

The term "biosynthesis" or "biosynthetic pathway" as used herein, refers to any process that creates an organic compound using components produced by a living organism. A component may reside either in vitro or in vivo and may include, but not limited to, enzymes, proteins, nucleic acids, cofactors, or substrates. In some instances, the components may be physically linked or designed to function in succession, wherein the product of one component is used as a substrate of another component.

The term "attaching" or "conjugating" as used herein, refers to the addition of one compound to another by molecular forces including, but not limited to, covalent bonding, ionic bonding, hydrophobic bonding, Van der Waals forces, or friction.

The term "central carbohydrate metabolism" as used herein, refers to the integrated anabolic and catabolic biochemical pathways used to process sugar molecule in a living organism.

The term "formulation" as used herein, refers to any pharmaceutical composition comprising at least one active ingredient along with other optional ingredients useful in, for example, binding, flavoring, coloring, preserving, stabilizing, increasing shelf life, adding structural rigidity, adding desired mouth feel, adding desired mouth consistency, aiding in regulating dissolution rate, adjusting the pH of the local environment or adding adhesive qualities to promote absorption into the systemic circulation.

The term "pharmaceutically acceptable" as used herein, refers to any physiologically compatible compound including, for example, carbohydrates, such as glucose, sucrose, or dextrans, antioxidants, such as ascorbic acid or glutathione, chelating agents, low and/or high molecular weight proteins, or excipients or other stabilizers and/or buffers. Other physiologically acceptable compounds include wetting agents, emulsifying agents, dispersing agents or preservatives which are particularly useful for preventing the growth or action of microorganisms pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. Pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

The term "injection" as used herein, refers to any administration of a therapeutic compound to a host involving delivery directly to the host internal tissues. Such injection may include, but is not limited to, intravenous, intraperitoneal, or intramuscular.

The term "parenteral" as used herein, refers to any administration of a therapeutic compound to a host that does not involve the intestines. Parenteral includes but is not limited to, injection, transdermal, intranasal, and the like.

The term "hydrogen-bonding site" as used herein, refers to any functional group which can be either a proton acceptor or a proton donor. Examples of such functional groups include but are not limited to hydroxyl group, amino group, amide group, ketone, carbonyl group, urethane bond, and halogen group.

The term "molecule having hydrogen-bonding sites" as used herein, refers to any molecule which has such a functional group or groups comprising "hydrogen-bonding sites", thus making it possible to bind the polymer to other molecules (i.e., for example, a nucleic acid) through hydrogen bonds.

BRIEF DESCRIPTION OF THE FIGURES

FIG. 4A presents exemplary data showing quantitation of licA mRNA transcription driven by the recombinant hel promoter from the Drep (open bars) and Rhel-licA strains (crosshatched bars) under aerobic (+O2) and microaerobic (M) redox growth conditions. Y axis: Fold induction values.

FIG. 4B presents an exemplary Western blot of whole-cell lysates from aerobic (+O2) and microaerobic (M) cultures showing PC epitope display by immunoblotting with anti-PC mAb. Lysates are from strains Drep (lanes 1 and 3) and Rhel-licA (lanes 2 and 4). Fold induction of licA expression from Drep and Rhel-licA is shown below each lane.

FIG. 8A presents one embodiment of a CsrA coding region nucleic acid sequence (SEQ ID NO:1).

FIG. 8B presents one embodiment of a CsrA coding amino acid sequence (SEQ ID NO:2).

FIG. 9 (SEQ ID NO:12) presents one embodiment of a D-xylose inducible xylA promoter sequence capable of expressing the CsrA coding region. The sequence is 205 base pairs generated using a SpeI-BamHI fragment from pXT10.

FIG. 10A-H presents one embodiment of an H2 bacteriophage nucleic acid sequence (SEQ ID NO:3).

FIG. 11 presents representative primers (Primer 1: SEQ ID NO:4; Primer 2: SEQ ID NO:5; Primer 3: SEQ ID NO:6; Primer 4: SEQ ID NO:7; Primer 5: SEQ ID NO:8; Primer 6: SEQ ID NO:9; Primer 7: SEQ ID NO:10; Primer 8: SEQ ID NO:11) used in the construction of bacteriophage plasmids (i.e., for example, an H2 phage)

DETAILED DESCRIPTION OF THE INVENTION

Figure 1:
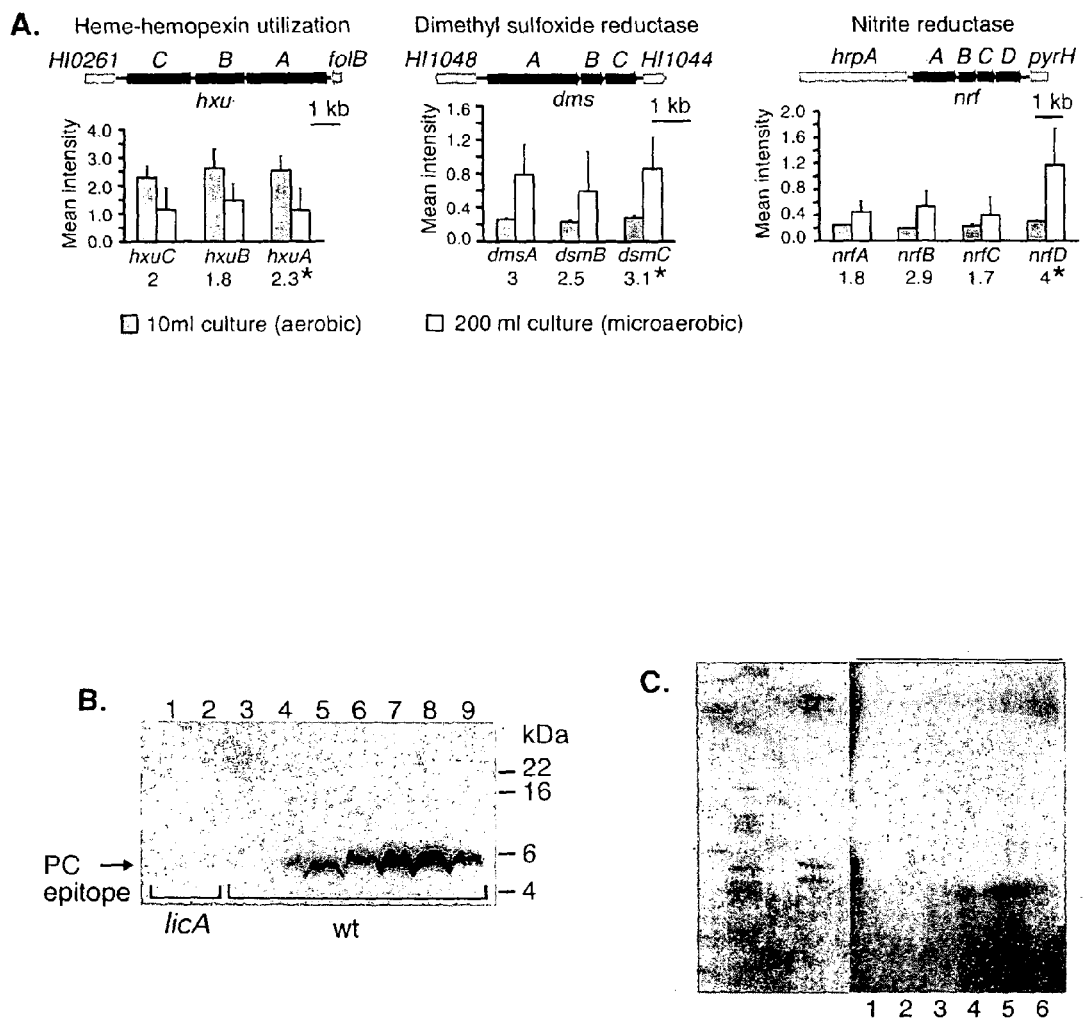
FIG. 1A shows exemplary data regarding differential expression of heme-hemopexin hxuCBA (HI0262-HI0264), dimethylsulfoxide reductase dmsABC (HI1047-HI1045), and nitrite reductase nrfABCD (HI1069-HI1066) putative operons of H. influenzae when grown under various redox growth conditions. Each bar represents the signal mean intensity (y-axis) from 3 independent microarray experiments quantifying the expression level of a gene (x-axis) within each respective operon from cultures grown aerobically (crosshatched bars) and microaerobically (open bars). The fold induction is indicated underneath each gene. Asterisks represent induction ratios with p values≦0.01.
FIG. 1B shows an exemplary Western blot of whole-cell lysates from H. influenzae Rd (wt, lanes 3-9) or strain RlicA41 (licA, lanes 1 & 2) grown in a 500 ml flask under conditions of varied culture aeration. Lane 1: 10 ml; Lane 2: 100 ml; Lane 3: 10 ml; Lane 4; 20 ml; Lane 5: 60 ml; Lane 6: 100 ml; Lane 7: 200 ml; Lane 8: 300 ml; Lane 9: unaerated. Each sample was separated by SDS-18% PAGE and immunoblotted with anti-PC mAb TEPC-15 (an antibody specific for the LOS-PC epitope).
FIG. 1C shows one embodiment of a transcriptional start site of a licA gene. The right-hand gel section shows an exemplary primer extension analysis was performed using total RNA from wild-type H. influenzae Rd cultures grown under conditions of varied culture aeration: 10 ml (Lane 1); 20 ml (Lane 2); 60 ml (Lane 3); 100 ml (Lane 4); 200 ml (Lane 5), and unaerated (Lane 6). The left-hand gel section shows an exemplary sequence ladder. The licA transcription start site is indicated by the arrow at the +1 position. The nucleotide sequence of the 5' region of licA is shown below and three potential licA ATG initiation start codons α, β, and γ are underlined. (Weiser et al., 1998). A licA transcriptional start site is indicated by the arrow at the +1 position. A putative— 10 RNA polymerase promoter consensus site is underlined.

The present invention relates to the modulation of bacterial pathogenesis. In one embodiment, bacterial pathogenesis is reduced by administering a therapeutic compound. In one embodiment, the therapeutic compound includes, but is not limited to, a drug, protein, or nucleic acid. In one embodiment, the therapeutic compound modulates bacterial pathogenesis by modulating a gene related to $H.$ $influenzae$ lipooligosaccharide-phosphorylcholine (LOS-PC) epitope display. In one embodiment, the gene comprises the CsrA gene. In one embodiment, the gene is related to a non-typeable $H.$ $influenzae$ LOS-PC epitope display.

An underexploited avenue of research is that of identifying factors essential for the pathogenesis of a pathogen and developing counteractive therapeutic compounds. The vast majority of currently available antibiotics inhibit bacterial targets involved in one of five cellular functions: i) cell wall synthesis; ii) protein synthesis; iii) DNA replication; iv) RNA polymerase; and v) a metabolic pathway. One significant drawback to this traditional approach has always been that many bacterial cellular functions are also present in mammalian cells. Clearly, the notion of targeting a factor involved in bacterial pathogenesis (i.e., for example, infectivity and/or virulence) is a departure from these traditional targets.

Bacterial pathogenesis depends upon a multitude of events, most of which are dynamic in nature. For example, pathogens that replicate inside host cells: i) recognize their target host cell; ii) gain entry into a target host cell; iii) either block phagosome-lysosome fusion, resist lysosomal contents, or escape into the cytoplasm; iv) scavenge nutrients in order to replicate; v) produce toxins (or avoid producing toxins) so as not to alert the host to the developing infection; and vi) identify a pathway to infect another host cell in order to spread the infection.

Pathogenesis factors may, therefore, comprise any bacterial function that effects one of the above events. Cell surface membrane binding sites (i.e., for example, epitopes) have first contact with host tissue and/or host cells. One such epitope is the lipooligosaccharide-phosphorylcholine epitope (LOS-PC).

I. Lipooligosaccharide-Phosphorylcholine Epitope (LOS-PC)

Lipooligosaccharide (LOS) is believed a component of a bacterium's outer-membrane and mediates interactions between the bacterium and the host's immune system. Many studies have suggested that LOS contributes to bacterial pathogenesis (i.e., for example, host cell infection). Specifically, in $H.$ $influenzae$, LOS lacks a long repetitive polysaccharide O-antigen side chain known to be present in gram negative bacteria lipopolysaccharide (LPS). Moxon et al. (2000). The LOS structure varies among strains, particularly among acapsular or non-typeable strains that are believed pathogens in otitis media or respiratory infections. $H.$ $influenzae$ LOS is known to have a structure comprising; i) Lipid A, an inner core comprised of several sugars including a single 3-deoxy-D-manno-octulonsonic acid (KDO) linked to three heptoses (i.e., heptose I, heptose II, and heptose III), and ii) an outer core containing a glucose-galactose heteropolymer that generally does not exceed six residues and may be modified with sialic acid, N-acetylgalactosamine, or phosphorylcholine (PC). Hood et al. (1999); and Risberg et al. (1999).

LOS expression has been shown to contribute to *H. influenzae*'s ability to establish an infection in the host (i.e., for example, pathogenic bacterial virulence). It is also known that LOS side chain derivatization is common in virulent strains. For example, *H. influenzae* having a sialylated-LOS is known to result in middle ear and nasopharynx colonization in a chinchilla model of otitis media. Bouchet et al. (2003). Conversely, bacterial mutants deficient in N-acetylgalactosamine-LOS exhibit reduced lethality in a mouse model. Hood et al. (1996b). *H. influenzae* having LOS-PC is known to mediate respiratory tract colonization and persistence in an infant rat model. Weiser et al. (1998). *H. influenzae* is also known to induce mucosal hyperplasia in an in vitro rat otitis media model. Placios et al., "Role of p38 Mitogen-Activated Protein Kinase In Middle Ear Mucosa Hyperplasia During Bacterial Otitis Media" *Infect Immun* 72:4662-4667 (2004). Other animal models capable of *H. influenzae* infection include, but are not limited to, guinea pig and rabbit. Folkerts et al. "Induction Of Guinea Pig Respiratory Airway Hypersensitivity By *Haemophilus Influenzae*: Role Of Histaminergic And Cholinergic Receptor Systems" *Agents Actions* 17:399-400 (1986); and Schneerson et al., "Age-Related Susceptibility To *Haemophilus Influenzae* Type b Disease In Rabbits" *Infect Immun* 4:397-401 (1971).

One embodiment of the present invention contemplates that *H. influenzae* LOS-PC epitope display plays a role in bacterial pathogenesis wherein an increase in LOS-PC epitope display enhances the host's ability to recognize the pathogen. In one embodiment, the present invention contemplates preventing pathogenesis or treating an ongoing infection by administering a therapeutic compound under conditions such that LOS-PC epitope display is increased. In one embodiment, the therapeutic compound comprises an oligonucleotide. In one embodiment, the oligonucleotide comprises a CsrA antisense nucleic acid sequence.

One embodiment of the present invention contemplates that *H. influenzae* LOS-PC epitope display plays a role in bacterial pathogenesis wherein an increase in LOS-PC epitope display promotes recognition by preparations comprising therapeutic compounds. In one embodiment, LOS-PC display is promoted by administration of an oligonucleotide. In one embodiment, the oligonucleotide acid comprises a CsrA sense nucleic acid sequence.

In one embodiment, an increased LOS-PC epitope display triggers at least one host defense mechanism. In one embodiment, an increased LOS-PC epitope display increases a pathogen's susceptibility to serum killing mediated by complement and the acute-phase reactant, C-reactive protein. Weiser et al. (1998). In one embodiment, an increased LOS-PC epitope display enhances human epithelial cell adherence and invasion by binding to the platelet-activating factor receptor, leading to possible sequestration by host immune clearance activity. Swords et al. (2000). In one embodiment, an increased LOS-PC epitope display in *Haemophilus*, and in other bacteria, are recognized by natural antibodies. Leon et al. (1971); and Shaw et al. (2000). Although it is not necessary to understand the mechanism of an invention, it is believed that a rapid switching off of LOS-PC epitope display is likely to provide an adaptive survival mechanism.

Some embodiments contemplated by the present invention comprise a biochemical model in which multiple metabolic pathways interact including, but not limited to, *H. influenzae* central carbohydrate metabolism genes and LOS biosynthesis genes both of which respond to redox growth conditions and modulate LOS-PC epitope display. It is believed that bacterial LOS-PC epitope display is modulated in response to signals that could play a role in rapid adaptation to environmental and physiological conditions encountered during infection. Redox growth condition regulation might provide a mechanism complementary to phase variation (i.e., a programmed change in gene expression during a pathogen's life cycle) for inactivating epitope production under unfavorable conditions. For example, bacterial attachment to a mucosal surface is more likely under an aerobic condition in which very low numbers of bacteria must avoid host innate immune defenses (i.e., for example, PC reactive antibodies). Conley et al. (1984). Subsequently, *H. influenzae* is thought to grow on the mucosal surface and form microcolonies or biofilms. Ehrlich et al. (2002). Notably, in vitro comparisons between plate-grown and biofilm model system bacteria indicate numerous antigenic modulation including, but not limited to, sialic acid residues, a LOS core epitope, and KDO. Campagnari et al. (1990; Murphy et al. (2002); and Greiner et al. (2004).

Most chronic infections (i.e., for example, human infections) involve bacteria in a sessile state known as a biofilm. These higher-ordered, elaborate structures comprise bacteria attached to a surface and enveloped in a polysaccharide matrix complete with aqueous channels. Donlan et al., "Biofilms: Survival Mechanisms of Clinically Relevant Microorganisms" *Clin Microbiol. Rev* 15(2):167-193 (2002); and Dunne W., "Bacterial Adhesion: Seen Any Good Biofilms Lately?" *Clin Microbiol Rev* 15(2):155-166 (2002). Biofilms can form on any surface and they have been implicated in infections including, but not limited to, endocarditis, cystic fibrosis, and otitis media. Costerton et al., "Bacterial Biofilms: A Common Cause Of Persistent Infections" *Science* 284:1318-1322 (1999); and Ehrlich et al., "Mucosal Biofilm Formation On Middle-Ear Mucosa In the Chinchilla Model Of Otitis Media" *J Am Med Assoc* 287(13):1710-1715 (2002). Bacterial biofilms are particularly challenging infections to treat because they are often resistant to antibiotics and are believed in a metabolically inactive state, so as to be at least transiently resistant to most antibiotics. Davies D., "Understanding Biofilm Resistance To Antibacterial Agents" *Nature Reviews Drug Discovery* 2:114-122 (2003).

Examples of bacterial pathogens capable of forming biofilms in vivo include, but are not limited to, *P. aeruginosa, S. aureus, Staph. epidermidis, V. parahaemolyticus, H. influenzae,* and *E. coli.* Costerton et al. (1999; supra); and Murphy et al., "Biofilm Formation By NonTypeable *Haemophilus influenzae*: Strain Variability, Outer Membrane Antigen Expression And Role Of Pili" *BMC Microbiol* 2:7-15 (2002).

Potentially, targeting bacterial adhesion to surfaces, microcolony formation, polysaccharide matrix development, or even disruption of mature biofilms could all be viable approaches to combat bacteria growing in biofilms.

The present invention contemplates that multicellular structures generated during bacterial colonization create microaerobic microenvironments (i.e., for example, low oxygen or reducing conditions) thereby inducing increased LOS-PC epitope display.

II. LOS-PC Epitope Biosynthesis

The present invention is related to the biosynthesis of the *H. influenzae* LOS-PC epitope. In one embodiment, at least one LOS-PC epitope biosynthetic gene is upregulated under a microaerobic redox growth condition (i.e., for example, increased mRNA transcript expression). In one embodiment, the biosynthetic gene is responsible for LOS and/or LPS modification or biosynthesis. In one embodiment, the LOS biosynthetic gene includes, but is not limited to, the licABCD gene complex (i.e., the lic1 operon). PC epitope display on a LOS molecule in *H. influenzae* includes, but is not limited to, four genes within the lic1 operon: i) licA (a choline kinase); ii) licB (a choline transporter); ii) licC (a pyrophosphorylase); and iv) licD (a choline transferase). Weiser et al. (1997). Although it is not necessary to understand the mechanism of an invention, it is believed that the lic1 operon is needed for synthesizing and attaching the PC epitope to LOS. The present invention contemplates a method to modulate LOS-PC epitope display comprising growing a bacterium under a redox growth condition under conditions such that LOS glucose incorporation and/or abundance in combination with the lic1 operon expression are modified.

The present invention presents representative microarray data indicating a global expression pattern consistent with increased carbohydrate breakdown and subsequent energy generation under aerobic redox growth conditions, a condition which concomitantly decreases LOS precursor abundance (i.e., for example, carbohydrates, sugars, glucose or UDP-glucose). (See FIG. 5). Although it is not necessary to understand the mechanism of an invention, it is believed that aerobically-induced precursor depletion (i.e., for example, UDP-glucose) may decrease LOS outer core modifications. In one embodiment, galU produces UDP-glucose whereby UDP-glucose comprises a precursor of a LOS outer core modification to which PC is added. In one embodiment, the LOS outer core modification comprises a LOS-PC epitope display.

Some embodiments of the present invention comprise genomics and microarray technology (i.e., for example, expression profiling) in methods to generate information regarding antimicrobial drug discovery. For example, it is known that many genes from sequenced organisms have no assigned function, meaning that many novel targets await identification. Microarray technology comprises an empirical process that identifies functions for unknown genes by: i) looking at their coexpression with other genes and, ii) by grouping gene expression profiles to identify potential regulators.

The application of microarray technology to human bacterial infections present an ideal opportunity to identify novel target compositions and methods of treatment. By isolating bacteria recovered from infected patients and analyzing their gene expression profiles, genetic pathways involved in pathogen-human interactions can be identified.

One embodiment of the present invention contemplates that lic1 operon regulation, alone, does not account for LOS-PC epitope modulation by redox growth conditions and considers the involvement of other mechanisms. Although it is not necessary to understand the mechanism of an invention, it is believed that building of the complete LOS structure requires numerous biosynthetic steps to produce the final configuration for PC epitope attachment wherein each biosynthetic step is potentially subject to regulation. In one embodiment, a method to enhance LOS-PC epitope display comprises growing a bacterium under a microaerobic growth condition, wherein said bacterium comprises at least one LOS biosynthesis gene under conditions such that said LOS gene is overexpressed. In one embodiment, a method to repress LOS-PC epitope display comprises growing a bacterium under an aerobic growth condition. In one embodiment, the LOS biosynthesis gene comprises a lic1 operon, wherein said operon comprises a licABCD gene complex.

One embodiment of the present invention contemplates that redox growth conditions influence lic1 mRNA transcript expression and LOS-PC epitope display by measuring *H. influenzae* LOS-PC monoclonal antibody (mAb) reactivity (i.e., for example, using TEPC-15). In one embodiment, a microaerobic redox growth condition increased lic1 mRNA transcript levels and increased LOS-PC epitope display. In another embodiment, an aerobic redox growth condition decreases lic1 mRNA transcript levels and decreases LOS-PC epitope display. Although it is not necessary to understand the mechanism of an invention, it is believed that lic1 mRNA phase variation does not modulate LOS-PC epitope display. It is further believed that lic1 mRNA overexpression does not increase LOS-PC epitope display under aerobic conditions. Although it is not necessary to understand the mechanism of an invention, it is believed that lic1 genes play a role in PC epitope addition to the LOS but may not directly influence on LOS-PC epitope display, lic1 mRNA regulation is likely to partially contribute to modulation of LOS-PC epitope display.

In one embodiment, the microaerobically-induced LOS biosynthetic gene comprises the licABCD gene complex (i.e., lic1 operon), wherein said genes provide LOS-PC display. (See FIG. 1C, FIG. 2A, 2B, and Table 2). In one embodiment, the LOS biosynthetic gene comprises a galU gene (i.e., for example, HI0812) wherein galU expression increased approximately 1.5-fold. Although it is not necessary to understand the mechanism of an invention, it is believed that galU encodes a UDP-glucose pyrophosphorylase catalyzing the interconversion of glucose-1-phosphate to uridine diphosphate glucose (UDP-glucose). Weissborn et al. (1994). It is further believed that UDP-glucose represents the activated form of a sugar used in the biosynthesis of various carbohydrates, including LOS and/or LPS. Sundararajan et al. (1962). Studies have shown that *E. coli* galU mutants produce a truncated LPS core that lacks glucose and galactose. Sundararajan et al. (1962). Similarly, galU mutants in *H. influenzae* (having 72% homology to *E. coli* galU mutants) also produce truncated LOS molecules. Hood et al. (1996a).

III. LOS-PC Epitope Modulation by Redox Growth Conditions

In some embodiments, the present invention contemplates that variations in the redox growth conditions (i.e., for example, aerobic, microaerobic, or unareated/anaerobic culture conditions) modulate LOS-PC epitope display. In one embodiment, a LOS-PC epitope display comprises an *H. influenzae* virulence determinant. In one embodiment, variations in redox growth conditions modulate *H. influenzae* global genetic expression profiles (i.e., for example, central carbohydrate metabolism biochemical pathways). Further, embodiments of the present invention contemplate an integrated metabolic model that provides regulatory biochemical control of LOS-PC epitope display. In one embodiment, LOS modification is under the genetic control of at least one glycolytic pathway.

A. Aerobically-Induced Central Carbohydrate Metabolism

Figure 5:
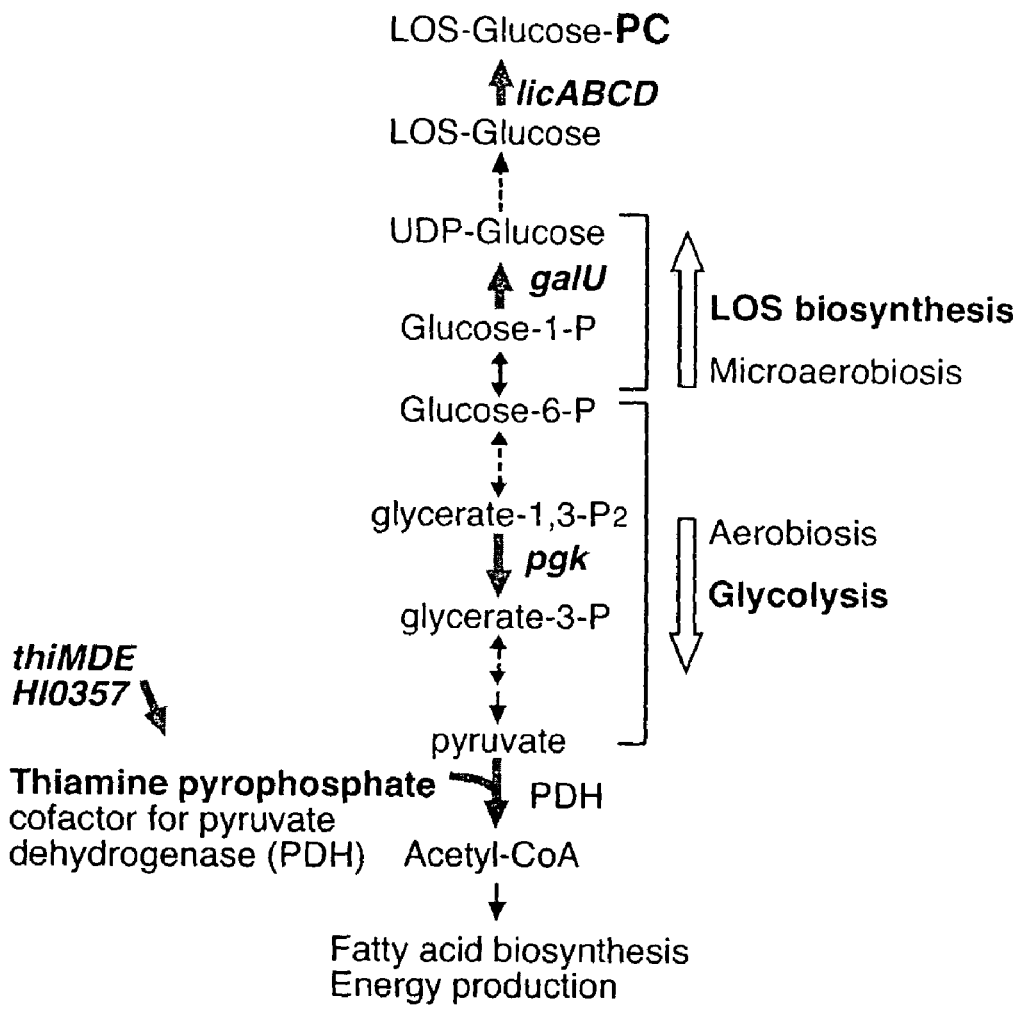
FIG. 5 presents one embodiment of a biochemical pathway integrating central carbohydrate metabolism and LOS precursor metabolism in $H.$ $influenzae$. Based on the data disclosed herein, the expression of phosphoglycerate kinase (pgk), thiMDE, and HI0357 genes are aerobically induced (open arrows), while expression of galU and licABCD are microaerobically induced (crosshatched arrows). Dashed arrows represent multiple intermediate enzymatic reactions.

Genomic expression profiling performed herein is consistent with embodiments comprising either: i) an aerobically-induced depletion of precursor sugars available for extension of the LOS outer core; and ii) a microaerobic induction of LOS and PC epitope biosynthesis (See Tables 1 and 2, and FIG. 5, respectively). In some embodiments, aerobic redox growth conditions increase thiamine biosynthesis (i.e., for example, by inducing thiamine pyrophosphate) and phosphoglycerate kinase gene expression. In other embodiments, thiamine-dependent enzymes utilize thiamine pyrophosphate as a cofactor (i.e., for example, pyruvate dehydrogenase. Although it is not necessary to understand the mechanism of an invention, it is believed that increased pyruvate dehydrogenase levels increases sugar utilization for energy generation, thereby reducing the levels of glucose precursor available for LOS modification and subsequent PC epitope attachment.

Conversely, other embodiments contemplated by the present invention comprise microaerobic redox growth conditions that induce expression of several genes involved in LOS biosynthesis or modification including, but not limited to, licABCD (i.e., lic1 operon) and galU. Although it is not necessary to understand the mechanism of an invention, it is believed that the expression profile disclosed herein suggests that LOS-PC epitope display modulation may be resultant from altered generation and utilization of LOS sugar precursor by central carbohydrate metabolic enzymes and pathways. It is further believed that a glycolysis versus carbohydrate synthesis ratio disruption should modulate LOS-PC epitope display.

Some embodiments of the present invention contemplate H. influenzae LOS-PC epitope modulators comprising redox growth condition sensitive central carbohydrate genes. In one embodiment, the proteins encoded by the central carbohydrate genes regulate central carbohydrate biochemical pathways. In one embodiment, the redox growth condition comprises an aerobic environment, wherein expression of the central carbohydrate gene is increased under conditions such that LOS biosynthesis is reduced. In another embodiment, the redox growth condition comprises a microaerobic environment, wherein expression of the central carbohydrate gene is decreased under conditions such that LOS biosynthesis is increased. Although it is not necessary to understand the mechanism of an invention, it is believed that FIG. 5 represents one possible model of interacting H. influenzae central carbohydrate metabolism pathways as it relates to LOS biosynthesis and the gene expression patterns consistent with the invention described herein.

The present invention contemplates a method to increase central carbohydrate gene expression comprising growing bacterium under an aerobic redox growth condition, wherein the genes convert at least one sugar molecule into energy. (See FIG. 5 and Table 1).

TABLE 1

Aerobically-Induced Rd Carbohydrate Genes (p values ≦0.01).

| Gene ID | Function | Fold induction | p value |
|---------|----------|----------------|---------|
| HI0367 | conserved hypothetical protein | 3.36 | 1.20E−04 |
| HI0507 | conserved hypothetical transmembrane protein | 4.11 | 1.67E−04 |
| HI1444 | 5,10 methylenetetrahydrofolate reductase (metF) | 3.24 | 3.01E−04 |
| HI0448 | PTS system, fructose-specific IIA/FPr component (fruB) | 2.84 | 7.32E−04 |
| HI1266 | hypothetical protein | 19.61 | 9.82E−04 |
| HI0542 | chaperonin (groES) | 2.54 | 9.91E−04 |
| HI0418 | transport protein, putative | 3.35 | 1.20E−03 |
| HI0358 | transcriptional activator, putative | 11.1 | 1.77E−03 |
| HI0406 | acetyl-CoA carboxylase, carboxyl transferase (accA) | 2.47 | 2.18E−03 |
| HI0337 | nitrogen regulatory protein P-II (glnB) | 2.86 | 2.92E−03 |
| HI0314 | crossover junction endodeoxy-ribonuclease (ruvC) | 2.28 | 3.64E−03 |
| HI1604 | phosphate permease, putative | 2.35 | 3.78E−03 |
| HI0355 | ABC transporter, permease protein | 7.05 | 4.36E−03 |
| HI0443 | recombination protein (recR) | 3.14 | 4.65E−03 |
| HI0146 | N-acetylneuraminate-binding protein, putative | 2.56 | 4.85E−03 |
| HI0357 | thiamine biosynthesis protein, putative | 4.45 | 5.25E−03 |
| HI1284 | translation initiation factor 2 (infB) | 32.2 | 5.77E−03 |
| HI0141 | glucosamine-6-phosphate isomerase (nagB) | 4.19 | 6.87E−03 |
| HI0478 | ATP synthase F1, subunit epsilon (atpC) | 2.36 | 7.18E−03 |
| HI0525 | phosphoglycerate kinase (pgk) | 2.01 | 7.94E−03 |
| HI0063 | poly(A) polymerase (pcnB) | 4.46 | 8.32E−03 |
| HI0264 | heme-hemopexin utilization protein A (hxuA) | 2.27 | 8.57E−03 |
| HI0417 | thiamin-phosphate pyrophosphorylase (thiE) | 2.65 | 8.65E−03 |
| HI0527 | ferredoxin (fdx-2) | 6.38 | 8.93E−03 |
| HI0949 | aminotransferase | 2.3 | 9.33E−03 |
| HI0447 | 1-phosphofructokinase (fruK) | 3.39 | 1.00E−02 |
| HI0415 | hydroxyethylthiazole kinase (thiM) | 5.6 | 1.01E−02 |
| HI0354 | ABC transporter, ATP-binding protein | 5.77 | 1.04E−02 |
| HI0453 | conserved hypothetical protein | 2.27 | 1.05E−02 |

In one embodiment, the central carbohydrate gene comprises a pgk gene (i.e., for example, HI0525) encoding the glycolytic enzyme, phosphoglycerate kinase. In one embodiment, the pgk gene is induced approximately two-fold. In one embodiment, the central carbohydrate gene comprises a thiamine pyrophosphate gene (TPP gene), encoding the biologically active form of thiamine. Although it is not necessary to understand the mechanism of an invention, it is believed that TPP is a metabolic enzyme cofactor for enzymes that convert carbohydrate to energy. It is further believed that TPP interacts with: i) pyruvate dehydrogenase for oxidative decarboxylation of pyruvate; ii) transketolase for metabolism of pentose sugars; and iii) a-ketoglutarate dehydrogenase for oxidation of a-ketoglutarate. Begley et al. (1999). Further, TPP genes may also encode putative homologues of E. coli enzymes known to generate the thiazole and pyrimidine moieties that form thiamine pyrophosphate. Vander Horn et al. (1993). In one embodiment, TPP gene expression is increased under aerobic redox growth conditions. In one embodiment, the TPP gene comprises thiM (i.e., for example, HI0415), wherein thiM expression is increased approximately 5.6-fold. In another embodiment, the TPP gene comprises thiE (i.e., for example, HI0417) wherein thiE expression is increased approximately 2.7-fold. In one embodiment, the TPP gene comprises thiD (i.e., for example, HI0416) wherein thiD expression is increased approximately 5.5-fold.

In one embodiment, the central carbohydrate gene comprises HI0357, wherein HI0357 expression is increased approximately 4.5-fold. Although it is not necessary to understand the mechanism of an invention, it is believed that HI0357 may be a putative thiamine biosynthesis gene. It is further believed that HI0357 may be co-located within the same operon as HI0354, HI0355, and HI0358I which are believed to have conserved domains having sequence similarity to proteins functioning as either thiamine transporters or result in thiamine biosynthesis. In one embodiment, the central carbohydrate gene is selected from the group consisting of HI0354, HI0355, and HI0358I wherein the expression is increased approximately 6 to 11-fold.

In one embodiment, the present invention contemplates an aerobic redox growth condition expression pattern comprising an increased pyruvate dehydrogenase cofactor production. In another embodiment, the present invention contemplates an elevated phosphoglucose kinase expression. Although it is not necessary to understand the mechanism of an invention, it is believed that post-transcriptional regulation likely contributes to central carbohydrate enzyme activity. It is further believed that since some central carbohydrate enzymes mediate entry of glycolytic products into the citric acid cycle for energy generation, an aerobic induction of, for example pyruvate dehydrogenase and/or phosphoglucose kinase, could deplete sugar precursors needed for LOS-PC synthesis. This mechanism represents one possibility consistent with reduced LOS-PC epitope when bacteria are grown under aerobic redox conditions.

B. Microaerobically-Induced LOS Biosyntheses Metabolism

The present invention contemplates a method to increase LOS biosynthetic gene expression comprising growing bacterium under a microaerobic redox growth condition, wherein the gene participates in at least one step in LOS synthesis that may or may not be related to PC epitope display. (See Table 2).

TABLE 2

Microaerobically-Induced Rd LOS Biosynthetic Genes (p values ≦0.01).

| Gene ID | Function | Fold induction | p value |
|---|---|---|---|
| HI1032 | transcriptional regulator, putative | 3.15 | 5.11E-06 |
| HI1722 | methionine aminopeptidase (map) | 3.88 | 5.54E-05 |
| HI1078 | amino acid ABC transporter, ATP-binding protein | 2.18 | 1.05E-04 |
| HI0600 | RecA protein (recA) | 2 | 2.08E-04 |
| HI1697 | lipopolysaccharide biosynthesis protein, putative | 2.68 | 2.90E-04 |
| HI1154 | proton glutamate symport protein, putative | 1.92 | 2.94E-04 |
| HI1150 | conserved hypothetical protein | 2.16 | 3.86E-04 |
| HI1229 | DNA polymerase III, subunits gamma and tau (dnaX) | 1.97 | 4.50E-04 |
| HI1538 | lic-1 operon protein (licB) | 2.5 | 6.46E-04 |
| HI1560 | hypothetical protein | 2.35 | 6.53E-04 |
| HI1338 | conserved hypothetical protein | 2.73 | 6.72E-04 |
| HI1463 | phosphoglucosamine mutase, putative (mrsA) | 4.04 | 7.08E-04 |
| HI1079 | ABC-type amino acid transport system, permease component | 2.03 | 8.64E-04 |
| HI0865 | glutamine synthetase (glnA) | 1.99 | 8.73E-04 |
| HI1632 | hypothetical protein | 2.76 | 9.79E-04 |
| HI0817 | conserved hypothetical protein | 1.79 | 1.00E-03 |
| HI0602 | HemY protein (hemY) | 1.87 | 1.18E-03 |
| HI0983 | hypothetical protein | 2.05 | 1.47E-03 |
| HI1005 | conserved hypothetical protein | 3.38 | 1.50E-03 |
| HI1033 | phosphoserine phosphatase (serB) | 2.19 | 1.79E-03 |
| HI1001 | inner membrane protein, 60 kDa (yidC) | 1.9 | 2.03E-03 |
| HI1000 | hemolysin, putative | 1.84 | 2.04E-03 |
| HI1663 | conserved hypothetical protein | 2.42 | 2.15E-03 |
| HI0813 | carbon storage regulator (csrA) | 1.66 | 2.74E-03 |

TABLE 2-continued

Microaerobically-Induced Rd LOS Biosynthetic Genes (p values ≦0.01).

| Gene ID | Function | Fold induction | p value |
|---|---|---|---|
| HI1699 | lipopolysaccharide biosynthesis protein, putative | 2.52 | 2.77E-03 |
| HI1066 | nitrite reductase, transmembrane protein (nrfD) | 3.95 | 2.86E-03 |
| HI1098 | hypothetical protein | 3.19 | 3.06E-03 |
| HI1706 | high-affinity choline transport protein (betT) | 2.38 | 3.06E-03 |
| HI1695 | lipopolysaccharide biosynthesis protein, putative | 2.23 | 3.16E-03 |
| HI1007 | penicillin tolerance protein (lytB) | 1.98 | 3.50E-03 |
| HI1682 | protease, putative (sohB) | 1.61 | 3.53E-03 |
| HI0976 | conserved hypothetical protein | 1.88 | 3.71E-03 |
| HI1547 | phospho-2-dehydro-3-deoxyheptonate aldolase (aroG) | 1.87 | 3.91E-03 |
| HI1578 | N-acetylgalactosaminyltransferase (lgtD) | 2.01 | 4.10E-03 |
| HI1714 | conserved hypothetical protein | 1.56 | 4.59E-03 |
| HI0081 | conserved hypothetical protein | 2.5 | 5.05E-03 |
| HI0999 | ribonuclease P (rnpA) | 1.82 | 5.18E-03 |
| HI1223 | conserved hypothetical protein | 1.76 | 5.33E-03 |
| HI1565 | Outer membrane receptor | 2.81 | 5.68E-03 |
| HI1365 | DNA topoisomerase I (topA) | 1.61 | 5.79E-03 |
| HI1272 | ABC transporter, ATP-binding protein | 2.66 | 6.23E-03 |
| HI1703 | conserved hypothetical protein | 2.1 | 6.50E-03 |
| HI1086 | conserved hypothetical protein | 1.79 | 6.60E-03 |
| HI1738 | conserved hypothetical protein | 1.53 | 6.90E-03 |
| HI1707 | sensor protein (ygiY) | 1.64 | 7.06E-03 |
| HI1698 | lipopolysaccharide biosynthesis protein, putative | 2.32 | 7.13E-03 |
| HI1041 | modification methylase | 1.58 | 7.54E-03 |
| HI1151 | conserved hypothetical protein | 2.04 | 8.08E-03 |
| HI1595 | DNA segregation ATPase | 2.24 | 8.73E-03 |
| HI1099 | hypothetical protein | 2.08 | 8.79E-03 |
| HI1094 | cytochrome C-type biogenesis protein (ccmF) | 2.98 | 8.88E-03 |
| HI1045 | anaerobic dimethyl sulfoxide reductase, chain C (dmsC) | 3.1 | 9.53E-03 |
| HI0957 | catabolite gene activator (crp) | 1.69 | 9.57E-03 |
| HI1518 | hypothetical protein | 3.09 | 9.85E-03 |

In one embodiment, the LOS biosynthetic gene comprises lgtD (i.e., for example, HI1578), wherein lgtD expression is increased approximately 2-fold. Although it is not necessary to understand the mechanism of an invention, it is believed that lgtD encodes a N-acetylgalactos-aminyltransferase that provides an N-acetylgalactosamine LOS extension in *H. influenzae*. Shao et al. (2002). It is further believed that the N-acetylgalatosamine is attached at heptose III of the LOS inner core unlike a PC epitope which is believed a substituted glucose residue linked to heptose I. Risberg et al. (1999). In one embodiment, the LOS biosynthetic gene comprises putative glycosyltransferase genes, wherein glycosyltransferase expression is increased approximately 2.5 fold. In one embodiment, the glycosyltransferase gene is selected from the group HI1695, HI1697, HI1698. In another embodiment, the glycosyltransferase gene comprises a sialyltransferase gene (i.e., for example, HI1699).

IV. Carbon Storage Regulator A (CsrA) Modulation of LOS-PC Epitope Display

The carbon storage regulation system was originally identified via a mutation which inactivates a small RNA binding protein, now known as CsrA. CsrA is a negative regulator of certain processes associated with the early stationary phase of growth, including glycogen synthesis and catabolism and gluconeogenesis. It is also known that a CsrA homologue mediates the expression of several extracellular virulence factors in the bacterium *Erwinia carotovora*. Chatterjee et al. *Appl. Environ. Microbiol.* 61:1959-1967 ((1995). CsrA is also known to modulate glycolytic pathways and affect cell surface properties. It is believed that CsrA is related to a diverse subset of RNA-binding proteins known as KH proteins and regulates glycogen biosynthesis pathway by binding to and facilitating decay of glgCAP protein.

Purified recombinant *E. coli* CsrA has been observed to bind to an approximate 350 nucleotide *E. coli* RNA as a large globular multisubunit complex. This RNA comprises a CsrA regulator designated CsrB. Romeo T., "Method Of Altering The Expression Of CSRB To Modify The Properties Of A Cell" U.S. Pat. No. 6,537,815 (herein incorporated by reference). In one embodiment of the present invention CsrB provides negative regulation on CsrA expression and therefore is believed to i) decrease central carbohydrate metabolism and ii) increase LOS-PC epitope display. Presently, it is unknown if CsrB is present in *H. influenzae*.

In one embodiment, the present invention contemplates a method to modulate LOS-PC epitope display comprising a post-transcriptional regulator protein. In one embodiment, the post-transcriptional regulator protein comprises a repressor protein. In one embodiment, the repressor protein is encoded by a CsrA gene. In one embodiment, the present invention contemplates a method to regulate LOS-PC epitope display comprising an *H. influenzae* CsrA protein homologue, wherein the homologue modulates central carbohydrate enzymes thereby affecting the cellular flux of sugar precursors needed for LOS modification. In one embodiment, the homologue is encoded by the HI0813 gene. In another embodiment, the homologue has a 67% amino acid identity to *E. coli* CsrA.

Although it is not necessary to understand the mechanism of an invention, it is believed that in *E. coli*, central carbohydrate metabolic pathways are regulated by a conserved, pleiotropic post-transcriptional regulator, CsrA. Romeo T. (1998). It is further believed that CsrA proteins regulate enzymes including, but not limited to: i) glycogen biosynthesis, Romeo et al. (1993; and Sabnis et al. (1995); ii) glycogen degradation, Yang et al. (1996); iii) gluconeogenesis, Sabnis et al. (1995); and iv) glycolysis, Sabnis et al. (1995).

In one embodiment, the present invention comprises a mutation in the CsrA gene within a bacterial genome that modulates *H. influenzae* LOS-PC epitope display. It is known that a mutagenized 10 kb segment of the *H. influenzae* Rd genome with a mariner derived minitransposon comprises a CsrA mutated gene. Akerley et al. (2002).

The present invention contemplates embodiments comprising a carbohydrate metabolic pathway regulator, wherein the regulator alters sugar precursor availability for LOS-PC epitope modification. In one embodiment, the regulator comprises a protein encoded by a CsrA gene. In one embodiment, the CsrA gene comprises a mutation. In one embodiment, the CsrA mutant gene comprises an insertion. In one embodiment, the CsrA insertion mutant comprises a kanamycin gene. In one embodiment, the CsrA gene mutation modulates LOS-PC epitope display. In one embodiment, the CsrA insertion mutant increases LOS-PC epitope display under aerobic redox growth conditions. In another embodiment, the CsrA insertion mutant increases LOS-PC epitope display under microaerobic growth conditions. Although it is not necessary to understand the mechanism of an invention, it is believed that any disruption in CsrA activity increases sugar precursors available for LOS modification, consequently increasing LOS-PC epitope display. Further, unlike the lic1 operon, CsrA activity increases LOS-PC epitope display under aerobic conditions.

In one embodiment, the CsrA mutant increases monocistronic galU mRNA transcript expression under redox growth conditions. In one embodiment, the redox growth condition is selected from the group consisting of aerobic, microaerobic, and unaerated (i.e., for example, anaerobic) culture conditions. Although it is not necessary to understand the mechanism of an invention, an increased monocistronic galU mRNA transcript expression leads to increased formation of UDP-glucose, a donor of glycosyl groups needed for LOS extension and substrate for PC epitope addition.

Although it is not necessary to understand the mechanism of an invention, it is believed that transcriptional polarity resulting from a downstream galU is not a factor. Data presented herein demonstrates that an in-frame CsrA deletion mutation (8Δkan) increases LOS-PC epitope display as compared to wild-type *H. influenza* Rd under aerobic, microaerobic and unaerated culture conditions. (See FIG. 6). In one embodiment, the present invention contemplates a method to induce LOS-PC epitope display under microaerobic redox growth conditions in *H. influenzae* comprising a CsrA deletion mutant further comprises additional regulatory pathways. Although it is not necessary to understand the mechanism of an invention, it is believed that the CsrA protein may negatively affect the level of the sugar precursors needed for LOS extension, similar to the repressive effects of CsrA protein on gluconeogenesis and glycogen biosynthesis in *E. coli*. Romeo T., (1998).

It is known that CsrA disruption in *E. coli* results in: i) increased gluconeogenesis by increasing expression of genes or enzymes of central carbohydrate metabolism including, but not limited to, phosphoenolpyruvate carboxykinase (pckA), fructose-1,6-bisphosphatase (Fbp), phosphoenolpyruvate synthase (Pps), and phosphoglucomutase (Pgm); and ii) decreases glycolysis by decreasing levels of glycolytic enzymes including, but not limited to, glucose-6-phosphate isomerase (Pgi), 6-phosphofructokinase (PfkA), triosephosphate isomerase (Tpi), and, enolase (Eno). Romeo, (1998). Further, CsrA homologues are widespread among plant and human pathogenic bacteria and act mainly as negative regulators of virulence properties, including, but not limited to, extracellular proteases, quorum sensing molecules, and secondary metabolites (i.e., for example, hydrogen cyanide or pyocyanin) and regulation of invasion genes. Chatterjee et al. (1995); Cui et al. (1995); Pessi et al. (2001), and Lawhon et al. (2003). Furthermore, in the phytopathogen, *Erwinia amylovora*, the CsrA homologue, rsmA represses the production of capsular exopolysaccharide, which is required for pathogenicity in this organism (Ma et al., 2001). At present, however, it is not believed that a CsrA homologue is present in humans.

The present invention contemplates that gal U mRNA expression may be regulated by redox conditions of growth and CsrA gene expression. In one embodiment, *H. influenzae* LOS-PC epitope display comprises a multifactorial mechanism involving at least two biochemical pathways. Although it is not necessary to understand the mechanism of an invention, it is believed that many genes contribute to LOS biosynthesis and are independently regulated by redox growth conditions. (See Table 2). It is further believed that a coordinated regulation of multiple genes mediate LOS-PC epitope display redox growth condition modulation (supra). For example, redox growth conditions regulate both the lic1 operon and galU mRNA transcript expression which interact to modulate, at least in part, LOS-PC epitope display.

In one embodiment, the present invention contemplates a protein encoded by a CsrA gene that regulates monocistronic and multicistronic galU mRNA transcript expression in bacteria. In one embodiment, at least one galU mRNA transcript modulates a bacterial virulence factor (i.e., for example, a LOS-PC epitope). Rioux et al. (1999); Marra et al. (2001); and Nesper et al. (2001). It is known that *H. influenzae* galU mutants have defective LOS and LPS structures and show attenuated colonization (i.e., reduced virulence) in animal models of *H. influenzae* infection. Hood et al. (1996a). These observations suggest that *H. influenzae* CsrA proteins may regulate additional virulence genes and may also control other gluconeogenic and glycolytic genes.

The present invention also contemplates that a disrupted CsrA protein expression increases galU expression thereby upregulating LOS-PC epitope display. In one embodiment, disrupted CsrA protein expression comprises administering CsrA antisense mRNA. Although it is not necessary to understand the mechanism of an invention, it is believed that, when considering CsrA activity in other organisms, an *H. influenzae* putative homologue is likely to coordinately regulate additional factors such as, but not limited to, central carbohydrate metabolism genes. Certain embodiments of the present invention also contemplate that besides CsrA expression and redox growth conditions additional virulence-associated LOS modifications are likely to influence LOS-PC epitope display modulation.

It is known that *H. influenzae* LOS outer core sugars (i.e., for example, glucose, galactose etc.) are the target substrates for PC epitope addition. Risberg et al. (1999); and Schweda et al. (2000). In one embodiment, the present invention contemplates a method to modulate PC epitope display comprising a galU regulator. In one embodiment, the galU regulator comprises a CsrA protein. Although it is not necessary to understand the mechanism of an invention it is believed that galU encodes a glucose pyrophosphorylase that controls glycosyl residue addition to the LOS outer core on which the PC epitope is displayed. In one embodiment, the CsrA protein negatively regulates galU mRNA transcript expression.

Figure 7:
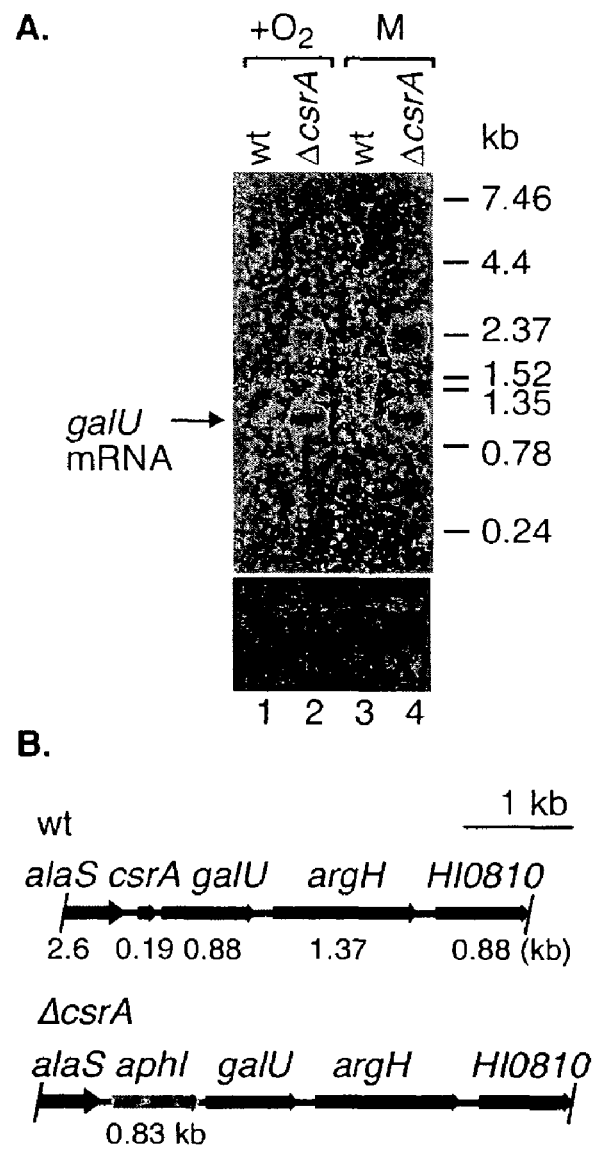
FIG. 7A presents exemplary data by Northern blot containing 15 mg of total RNA from aerobically (+O2) or microaerobically (M) grown wild-type $H.$ $influenzae$ Rd (wt: lanes 1 and 3) and a ΔCsrA mutant (Δ8kan: lanes 2 and 4) hybridized with a galU-specific probe. Arrow indicates ~0.88 kb galU mRNA. Ethidium bromide stained gel is shown directly below.
FIG. 7B presents one embodiment of a genomic organization of galU and flanking genes in wild-type and ΔCsrA mutant, Δ8kan in which the CsrA coding region was replaced with the KmR cassette, aphI. The molecular weight sizes (kb) below each locus are the estimated gene lengths annotated by TIGR.

In one embodiment, the present invention contemplates a method to regulate galU transcript expression through the interaction of redox growth conditions and/or a CsrA deletion mutant. In one embodiment, a ~0.9 kb galU mRNA monocistronic transcript (i.e., for example, 0.83 kb) was increased in the CsrA deletion mutant under both aerobic and microaerobic redox growth conditions as compared to the Rd wild-type. (See FIG. 7A, lanes 1-4). In another embodiment, a ~1.5 kb galU mRNA multicistronic transcript (i.e., for example, 1.52 kb) was increased in wild-type Rd under microaerobic redox growth conditions (See FIG. 7A, lanes 1 & 3). In another embodiment, a ~2.4 kb galU mRNA multicistronic transcript (i.e., for example, 2.37 kb) was increased in the CsrA deletion mutant under microaerobic redox growth conditions. (See FIG. 7A, lanes 2 & 4). In one embodiment, the present invention contemplates a CsrA deletion mutation comprising an in-frame replacement with the coding region of a kanamycin resistance gene (i.e., for example, aphI). (See FIG. 7B).

Figure 6:
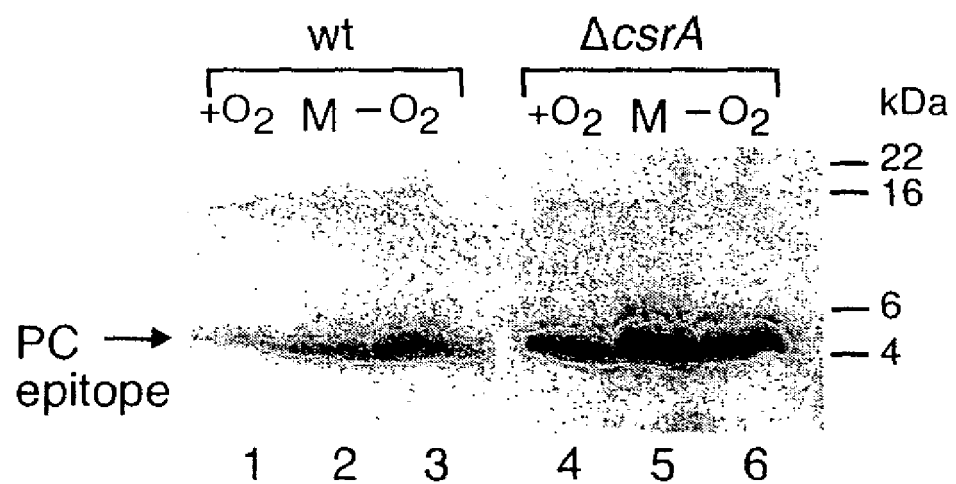
FIG. 6 presents exemplary data showing LOS-PC epitope display by Western blot of whole-cell lysates from wild-type $H.$ $influenzae$ Rd and the ΔCsrA non-polar deletion mutant (i.e., produced in strain Δ8kan) grown under three redox growth conditions: +O2: aerobic, M: microaerobic; and −O2: unareated.

In one embodiment, the present invention contemplates that LOS-PC epitope display and galU mRNA transcript expression both are modulated by CsrA gene activity (i.e., for example, via protein expression) and/or redox growth conditions. (See FIG. 6 and FIG. 7, respectively). Although it is not necessary to understand the mechanism of an invention, it is believed that CsrA proteins and redox growth conditions exert independent control mechanisms, wherein a CsrA repressor protein mediates a negative regulation on monocistronic galU mRNA transcript expression while redox growth conditions mediate either positive (i.e., for example, under a microaerobic condition) or negative (i.e., for example, under an aerobic condition) regulation on multicistronic galU mRNA transcript expression. It is further believed that increased galU expression of encoded UDP-glucose pyrophosphorylase increases the intracellular UDP-glucose level thereby increasing LOS glycosyl residue incorporation providing for increased LOS-PC epitope display. This mechanism is consistent with the observed increase in LOS-PC epitope display in both the wild-type *H. influenzae* Rd and CsrA mutant strain (8Δkan) when exposed to microaerobic conditions. (See FIG. 1B and FIG. 6). It is further believed that regulation of galU might contribute to the increased microaerobic LOS-PC epitope display observed in both wild-type and the CsrA mutant strains, though complete LOS-PC epitope display modulation likely involves the licABCD gene complex and other central carbohydrate metabolism genes. (See FIG. 1B and FIG. 6).

Other embodiments contemplated by the present invention comprise LOS-PC epitope display modulation comprising a CsrA gene encoding a regulatory mRNA transcript. In one embodiment, the regulatory mRNA transcript comprises a small untranslated regulatory RNA (sRNA). Although it is not necessary to understand the mechanism of an invention, it is believed that CsrA homologue activity in non-*H. influenzae* species (i.e., for example, *E. coli*) might be modulated by small untranslated regulatory RNAs (sRNAs). Romeo (1998). It is further believed that these sRNAs are in turn regulated in a complex manner involving transcriptional control by a two-component signal transduction system and quorum sensing. Heeb et al. (2002; Valverde et al. (2003); and Weilbacher et al. (2003).

V. Clinical Therapeutics

Many methods of administering therapeutic compounds are useful in the present invention. For instance, systemic delivery of targeted therapeutic compounds are contemplated. Targeted therapeutic compounds include, but are not limited to, bacteriophages or encapsulated carriers having binding partners for specific cell surface epitopes. Alternatively, therapeutic compounds may be administered in a free form including, but not limited to, uniform phosphorothiate oligonucleotides or locked oligonucleotides. Further, therapeutic compounds may be administered using polymeric carriers including, but not limited to, microcapsule-forming polymers, hydrogen bonding polymers, or collagen polymers.

A. Bacteriophage Therapy

The present invention contemplates a bacteriophage comprising a therapeutic compound capable being delivered to a patient under conditions such that the bacteriophage becomes incorporated into a bacterial cell. In one embodiment, the bacteriophage comprises a mu-like phage (i.e., for example, HP1, HP2, or S) and a plasmid. In one embodiment, the plasmid comprises a sense oligonucleotide encoding at least a portion of a CsrA protein. In another embodiment, the plasmid comprises an antisense oligonucleotide encoding at least a portion of a CsrA protein. In one embodiment, the bacteriophage becomes incorporated into an *H. influenzae* cell under conditions such that the *H. influenzae* cell is transformed (i.e., becomes lysogenic). Bacteriophage constructs comprising plasmids may be constructed by methods that are known in the art. Rancourt et al., "Bacteriophage Vectors Generated By Bacteriophage/Plasmid Recombination" U.S. Pat. No. 6,335,185. Filed: Feb. 2, 1999. Issued: Jan. 1, 2002 (herein incorporated by reference).

This invention utilizes the observation that bacteriophages may successfully become incorporated into, and transform, host bacteria by stable integration into bacterial DNA (i.e., thereby inducing a lysogenic state). Although it is not necessary to understand the mechanism of an invention, it is believed that bacterial molecular mechanisms exist to incorporate phages into host bacterial membranes and facilitate their subsequent integration within host bacterial DNA. Analogous approaches that induce the lytic state of a bacteriophage life cycle are known. Pelletier et al., "Development Of Novel Anti-Microbial Agents Based On Bacteriophage Genomics" U.S. Pat. No. 6,783,930. Filed: Dec. 2, 1999. Issued: Aug. 31, 2004 (herein incorporated by reference).

Six *H. influenzae* bacteriophages are believed known (i.e., for example, HP1, HP2, S2A, B, C, N3, and φflu). Bacteriophages HP1, HP2 and S2A are known to: i) become incorporated into *H. influenzae* strains; and ii) lack the necessary genes required for capsular synthesis (i.e., these bacteriophages are incapable of becoming induced into the lytic cycle). It is known that the HP1/S2 phage family exists as a prophage in the chromosome of strain R2866 (a nontypeable invasive *H. influenzae*). Nizet et al., "A Virulent Nonencapsulated *Haemophilus influenzae*." *J Infect Dis* 173:180-186 (1996) {Erratum, 178:296 1998}. In one embodiment, the present invention contemplates a bacteriophage comprising a first oligonucleotide sequence selected from the group consisting of HP1, HP2 and S2 (i.e., for example, S2A), and a plasmid comprising at least a portion of a second oligonucleotide sequence selected from the group consisting a sense CsrA oligonucleotide and an antisense CsrA oligonucleotide.

Bacteriophage HP1 comprises a 32-kb genome and is a temperate phage capable of either a lytic infection or lysogeny of the host. The promoters controlling the lysis-versus-lysogeny decision are located near the 5' end of the genome: one leftward and two rightward promoters transcribe cI and cox, which have genetic and functional homology to transcriptional regulators in lambda. Esposito et al., "The Complete Nucleotide Sequence Of Bacteriophage HP1 DNA" *Nucleic Acids Research* 24:2360-2368 (1996). The majority of HP1 genes located downstream from these regulators appear to encode proteins that are part of phage structure and assembly apparatus. S2 phages also appear capable of a temperate life cycle in *H. influenzae* hosts. The 5' 5.6 kb S2 region has major sequence differences relative to HP1 but do have interspersed regions of high homology. Skowronek et al., "Comparison of HP1c1 And S2 Phages Of *Haemophilus influenzae*" *Acta Microbiol. Pol.* 35:227-232 (1986).

An HP2 chromosome comprises 31,508 bp, similar to the size of S2 phage types A and B based on restriction mapping. The molar percentage of adenine and thymidine (A+T %) in the HP2 chromosome is 60.04%, a value similar to that in the Rd KW20 chromosome (61.86%). The organization of the HP2 genome comprises cohesive ends are similar to HP1. HP2 appears to contain five transcriptional units, with the control of each of these units directing or repressing bacteriophage replication. As in HP1, the pR1, pR2, and pL1 promoters of HP2 adjoin the early regulatory elements. Flanking these promoters are elements believed to control the lysis-versus-lysogeny decision. If the products of the pL1 promoter dominate, lysogeny is maintained, repressing all other bacteriophage gene expression. If the pR1 and pR2 promoters are activated, the lytic cycle will ensue. Products of the pR1- and pR2-activated transcript should control bacteriophage DNA replication and presumably activation of the downstream genes through hypothetical promoter elements between orf16 and orf17. Genes responsible for bacteriophage particle production and host lysis reside in these diverging transcripts, one of which contains orf15 and orf16, while the other contains orf17 through orf35. Many of the ORFs in the latter transcript show homology to structural proteins of P2 and other phages. As in HP1, orf14 appears to have its own promoter and terminator.

In one embodiment, the present invention contemplates plasmids comprising an HP2 host construct. (See Genbank Accession No. AY027935; FIG. 10A-H). Such HP2 construct plasmids may be constructed by using known methods in the art. For example, by using PCR primers 1 and 2 (See FIG. 11) a 1.7-kb fragment of HP2 DNA containing int and attP may be amplified and ligated to pTrcHisB restricted with BamHI and XhoI (pBJ102). PCR primers 3 and 4 (See FIG. 11) are then used to amplify a 2.0-kb downstream portion of the HP2 prophage that is subsequently ligated into pBJ102 digested with BglII and EcoRI (pBJ102.2). A BamHI-restricted TSTE cassette ligation into BglII-digested pBJ102.2 creates pBJ102.3. The TSTE cassette contains the aph(3')I gene flanked by *H. influenzae*-specific uptake (hUS) sequences. Sharetzsky et al., "A Novel Approach To Insertional Mutagenesis Of *Haemophilus influenzae*" *J Bacteriol* 173: 1561-1564 (1991). The TSTE cassette confers ribostamycin resistance to *H. influenzae* and kanamycin resistance to *E. coli*. Plasmid pBJ102.3 is then digested with BamHI and EcoRI and may transform competent *H. influenzae* strain R2866 selecting for ribostamycin resistance. Ribostamycin-resistant transformants, are then shown to be devoid of most of the prophage genome by Southern blotting and to lack phage production after mitomycin C treatment, as assessed by electron microscope observation and infection assays known to those of skill in the art.

hUS sequences comprise a 9-bp core sequence and may occur in a *H. influenzae* genome, on average, once every 1,249 bp. Smith et al., "Frequency And Distribution Of DNA Uptake Signal Sequences In The *Haemophilus influenzae* Rd Genome" *Science* 269:538-540 (1995). The ability of *H. influenzae* phage DNA to be introduced by transformation suggests that a phage genome would have many hUSs. As an alternative to transfection, transformation could serve as a means for phage DNA dissemination in *H. influenzae*, and transformation bypasses restriction-modification surveillance, unlike bacteriophage infection. Although it is not necessary to understand the mechanism of an invention, it is believed that both the HP1 and HP2 genome comprise at least 17 hUSs, although at different genomic locations.

The present invention contemplates hybrid lysogens comprising HP1 and HP2 wherein HP1 and HP2 each comprise a different therapeutic compound. In one embodiment, the hybrid lysogen was constructed by first cloning a 7.5-kb HindIII prophage fragment containing the HP2 immunity genes from strain R2866 into the HindIII site of pUC18. This plasmid, designated pBJ100.1, contains a portion of a threonine synthetase gene and a BamHI site in an intergenic region 5' to the prophage. After cloning TSTE into this BamHI site, the plasmid (pBJ100.2) may be linearized and transformed into competent R3152 selecting for ribostamycin resistance. One possible transformant has been designated HP1/HP2P (strain R3403) and acquired an HP2 immunity region as indicated by PCR. Williams et al. (supra). The chromosomal DNA of another transformant that retains HP1 immunity region can be digested and transformed into R2866. Another transformant acquiring an HP1 immunity region may be designated HP2/HP1P (strain R3404).

B. Oligonucleotides

The present invention contemplates an oligonucleotide capable of hybridizing to *H. influenzae* nucleic acid. In one embodiment, *H. influenzae* nucleic acid comprises CsrA-related nucleic acid and may include, but is not limited to, coding region DNA, promoter DNA, mRNA transcripts, or ribosomal nucleoprotein complexes. In one embodiment, the oligonucleotide comprises a uniform phosphorothiate. In another embodiment, the oligonucleotide comprises locked nucleic acids. In another embodiment, the oligonucleotide comprises a sense nucleotide base sequence. In another embodiment, the oligonucleotide comprises an antisense nucleotide base sequence.

H. influenzae can take up oligonucleotides from its environment by an active mechanism induced by nutrient starvation. In one embodiment, an oligonucleotide comprises a highly conserved 9-bp consensus sequence within an approximate 24 bp motif. In one embodiment, the 24 bp motif might be linked to a 5' end of a therapeutic oligonucleotide. For example, naturally transformable bacterium *Haemophilus influenzae* Rd contains 1471 copies of the DNA uptake signal sequence (USS) 5'-AAGTGCGGT (SEQ ID NO:12) in its genome. *Neisseria meningitidis* contains 1891 copies of the USS sequence 5'-GCCGTCTGAA (SEQ ID NO:13). The USSs are often found in the base paired stem of transcription terminators. Smith et al., "DNA Uptake Signal Sequences In Naturally Transformable Bacteria" *Res Microbiol* 150:603-616 (1999).

1. Uniform Phosphorothiates

The present invention contemplates systemic or localized naked nucleic acid administration. For example, naked antisense nucleic acid (i.e., for example, CsrA antisense) administration may be performed via intravenous administration as a uniform phosphorothiate. Nakamura et al., "Evidence of antisense tumor targeting in mice" *Bioconjug Chem.* 15:1475-80 (2004).

In one embodiment, the present invention contemplates oligonucleotides comprising uniform substitutions along the phosphodiester backbone. In one embodiment, an oligonucleotide comprises a phosphorothiate backbone uniformly methoxylated at the 2' position of a sugar moiety. In another embodiment, an oligonucleotide comprises a phosphodiester backbone uniformly propoxylated at the 2' position of the sugar moiety. In another embodiment, an oligonucleotide comprises a phosphorothioate backbone uniformly fluorinated at the 2' position of the sugar moiety.

In one embodiment, an oligonucleotide comprises a chimeric oligonucleotide comprising a uniform phosphorothiate backbone, substituted by a methoxy at the 2' position of the sugar moiety. In another embodiment, an oligonucleotide comprises a chimeric oligonucleotide comprising a uniform phosphorothioate backbones, substituted at the 2' position of the sugar moiety by either propoxy or fluorine. In another embodiment, an oligonucleotide comprises a phosphodiester backbone and 2'-methoxyethoxy substituents. Love, et al., "Liposomal Oligonucleotide Compositions" U.S. Pat. No. 6,096,720 (herein incorporated by reference).

Other uniform phosphothioate oligonucleotides include, but are not limited to, phosphorothioate phosphotriester, methyl phosphonate, short chain alkyl, cycloalkyl intersugar linkages, short chain heteroatomic, or heterocyclic intersugar ("backbone") linkages. In one embodiment, the phosphorothioate comprises CH2-NH—O—CH2, CH2-N(CH3)-O—CH2, CH2-O—N(CH3)-CH2, CH2-N(CH3)-N(CH3)-CH2 and O—N(CH3)-CH2-CH2 backbones (i.e., for example, where phosphodiester is O—P—O—CH2). In another embodiment, uniform phosphorothiate oligonucleotide comprise morpholino backbone structures. U.S. Pat. No. 5,034,506 (herein incorporated by reference). In other embodiments, a protein-nucleic acid or peptide-nucleic acid (PNA) backbone or a phosphodiester backbone of the oligonucleotide may be replaced with a polyamide backbone. In one embodiment, the bases may be bound directly or indirectly to the aza nitrogen atoms of the polyamide backbone. Nielsen et al., *Science* 254:1497 (1991). Other embodiments comprise oligonucleotides containing alkyl and halogen-substituted sugar moieties comprising one of the following at the 2' position including, but not limited to, OH, SH, SCH3, F, OCN, OCH2, OCH3, OCH2, CH2, OCH.3, OCH2, O(CH2)n, CH3, O(CH2)n, NH2 or O(CH2)n, CH3 where n is from 1 to about 10; C1 to C10 lower alkyl, substituted lower alkyl, alkaryl or aralkyl; Cl; Br; CN; CF3; OCF3; O—S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a cholesteryl group; a conjugate; a reporter group; an intercalator; a group for improving the pharmacokinetic properties of an oligonucleotide; or a group for improving the pharmacodynamic properties of an oligonucleotide and other substituents having similar properties. In one embodiment, an oligonucleotide comprises sugar mimetics such as, but not limited to, cyclobutyls in place of the pentofuranosyl group. Other embodiments may include at least one modified base form or "universal base" such as inosine.

In one embodiments of the invention, an oligonucleotide comprises 2'-deoxynucleotides and all backbone linkages are phosphorothioate linkages.

In one embodiment, an oligonucleotide comprises a chimeric oligonucleotide having one or more regions comprising 2'-deoxynucleotides and one or more regions comprising 2'-alkoxyalkoxynucleotides (i.e., for example, a 2'-methoxyethoxynucleotide); and the one or more, 2'-deoxynucleotide regions comprising a phosphorothioate backbone linkages and the one or more 2'-alkoxyalkoxynucleotide region comprising phosphodiester backbone linkages. In one embodiment, a chimeric oligonucleotide comprises a region of 2'-deoxynucleotides between two regions of 2'-alkoxyalkoxynucleotides.

The uniform phosphorothiate oligonucleotides contemplated by the invention may be conveniently and routinely made using well-known techniques such as solid phase synthesis. Equipment for such synthesis is available commercially from various sources (i.e., for example, Applied Biosystems). The use of such techniques to prepare oligonucleotides such as the phosphorothioates and alkylated derivatives are known. It is also known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

2. Locked Nucleic Acids

The present invention also contemplates locked nucleic acid (LNA) administration. LNAs comprise individual LNA monomers, and/or oligomers including LNA monomers, particularly such monomers and oligomers having unique nucleobase groups. Desirable nucleobase and nucleosidic base substitutions can mediate universal hybridization when incorporated into nucleic acid strands. LNA compounds may be used in a wide variety of applications, such as PCR primers, sequencing, synthesis of antisense oligonucleotides, diagnostics and the like. Wengel et al., "Novel LNA Compositions And Uses Thereof" U.S. Patent Application Publication No. 2003/0224377 A1. (herein incorporated by reference).

In one embodiment, the invention provides a method for contacting a target oligonucleotide molecule by administering an LNA under conditions that allow the nucleic acid to hybridize a target oligonucleotide. In some embodiments, the nucleic acid may bind to at least two different target molecules wherein the polynucleotide sequences of the target molecules differ by at least one nucleotide. In one embodiment, the nucleic acid comprises an antisense oligonucleotide having a modified base in the position corresponding to the nucleotide that differs between two or more target molecules. In one embodiment, the target molecule comprises a gene or portions thereof. In one embodiment, the target molecule comprises coding DNA or portions thereof. In one embodiment, the target molecule comprises a promoter region or portions thereof. In one embodiment, the target molecule comprises a regulatory region. In one embodiment, the target molecule comprises mRNA. In one embodiment, the target molecule comprises an ribosomal nucleoprotein.

In one embodiment, the invention contemplates using an nucleic acid in the manufacture of a pharmaceutical composition for treatment of a disease (i.e., for example, a CsrA antisense nucleic acid to treat H. influenzae infection).

In one embodiment, the administration of a nucleic acid provides a method for inhibiting the expression of a target nucleic acid in a cell. The method involves introducing into the cell a nucleic acid of the invention in an amount sufficient to specifically attenuate expression of the target nucleic acid (i.e., for example, CsrA mRNA). The introduced nucleic acid has a nucleotide sequence that is essentially complementary to a region of desirably at least 20 nucleotides of the target nucleic acid. In one embodiment, the cell is in a mammal cell.

In one embodiment, the invention provides a method for preventing, stabilizing, or treating a disease, disorder, or condition associated with a target nucleic acid in a mammal. This method involves introducing into the mammal a nucleic acid of the invention in an amount sufficient to specifically attenuate expression of the target nucleic acid, wherein the introduced nucleic acid has a nucleotide sequence that is essentially complementary to a region of desirably at least 20 nucleotides of the target nucleic acid.

In another embodiment, the invention provides a method for preventing, stabilizing, or treating a pathogenic infection (i.e., for example, a non-typeable H. influenzae infection) in a mammal by introducing into the mammal a nucleic acid of the invention in an amount sufficient to specifically attenuate expression of a target nucleic acid of a pathogen. The introduced nucleic acid has a nucleotide sequence that is essentially complementary to a region of desirably at least 20 nucleotides of the target nucleic acid.

In desirable embodiments of the therapeutic methods of the above aspects, the mammal is a human. In some embodiments, the introduced oligonucleotide is single stranded or double stranded.

In some embodiments, the oligonucleotide is less than 200, 150, 100, 75, 50, or 25 nucleotides in length. In other embodiments, the oligonucleotide is less than 50,000; 10,000; 5,000; or 2,000 nucleotides in length. In certain embodiments, the oligonucleotide is at least 200, 300, 500, 1000, or 5000 nucleotides in length. In some embodiments, the number of nucleotides in the oligonucleotide is contained in one of the following ranges: 5-15 nucleotides, 16-20 nucleotides, 21-25 nucleotides, 26-35 nucleotides, 36-45 nucleotides, 46-60 nucleotides, 61-80 nucleotides, 81-100 nucleotides, 101-150 nucleotides, or 151-200 nucleotides, inclusive. In addition, the oligonucleotide may contain a sequence that is less than a full-length sequence or may contain a full-length sequence.

Modified LNA nucleic acid monomers and oligomers of the invention contain at least one LNA unit and/or at least one modified nucleobase or nucleosidic base (often referred to herein as a universal or modified base). Modified nucleobases or nucleosidic bases contain non-natural base groups (i.e. for example, other than adenine, guanine, cytosine, uracil or thymine) but effectively hybridize to nucleic acid units that contain adenine, guanine, cytosine, uracil or thymine moieties. Exemplary oligomers contain 2 to 100, 5 to 100, 4 to 50, 5 to 50, 5 to 30, or 8 to 15 nucleic acid units. In some embodiments, one or more LNA units with natural nucleobases are incorporated into the oligonucleotide at a distance from the LNA unit having a modified base of 1 to 6 or 1 to 4 bases. In certain embodiments, at least two LNA units with natural nucleobases are flanking a LNA unit having a modified base on both sides thereof. Desirably, at least two LNA units independently are positioned at a distance from the LNA unit having the modified base of 1 to 6 or 1 to 4 bases.

Desirable modified nucleobases or nucleosidic bases for use in nucleic acid compositions of the invention include optionally substituted carbon alicyclic or carbocyclic aryl groups (i.e., for example, only carbon ring members), particularly multi-ring carbocyclic aryl groups such as groups having 2, 3, 4, 5, 6, 7, or 8 linked, particularly fused carbocyclic aryl moieties. Optionally substituted pyrene is also desirable. Such nucleobases or nucleosidic bases can provide significant performance results, as demonstrated for instance in the examples which follow. Heteroalicyclic and heteroaromatic nucleobases or nucleosidic bases also will be suitable as discussed below. In some embodiments, the carbocyclic moiety is linked to the 1'-position of the LNA unit through a linker (i.e., for example, a branched or straight alkylene or alkenylene).

LNA units contemplated herein comprise a nucleic acid unit that has a carbon or hetero alicyclic ring with four to six ring members (i.e., for example, a firanose ring, or other alicyclic ring structures such as a cyclopentyl, cycloheptyl, tetrahydropyranyl, oxepanyl, tetrahydrothiophenyl, pyrrolidinyl, thianyl, thiepanyl, piperidinyl, and the like). In one embodiment of the invention, at least one ring atom of the carbon or hetero alicyclic group is taken to form a further cyclic linkage to thereby provide a multi-cyclic group. The cyclic linkage may include, but is not limited to, one or more, typically two atoms, of the carbon or hetero alicyclic group. The cyclic linkage also may include, but is not limited to, one or more atoms that are substituents, but not ring members, of the carbon or hetero alicyclic group.

LNA units contemplated by the present invention further comprise a furanosyl-type ring and one or more of the following linkages: C-1', C-2'; C-2', C-3'; C-2', C-4'; or a C-2', C-5' linkage. In one embodiment, a C-2', C-4' is contemplated. In another embodiment of the invention, LNA units comprise compounds having a substituent on the 2'-position of the central sugar moiety (i.e., for example, ribose or xylose), or derivatives thereof, which favors a C3'-endo conformation. In another embodiment, LNA units comprise 2'-O-methyl, 2'-fluoro, 2'-allyl, and 2'-O-methoxyethoxy derivatives. Other LNA unit embodiments contemplated by the present invention are disclosed in International Patent Publication WO 99/14226, WO 00/56746, and WO 00/66604 (all herein incorporated by reference). Exemplary oligonucleotides contain one or more units selected from the group consisting of 2'-O,4'-C-methylene-.beta.-D-ribofuranosyls, 2'-deoxy-2'-fluoro ribonucleotides, 2'-O-methyl ribonucleotides, 2'-O-methoxyethyl ribonucleotides, peptide nucleic acids, 5-propynyl pyrimidine ribonucleotides, 7-deazapurine ribonucleotides, 2,6-diaminopurine ribonucleotides, or 2-thio-pyrimidine ribonucleotides.

Other LNA oligonucleotide embodiments comprise at least one LNA unit with a modified base. Suitable LNA oligonucleotides also may contain natural DNA or RNA units (i.e. for example, nucleotides) with natural bases, as well as LNA units that contain natural bases. Furthermore, the oligonucleotides of the invention also may contain modified DNA or RNA, such as 2'-O-methyl RNA, with natural bases. Desirable oligonucleotides contain at least one of and desirably both of: 1) one or more DNA or RNA units (i.e., for example, nucleotides) with natural bases; and 2) one or more LNA units with natural bases, in addition to LNA units with a modified base.

LNA oligonucleotides embodiments contemplated herein comprising natural bases obey Watson-Crick base-pairing rules and form duplexes that are significantly more stable than similar duplexes formed by DNA oligonucleotides. In addition, LNA oligonucleotides are capable of hybridizing with double-stranded DNA target molecules as well as RNA secondary structures by strand invasion as well as of specifically blocking a wide selection of enzymatic reactions such as, digestion of double-stranded DNA by restriction endonucleases; and digestion of DNA and RNA with deoxyribonucleases and ribonucleases, respectively.

The LNA oligonucleotides disclosed herein can provide significant nucleic acid probes for universal hybridization. In particular, universal hybridization can be accomplished with a conformationally restricted monomer, including a desirable pyrene LNA monomer. Universal hybridization behavior also can be accomplished in an RNA context. Additionally, the binding affinity of probes for universal hybridization can be increased by the introduction of high affinity monomers without compromising the base-pairing selectivity of bases neighboring the universal base.

Incorporation of one or more modified nucleobases or nucleosidic bases into an oligonucleotide can provide significant advantages. Among other things, LNA oligonucleotides can often self-hybridize, rather than hybridize to another oligonucleotide. Use of one or more modified bases with the LNA units can modulate affinity levels of the oligo, thereby inhibiting undesired self-hybridization.

Modified oligonucleotide compounds of the invention that contain base substitution (often referred to hereinafter as universal bases) can mediate universal hybridization when incorporated into e.g. a DNA strand, RNA strand and/or chimeric molecules such as a 2'-OMe-RNA/LNA chimeric strand. Desirable examples of novel LNA nucleotides with substitutions include pyrene-LNA or pyrenyl-LNA nucleotides. With respect to a 2'-OMe-RNA/LNA chimeric strand, the compounds of the invention have a high affinity hybridization without compromising the base-pairing selectivity of bases neighboring the universal base monomers.

3. Oligonucleotide Carriers

The present invention contemplates oligonucleotide administration under conditions such that degradation is reduced. One way to reduce degradation is to provide a composition wherein the oligonucleotide contacts a carrier under conditions such that the nucleic acid is protected from degradation.

a. Encapsulating Carriers

The present invention contemplates a method comprising administering an oligonucleotide by a carrier, wherein the carrier encapsulates the oligonucleotide. Various oligonucleotides are contemplated for encapsulation including, but not limited to, coding region DNA, promoter DNA, mRNA transcripts, or ribosomal nucleoproteins. In one embodiment, the oligonucleotide comprises a sense strand. In one embodiment, the oligonucleotide comprises an antisense strand. In one embodiment, the carrier is administered through transdermal routes utilizing jet injectors, microneedles, electroporation, sonoporation, microencapsulation, polymers or liposomes, transmucosal routes and intranasal routes using nebulizers, aerosols and nasal sprays.

Microencapsulation for transdermal or transmucosal administration may be created using natural or synthetic polymers including, but not limited to, starch, alginate and chitosan, D-poly L-lactate (PLA), D-poly DL-lactic-coglycolic microspheres, polycaprolactones, polyorthoesters, polyanhydrides and polyphosphazanes. Polymeric complexes comprising synthetic poly-ornithate, poly-lysine and poly-arginine or amiphipathic peptides are also useful for transdermal delivery systems. Bakaletz et al., "Nontypeable *haemophilus influenzae* virulence factors" United States Patent Application No. 2004/0219585 (herein incorporated by reference).

Amphipathic liposomes are also contemplated for transdermal, transmucosal and intranasal oligonucleotide delivery systems. Common lipids used for oligonucleotide delivery include, but are not limited to, N-(1)2,3-dioleyl-dihydroxypropyl)-N,N,N,-trimethylammonium-methyl sulfate (DOTAP), dioleyloxy-propyl-trimethylammonium chloride (DOTMA), dimystyloxypropyl-3-dimethyl-hydroxyethyl ammonium (DMRIE), dimethyldioctadecyl ammonium bromide (DDAB) and 9N(N',N-dimethylaminoethane)carbamoyl)cholesterol (DC-Chol). Liposomes encapsulating oligonucleotides further comprise helper lipids and liposomes that may enhance dermal absorption. These helper lipids include, but are not limited to, dioeolphosphatidylethanolamine (DOPE), dilauroylphosphatidylethanolamine (DLPE), dimystristoylphosphatidylethanolamine (DMPE), dipalmitoyl phosphatidylethanolamine (DPPE). In addition, triterpenoid glycosides or saponins derived from the Chilean soap tree bark (*Quillaja saponaria*) and chitosan (deacetylated chitan) are contemplated as useful adjuvants for intranasal and transmucosal oligonucleotide delivery.

In one embodiment, the present invention contemplates administering a liposome under conditions that the liposome is targeted to a particular tissue. In one embodiment, the targeting comprises coupling the liposome to a specific ligand such as a monoclonal antibody, sugar, glycolipid, or protein. Ligands which may be useful for targeting a liposome to a specific type of cell include, but are not limited to, intact or fragments of molecules which interact with the cell type's cell-specific receptors and molecules, such as antibodies, which interact with the cell surface markers of cells. Such ligands may easily be identified by binding assays well known to those of skill in the art. Additionally, a vector may be coupled to a nuclear targeting peptide, which will direct the vector to the nucleus of the host cell. Shapiro et al., "Methods and compositions for preventing and treating microbial infections" United States Patent Application No. 2003/0235577 (herein incorporated by reference).

Lipid formulations that enhance cell entry are commercially available from QIAGEN, for example, as Effectene™. (a non-liposomal lipid with a special DNA condensing enhancer) and Superfect™ (a novel acting dendrimeric technology). Liposomes are commercially available from Gibco BRL, for example, as Lipofectin™ and Liporectace™, which are formed of cationic lipids such as N-[1-(2,3 dioleyloxy)- propyl]-N,N,N-trimethylammonium chloride (DOTMA) and dimethyl dioctadecylammonium bromide (DDAB). Methods for making liposomes are well known in the art and have been described in many publications. Gregoriadis G., *Trends in Biotechnology* 3:235-241 (1985).

In one embodiment, a carrier comprises a biocompatible microparticle or implant that is suitable for implantation or administration to a mammalian host. Exemplary bioerodible implants that are useful in accordance with this method are described in PCT International Application No. WO95/24929, entitled "Polymeric Gene Delivery System". This reference describes a biocompatible, preferably biodegradable polymeric matrix for containing an exogenous gene under the control of an appropriate promoter. The polymeric matrix can be used to achieve sustained release of the exogenous gene in the patient.

In one embodiment, a polymeric matrix comprises a microparticle such as a microsphere (wherein the nucleic acid is dispersed throughout a solid polymeric matrix) or a microcapsule (wherein the nucleic acid is stored in the core of a polymeric shell). Other forms of the polymeric matrix for containing the nucleic acid include, but are not limited to, films, coatings, gels, implants, and stents. The size and composition of the polymeric matrix device is selected to result in favorable release kinetics in the tissue into which the matrix is introduced. The size of the polymeric matrix further is selected according to the method of delivery that is to be used, typically injection into a tissue or administration of a suspension by aerosol into the nasal and/or pulmonary areas. Preferably when an aerosol route is used the polymeric matrix and the nucleic acid and/or polypeptide is encompassed in a surfactant vehicle. The polymeric matrix composition can be selected to have both favorable degradation rates and also to be formed of a material which is bioadhesive, to further increase the effectiveness of transfer when the matrix is administered to a nasal and/or pulmonary surface that has sustained an injury. The matrix composition also can be selected not to degrade, but rather, to release by diffusion over an extended period of time.

b. Hydrogen Bonding Carriers

One embodiment of the present invention contemplates that a hydrogen-bonding polymer may be useful in carrying of genes, the isolation of oligonucleotides (i.e., for example, antisense nucleic acids) for the regulation of the transcription and/or the translation through an interaction with a nucleic acids such as DNA and RNA. In one embodiment, an oligonucleotide-polymer complex forms wherein the polymer is comprised of a polymer chain provided with hydrogen-bonding sites and having a conformation similar to the conformation of the oligonucleotide. Various oligonucleotides are contemplated for hydrogen-bonding polymers including, but not limited to, coding region DNA, promoter DNA, mRNA transcripts, or ribosomal nucleoproteins. In one embodiment, the oligonucleotide comprises a sense strand. In one embodiment, the oligonucleotide comprises an antisense strand.

In one embodiment, an oligonucleotide-polymer complex comprises a helical nucleic acid wherein said complex comprises a hydrogen-bonding polymer wherein the polymer chain has hydrogen-bonding sites thereby forming helix parameters similar to the helix parameters of the oligonucleotide. As an example, the polymer chain having helix parameters similar to the helix parameters of the oligonucleotide for use in the present invention may comprise a polysaccharide. As another example, such polymer chain is composed of a polypeptide or a synthetic polymer.

In one embodiment, a hydrogen-bonding polymer comprises a weight-average molecular weight of 1,000-10,000 daltons, preferably 3,000-8,000 daltons, and more preferably 5,000-7,000 daltons. In another embodiment, the number of the hydrogen-bonding sites formed on the polymer chain is five or more.

In another embodiment, a oligonucleotide-polymer complex comprises a nucleic acid and a hydrogen-bonding polymer, the polymer having a polymer chain with hydrogen-bonding sites formed on the polymer chain, said polymer chain having helix parameters similar to the helix parameters of the nucleic acid wherein the nucleic acid is bonded to the hydrogen-bonding polymer through the hydrogen-bonding sites.

In one embodiment, a hydrogen-bonding polymer comprises a β-1,3-glucan and/or a β-1,3-xylan, and more preferably a β-1,3-glucan including, but not limited to, schizophyllan, curdlan, lentinan, pachyman, griffollan, or sucleroglucan. In another embodiment, a hydrogen-bonding polymer comprises a monosaccharide or an oligosaccharide or is selected from guanine, cytosine, adenine, thymine, uracil or a derivative thereof. Sakurai et al., "Gene Carrier" United States Patent Application Publication No. 2003/0216346 A1 (herein incorporated by reference).

Schizophyllan is a beta-(1→3)-D-glucan and can form a novel complex with some single-chains of DNAs. Although it is not necessary to understand the mechanism of an invention, a polynucleotide bound in the complex is more stable to nuclease-mediated hydrolysis than the polynucleotide itself (i.e., for example, naked oligonucleotides). In one embodiment, the present invention contemplates schizophyllan complexed to an oligonucleotide (i.e., for example, a CsrA antisense oligonucleotide). The oligonucleotide complex may be produced using an in vitro (cell-free) transcription/translation assay. In this assay, a plasmid DNA coding a green fluorescence protein (GFP) and an oligonucleotide complex are designed to hybridize the ribosome-binding site in a GFP-coded mRNA. When an oligonucleotide complex is administered, a lower GFP expression efficiency (or higher antisense effect) is observed over naked DNA. This is because the oligonucleotide in the complex is protected from the attack of deoxyribonuclease. When exonuclease I, which specifically hydrolyzes single DNA chains, is present in the GEP assay system, the oligonucleotide effect was not changed for the complex while being weakened in the naked oligonucleotide system. Although it is not necessary to understand the mechanism of an invention, it is believed that exonuclease I cannot hydrolyze the oligonucleotide in the complex, while it can hydrolyze naked DNA to reduce its effect. Mizu et al., "Antisense oligonucleotides bound in the polysaccharide complex and the enhanced antisense effect due to the low hydrolysis" *Biomaterials* 25:3117-3123 (2004).

c. Collagen Carriers

The present invention contemplates a method comprising administering oligonucleotide using collagen carriers. Various oligonucleotides are contemplated for collagen carriers including, but not limited to, coding DNA, promoter DNA, mRNA transcripts, or ribosomal nucleoproteins. In one embodiment, the oligonucleotide comprises a sense strand. In one embodiment, the oligonucleotide comprises an antisense strand.

In one embodiment, the present invention contemplates oligonucleotide therapy for treating a bacterial infection (i.e., for example, a non-typeable *H. influenzae* infection), which comprises administering a preparation for facilitating the transfer of an oligonucleotide into a host cell (i.e., for example, an antisense CsrA oligonucleotide). In one embodiment, the oligonucleotide therapy comprises administering the preparation comprising a desired oligonucleotide and a collagen to a living body via transdermal, subcutaneous, intradermic, intramuscular, intraperitoneal, intracerebral, interstitial, intravascular, oral, rectal, or gastrointestinal route, whereby transferring efficiently said oligonucleotide into the cell.

In one embodiment, a preparation for facilitating the transfer of an oligonucleotide into a target cell comprises a complex wherein particles of the complex comprises a desired nucleic acid and a collagen and/or a collagen derivative, wherein the major axis of the particle is preferably 300 nm to 300 μm, more preferably 100 nm to 100 μm, even more preferably 50 nm to 50 μm, still more preferably 30 nm to 30 μm. In one embodiment, the collagen comprises atelocollagen. In one embodiment, the collagen derivative comprises a gelatin or a gelatin-crosslinking complex.

In one embodiment, a preparation for facilitating the transfer of an oligonucleotide according to the present invention may be in a form of solid or solution. In one embodiment, the preparation comprises a solid. In another embodiment, the preparation comprises a solution including, but not limited to, purified water, a physiological solution, a buffer isotonic with living bodies, or the like.

In one embodiment, a method for making a preparation (i.e., for example, a solution or suspension) for transferring an oligonucleotide comprises mixing an oligonucleotide solution with a collagen solution and at least one pharmaceutically acceptable additive. In one embodiment, the preparation can be formed into a film, a sponge, a powder, a Minipellet or the like, depending on the particular object. In one embodiment, after administration to the host cell the preparation will remain at the site where administered. In one embodiment, the preparation protects oligonucleotide from being degraded by a nuclease. In another embodiment, the preparation gradually releases the oligonucleotide under conditions such that the release rate of the oligonucleotide may be controlled by the preparation. In one embodiment, the concentration of the oligonucleotide around a host cell can be maintained at a high level under conditions such that the oligonucleotide efficiently inhibits the expression of the target mRNA in vivo without inducing any side-effect and retains the inhibition for a long period of time.

Moreover, the present invention relates to a method for treatment and prevention of infectious diseases comprising using the preparation as described above; or a method for treatment and prevention of various diseases induced by over-expression of the certain gene information; and particularly to a method for treatment and prevention of a bacterial infection.

One embodiment of the present invention contemplates a soluble collagen including, but not limited to, those that are soluble in an acidic or neutral water or a water containing a salt. A solubilized collagen includes, but is not limited to, an enzymatically solubilized collagen which may be solubilized with an enzyme, an alkali-solubilized collagen which may be solubilized with an alkali, and the like.

In one embodiment, a representative collagen can penetrate through a membrane filter having a pore size of 1 micrometer. In one embodiment, collagen solubility varies depending on the crosslinking degree of the collagen. For example, as the crosslinking degree increases, collagen solubility decreases. In one embodiment, a crosslinking degree of a collagen used in the present invention is between 0-5 crosslinks, preferably between 1-4 crosslinks, and more preferably between 2-3 crosslinks. In one embodiment, a molecular weight of the collagen comprises from about 300,000 to 900,000 daltons and more preferably from about 300,000 to about 600,000 daltons.

Collagens as used herein include those extracted from any animal species and genetic recombinants thereof. Preferable collagen is extracted from vertebrates or genetic recombinants thereof, more preferably collagens extracted from a mammal, a bird, a fish or genetic recombinant thereof, and more preferable collagen is extracted from a mammal or a bird having a high denaturation temperature, or genetic recombinants thereof. Any type of collagen may be used, and, because of the type existing in animal bodies, type I-V collagens or genetic recombinants thereof are preferable.

For example, such collagens include a type 1 collagen obtained by acid extraction from a mammal dermis or a genetic recombinant thereof. More preferably, they include, for example, a type 1 collagen obtained by acid extraction from calf dermis, a type 1 collagen produced by genetic engineering, and the like. As a type 1 collagen produced by genetic engineering, those derived from calf dermis or from human dermis are preferably. Collagens derived from tendon, which are also type 1 collagens, are not suitable herein, because they have a high degree of crosslinking and are insoluble.

In one embodiment, an atelocollagen may be obtained by removing enzymatically a telopeptide having high antigenicity. In another embodiment, an atelocollagen may be produced by genetic engineering using techniques known in the art. In one embodiment, an atelocollagen comprising three or less tyrosine residues per molecule. Alternatively, atelocollagen is commercially available (Koken Co., Ltd, Italy). Terada et al., "Method Of Promoting Nucleic Acid Transfer" United States Patent Application Publication No. 2004/0266004 A1; and Kubota et al. "Preparations For Oligonucleotide Transfer" United States Patent Application Publication No. 2004/0052840 (both herein incorporated by reference).

VI. Prevention And Treatment of *H. influenzae* Infections

The present invention is related to the prevention and treatment of bacterial infections. In one embodiment, the present invention contemplates the prevention and treatment of *H. influenzae* infection (i.e, for example, a non-typeable *H. influenzae* infection). In one embodiment, an *H. influenzae* infection may be prevented by administering an oligonucleotide to a host at risk for infection. In one embodiment, the oligonucleotide is conjugated to a bacteriophage. In another embodiment, an *H. influenzae* infection may be treated by administering an oligonucleotide to a host exhibiting at least one symptom of the infection. In one embodiment, the oligonucleotide in incorporated within a targeted encapsulated carrier. In one embodiment, the therapeutic compound includes, but is not limited to, a drug, a nucleic acid or a protein.

*H. influenzae* cells are spread from person to person by airborne respiratory droplets or direct contact with secretions. To colonize and infect a host (i.e., for example, pathogenesis), *H. influenzae* must contend with ciliary clearance mechanisms of the nasopharyngeal mucosal surface and the mucous barrier. Once past the mucous barrier and the ciliary escalator, *H. influenzae* attaches to mucosal epithelial cells. Invasion of mucosal surfaces appears to be an important characteristic of pathogenic bacteria. Stephens et al., "Pathogenic Events During Infection of the Human Nasopharynx with Neisseria meningitis and *Haemophilus influenzae*", *Rev Infect Dis*, 13:22-23 (1991).

It has further been reported that *H. influenzae* harbored in the nasopharynx is involved in the development of middle ear infections (otitis media), and that non-typeable *H. influenzae* adheres to nasopharyngeal and nasal mucosal cells. Harada et al., "Adherence of *Haemophilus influenzae* to nasal, nasopharyngeal and buccal epithelial cells from patients with otitis media" *Eur Arch Oto-Rhino-Laryng,* 247:122-124 (1990); and Stenfors et al., "Abundant Attachment of Bacteria to Nasopharyngeal Epithelium in Otitis-Prone Children", *J Infect Dis* 165:1148-1150 (1992). In accordance with the present invention, a CsrA sense mRNA or protein or a recombinant form thereof, decreases *H. influenzae* LOS-PC epitope display and reduces colonization and infectivity. Also in accordance with the present invention, a CsrA antisense mRNA or a recombinant form thereof, increases *H. influenzae* LOS-PC epitope display and consequently improves host immuno-recognition capability or increases *H. influenzae* susceptibility to passive immunization with an LOS-PC monoclonal antibody conjugate comprising a therapeutic compound.

*Haemophilus influenzae* meningitis is an infection of the membranes covering the brain and spinal cord (meninges) caused by *H. influenzae* bacteria *Haemophilus influenzae* type B (Hib) is a type of bacteria, not to be confused with the disease influenza, a lung infection caused by a virus. Prior to the availability of the Hib immunization, *H. influenzae* was the leading cause of bacterial meningitis in children under 5 years of age. It occurs most frequently in children from 1 month up to 4 years with a peak at 6 to 9 months.

In the United States, routine Hib immunization has made *H. influenzae* meningitis much less common. *H. influenzae* meningitis may follow an upper respiratory infection and may develop slowly or rapidly. The infection usually spreads from the respiratory tract to the bloodstream and then to the meninges. At the meninges, the bacteria produce infection and inflammation, causing serious illness and sometimes death. Consequently, *H. influenzae* now occurs in less than 2 in 100,000 American children.

Risk factors include a recent history of otitis media (ear infection), sinusitis (infection of sinuses), pharyngitis (sore throat), or other upper respiratory infection or a history of a family members with an *H. influenzae* infection. Another significant risk factor includes race—Native Americans have a rate of more than 3 times that of the general population. Placement in day care also increases risk.

Symptoms of *H. influenzae* meningitis include, but are not limited to, irritability, poor feeding in infants, fever (in young infants the temperature may actually be below normal), severe headache (older children), nausea and vomiting, stiff neck or pain in neck when flexed, pain in back when neck is flexed forward and chin brought toward chest (older children), unusual body posturing, and sensitivity to light.

*H. influenza* meningitis may be diagnosed by observing signs and performing tests including, but not limited to, bulging of the fontanelles (the soft spots on an infant's head), opisthotonos (lying with the back arched, head, back, and chin up), seizures, poor circulation, mental status changes (irritability, stupor, coma), elevated white blood cell count in blood, spinal fluid showing increased number of white blood cells, spinal fluid culture showing bacteria, serology (antibodies in blood) showing recent exposure to *H. influenzae,* and blood culture growing *H. influenzae*

Roughly 20% of patients may experience some hearing loss. Some patients will have brain damage that may lead to seizures, mental retardation, hydrocephalus (water on the brain), learning disorders, abnormalities in speech and language development, and behavioral problems.

VI. Sense and Antisense Nucleic Acid Therapy

Antisense nucleic acid technology may have an ability to examine the importance of a particular gene product during a bacterial infection. This ability may comprise a downregulation of gene expression to different degrees at different times during a bacterial infection. This mechanism relies on the fact that a nucleic acid fragment antisense to a gene of interest can reduce expression of that gene. It is known that specific antisense fragments to the a-hemolysin gene of *S. aureus* reduces toxin expression and attenuates virulence in a murine model. Kernodle et al., "Expression Of Antisense hla fragment in *Staphylococcus aureus* reduces Alpha-Toxin Production in vitro And Attenuates Lethal Activity In A Murine Model" *Infect Immun* 65:179-184 (1997). It is also known that the hlyA antisense fragment attenuates *S. aureus* virulence when placed under the control of an inducible promoter by regulating hylA gene expression in vivo. Ji et al., "Regulated Antisense RNA Eliminates Alpha-Toxin Virulence In *Staphylococcus aureus* infection" *J Bacteriol* 18(21):6585-6590 (1999).

Antisense technology can be more broadly applied by in vitro screening techniques. A subset of the genes identified were subjected to antisense inhibition in a murine kidney infection model. Virulence attenuation was found to be dependent on the level of inducer given to the mice. Ji et al., "Identification Of Critical *Staphylococcal* Genes Using Conditional Phenotypes Generated By Antisense RNA" *Science* 293:2266-2269 (2001). Such a system raises the possibility of turning off expression of a particular gene during infection in order to ascertain its importance at different times during the process.

Certain embodiments of the present invention contemplate the use of nucleic acids (i.e., for example, sense and/or antisense mRNA) to target components of LOS-PC epitope display biosynthesis pathways. In one embodiment, an antisense mRNA directed to a CsrA gene results in an upregulation of the LOS-PC epitope display. In another embodiment, a sense mRNA is directed to a CsrA gene results in a downregulation of the LOS-PC epitope display. In one embodiment, the sense and/or antisense mRNA contacts an oligonucleotide. In another embodiment, the sense and/or antisense mRNA contacts a protein or peptide.

Antisense nucleic acids are characterized as synthetic probes designed to hybridize with open reading frames of functional genes (i.e., DNA) or sense mRNA transcripts. In this manner, antisense nucleic acids usually function to inhibit mRNA transcription (i.e., for example, with a DNA antisense molecule) or protein translation (i.e., for example, with a mRNA antisense molecule) a the molecular level.

In regards to the present invention, antisense nucleic acids capable of specifically binding to gene sequences are known to be useful for interfering with gene expression. Brakel et al., "Modified Nucleotide Compounds" EU431523 A2. Although it is not necessary to understand the mechanism of an invention, it is believed that antisense CsrA mRNA can be used to modulate the ability of sense CsrA mRNA to bind to a ribosome, thereby preventing CsrA protein translation. For example, high levels of sense CsrA mRNA can be expressed to repress LOS-PC epitope display (i.e., for example, by delivery of CsrA sense mRNA via conjugated antibody). Then, to increase LOS-PC epitope display, an antisense nucleic acid can be provided (e.g., via a monoclonal antibody conjugate), which then hybridizes to sense CsrA mRNA.

The present invention encompasses compositions comprising a CsrA sense polynucleotide in combination with one or more CsrA antisense polynucleotides, homologues or mutations thereof. More preferably, the ratio of CsrA antisense polynucleotides to CsrA sense polynucleotides is greater than 5:1, preferably less than 50:1, most preferably around 18:1. However, this invention encompasses any ratio of CsrA antisense polynucleotides to CsrA sense polynucleotide, including by not limited to, for example, the ratios of 1:1, greater than 1:1, greater than 2:1, greater than 5:1, greater than 10:1, greater than 100:1, greater than 1000:1, greater than 10,000:1, greater than 100,000:1, or greater than 1,000,000:1. The invention also encompasses ratios of CsrA antisense polynucleotides to CsrA sense polynucleotides of 1:1, less than 1:1, less than 1:2, less than 1:5, less than 1:10, less than 1:100, less than 1:1000, less than 1:10,000; or less than 1:100,000. The combination of CsrA sense polynucleotide and CsrA antisense polynucleotides can be substantially pure of other components.

Alternatively, other components such as carbon sources of metabolism-regulating factors can be added to the combination. The combinations of the invention can comprise full-length CsrA sense polynucleotide or biologically active fragments or derivatives thereof which retain the ability to bind CsrA antisense polynucleotide, or full-length CsrA antisense polynucleotide or biologically active fragments or derivatives thereof which retain the ability to bind CsrA sense polynucleotide. The combinations of CsrA antisense polynucleotides and CsrA sense polynucleotides of the present invention can comprise CsrA antisense and CsrA sense polynucleotides bound to each other, unbound (free), in flux between bound and unbound states, or can comprise a mixture of bound and unbound molecules. The combinations of polynucleotides of the present invention can be coupled to a solid phase support, e.g., nitrocellulose, nylon, column packing materials (e.g., Sepharose beads), magnetic beads, glass wool, cells, or other substrates Experimental These examples present representative protocols used in describing the invention disclosed herein. These protocols are not to be considered limiting as any analogous or comparable protocol measuring the same end-points within the skill of an ordinary artisan would also be sufficient.

EXAMPLE 1

Standard Assay Techniques

*H. influenzae* Growth Conditions

The non-encapsulated Rd derivative of *H. influenzae* type d (BA042; *H. influenzae* Rd) was grown at 35° C. in Brain Heart Infusion agar or broth supplemented with 10 μg/ml nicotinamide adenine dinucleotide (NAD) and 10 μg/ml hemin (sBHI). Akerley et al. (2002). DNA was transformed into naturally competent *H. influenzae* prepared as previously described. Barcak et al. (1991). Kanamycin (Km; 20 mg/ml) and Tetracycline (Tet; 8 mg/ml) were added to sBHI.

Plasmid and *H. influenzae* Strain Construction

Standard molecular biology methods were used for plasmid construction, primer extension, Northern and Western blot analysis. Ausubel et al. (1995). Representative bacterial strains and plasmids sufficient to make and use the invention disclosed herein are presented in Table 3 below.

TABLE 3

Representative Bacterial Strains And Plasmids.

| Strains and plasmids | Relevant features | Source or reference |
| --- | --- | --- |
| Bacterial strains | | |
| BA042 | Non-encapsulated *H. influenzae* Rd; referred to as Rd or wild-type in this study | Akerley et al. (2002) |
| RlicA41 | Rd licA::magellan1; $Km^R$ | Disclosed herein |
| ZlicA | Rd licAΔCAAT$^a$::lacZ | Disclosed herein |
| Δrep | Rd licAΔCAAT$^a$ | Disclosed herein |
| ΔlicA | Rd ΔlicA::lacZ | Disclosed herein |
| Rhel-licA | Δrep lic1$^{Phel}$ | Disclosed herein |
| Δ8kan | Rd ΔcsrA::aphI; $Km^R$ | Disclosed herein |
| Plasmids | | |
| pXT10 | Delivery vector for chromosomal integration and expression at the xyl locus of *H. influenzae* contains xylF xylB xylA$^{\Delta 4-804}$ and tetracycline resistance cassette, tetAR | Wong et al. (2003) |
| pLic327 | pXT10 derivative containing a 327 bp PCR product of the 5' region immediately upstream of the licA coding sequence | Disclosed herein |
| pLic1 | pCR-BluntII-TOPO vector carrying 5.44 kb PCR product containing the lic1 operon | Disclosed herein |
| pLic1ΔZα | pLic1 containing a deletion of lacZ α from the pCR-BluntII-TOPO vector | Disclosed herein |
| pΔCAAT | pLic1 containing deletion of 16 tandem CAAT repeats and translational in-frame positioning of three potential licA ATG initiation codons | Disclosed herein |
| pΔCAAT2 | pΔCAAT containing deletion of lacZ α from the pCR-BluntII-TOPO vector | Disclosed herein |
| pZlicA | pLic1ΔZα containing *E. coli* lacZ expressed from the putative licA initiation codons | Disclosed herein |
| pZΔlicA | pΔCAAT2 containing replacement of the licA coding region with *E. coli* lacZ | Disclosed herein |
| pHel-licA | pΔCAAT2 containing Phel immediately upstream of the licA ORF | Disclosed herein |
| p814–812 | pCR-BluntII-TOPO vector carrying 3.8 kb PCR product containing wild-type csrA and flanking genomic regions | Disclosed herein |
| pΔ8kan | Deletion construct derived from p814–812 containing aphI $Km^R$ cassette from Tn903 in place of the csrA open reading frame | Disclosed herein |

$^a$Deletion of 16 of 17 CAAT repeats with in-frame positioning of three potential licA ATG initiation codons.

Plasmid pLic327 containing 5' sequences upstream of licA was amplified with primers licA5'1 and licAorfout2. The BamHI digested PCR product was cloned into a derivative of pXT10 containing *E. coli* lacZ (encoding β-galactosidase) and the aphI kanamycin resistance gene. Wong et al. (2003).

*H. influenzae* Rd. strain RlicA41 was isolated from an ordered mutant strain collection representing the genome of

*H. influenzae* Rd mutagenized with magellan1, a derivative of the mariner-family transposon Himar1 as described previously. Akerley et al. (2002).

*H. influenzae* Rd. strain Δrep containing a deletion of 16 tandem CAAT repeats in licA and an in-frame positioning of three potential licA ATG initiation codons was created as follows: i) a 5.44 kb product was amplified from *H. influenzae* Rd using primers HI1534-5' and HI1540-3'; ii) cloned into the pCR-Blunt II-TOPO vector (Invitrogen) to create pLic1; iii) pLic1 was used as template in PCR with primers, licAMout2 and licAΔrep to generate a ~8.9 kb product; iv) the ~8.9 kb PCR product was digested with StuI and recircularized to generate plasmid, pΔCAAT; v) pΔCAAT was transformed into a *H. influenzae* Rd derivative (strain ZlicA, infra) containing *E. coli* 21 lacZ translationally fused to licA immediately 3' of the licA ATG initiation codon γ; v) ZlicA was screened for white colonies on 5-brom-4-chloro-3-indolyl-beta-D-galactopyranoside (X-gal) plates to create strain Δrep.

*H. influenzae* Rd. strain ZlicA was created as follows: i) the *E. coli* lacZ gene was amplified with primers 5'Z-ATG2 and 3'Z-TAA; ii) the amplified product was digested with AscI and StuI and ligated to a ~8.5 kb PCR product of pLic1ΔZα (containing a deletion of lacZα; a pLic1 derivative); iii) pLic1ΔZα was amplified with primers licAMout2 and licAΔ-rep; iv) the PCR product was digested with MluI and StuI to create pZlicA; v) pZlicA was transformed into *H. influenzae* Rd to create strain ZlicA.

*H. influenzae* Rd. strain Rhel-licA, containing the native licA gene under the transcriptional control of the putative hel (HI0693) promoter was created as follows: i) pΔCAAT was digested with BsaI and NotI to remove lacZα; ii) the digest was subjected to Klenow end-filling and recircularization to generate pΔCAAT2; iii) pΔCAAT2 was used as template in PCR with primers licATG1 out and licATG1 in to generate a ~8.5 kb PCR product; iv) the ~8.5 kb PCR product was digested with SalI; v) the digest was ligated to an ~294 bp PCR product containing the putative hel promoter sequence amplified from *H. influenzae* Rd with primers hel5'ATGout and 692-5'ATGout; vi) the PCR product was digested with SalI to create plasmid pHel-licA; vii) pHel-licA was transformed into strain ZlicA; viii) strain ZlicA was screened for white colonies on X-gal plates to create strain Rhel-licA.

*H. influenzae* Rd. strain ΔlicA containing a licA deletion was created as follows: i) the *E. coli* lacZ gene was amplified as described above; ii) the PCR product was ligated to a ~7.6 kb PCR product amplified from template pΔCAAT2 with primers licAMout2 and licA3'ORF; iii) the ligated product was digested with MluI and StuI to create pZΔlicA; iv) *H. influenzae* Rd was transformed with pZΔlicA to create strain ΔlicA.

*H. influenzae* Rd. strain Δ8kan containing a nonpolar deletion of CsrA was created as follows: i) a 3.8 kb product was amplified from *H. influenzae* Rd using primers HI0814-5' and HI0812-3'; ii) the PCR product was cloned into the pCR-Blunt II-TOPO vector (Invitrogen) to create p814-812; iii) p814-812 was amplified using the primers, 8ATGout and 8TAGout to create an ~7 kb PCR product; iv) the ~7 kb PCR product was digested with StuI and SalI; v) the digest was ligated to a StuI and SalI digested PCR product containing the kanamycin resistance gene (aphI) isolated from Tn903 by amplification with primers MER5kanSDATG and MER3kanTAA to create pΔ8kan, Wong et al. (2003); vi) *H. influenzae* Rd was transformed with pΔ8kan to create strain Δ8kan.

*H. influenzae* Rd. strains disclosed herein were confirmed to contain the appropriate mutations by sequencing or PCR amplification across recombinant junctions of the respective mutations with the *H. influenzae* chromosome.

Western Blot Analysis

*H. influenzae* Rd was grown in sBHI at 35° C. to an $OD_{600}$=0.2-0.3 under standard cell culture aeration conditions in volumes ranging from 10 ml (aerobic culture) to 200-300 ml (microaerobic culture) contained within a 500 ml Erlenmeyer flasks and continuously shaken at 250 rpm. Unaerated cultures (i.e., anaerobic) were grown similarly except that 50 ml sealed tubes were used and were filled to capacity.

0.25 to 0.5 $OD_{600}$ units of either aerobic or unaerated cells were pelleted and resuspended in solution 21 (a component of the M-IV competence inducing medium, Barcak et al. (1991)) followed by addition of loading buffer containing 2-mercaptoethanol and boiled at 100° C. for 5 minutes.

Boiled whole cell lysates (0.1 to 0.25 $OD_{600}$ units) were separated by SDS-PAGE with 18% polyacrylamide gels and electrotransferred onto Immobilon-P (Millipore Corporation). Equivalent numbers of cells in whole-cell lysates were loaded in each lane. Equal loading was verified either by staining replicate gels run in parallel with Commassie Blue or by staining the upper ⅛th of the transferred blot with Ponceau S.

Immunoblotting was performed using a 1:10,000 dilution of anti-PC IgA mAb TEPC 15 (Sigma-Aldrich) and bands visualized using either anti-mouse immunoglobulin A conjugated to peroxidase or alkaline phosphatase (Rockland Immunochemicals).

To visualize the LOS, whole-cell lysates from 0.02 $OD_{600}$ units of cells were resolved by SDS-18% PAGE, stained with the fluorescent dye (Pro-Q Emerald 300; Pro-Q Emerald 300 Lipopolysaccharide Gel Stain Kit, Molecular Probes), and photographed using UV transillumination.

Northern and Primer Extension Analysis

Total RNA from *H. influenzae* Rd was obtained from cultures grown in sBHI to $OD_{600}$=0.3-0.4 under varied culture aeration conditions ranging from 10 ml to 200 ml and unaerated as described above. RNA was isolated using TRIzol Reagent (Invitrogen), treated with DNase I (Ambion) and phenol extracted.

For Northern blotting, 10 or 15 μg of total RNA was electrophoresed on a 1.5% agarose gel containing 1.1% formaldehyde and transferred to a Nytran nylon membrane (Amersham Pharmacia Biotech). Probes were generated by amplification from *H. influenzae* Rd using 5' and 3' primer pairs for licA (HI1537), licB (HI1538), licC (HI1539), licD (HI1540) and galU (HI0812).

PCR products were labeled with the Gene Images AlkPhos Direct Labeling Kit and signals visualized with CDP-Star chemiluminescent detection system (Amersham Pharmacia Biotech). Washing and hybridization conditions were performed according to the manufacturer's instructions. Primer extension analysis was performed on 20 μg total RNA from *H. influenzae* Rd using a [γ-$^{32}$P]-ATP (Amersham Pharmacia Biotech) labeled primer, licAorfout2, which is located 99 bp's 3' of the putative licA ATG start codon γ. (See FIG. 1C).

Products were analyzed by electrophoresis in a 7 M urea, 6% polyacrylamide gel. Sequence laddering was performed using the same [γ-$^{32}$P]-ATP labeled primer with plasmid pLic327 as a template (Sequenase 2.0, DNA Sequencing Kit; USB Corporation).

Microarray Analysis

Total RNA from triplicate cultures of *H. influenzae* Rd grown aerobically (10 ml in a 500 ml Erlenmeyer flask) or microaerobically (200 ml in a 500 ml Erlenmeyer flask) to $OD_{600}=0.3$ to 0.4 was obtained and treated with DNaseI as described above. RNA (8 µg) from each triplicate culture was used as a template for generation of cDNAs using random primers (New England Biolabs) followed by coupling to a fluorescent dye (Cy3, Amersham Biosciences) according to standard protocols (BD Atlas PowerScript Fluorescent Labeling Kit; BD Biosciences Clontech).

Fluorescently labeled cDNAs were used in hybridization on Corning UltraGAPS slides printed with the *H. influenzae* Genome Oligo set (Qiagen Operon) using a GMS 417 Arrayer (Affymetrix). The genome set contains 1,714 optimized 70 mer probes representing 1,714 *H. influenzae* Rd open reading frames and 12 unique negative control probes. Controls for cDNA synthesis and fluorescent label coupling were also printed onto each slide to ascertain the efficiency of these reactions using the reagents supplied with the BD Atlas PowerScript Fluorescent Labeling Kit.

The oligo probes were diluted in 50% dimethyl sulfoxide to a concentration of 40 micromolar and heated at 96° C. for 2 minutes prior to printing in triplicate onto each slide at a constant temperature of 22° C. and 40-50% relative humidity. Slides were hybridized at 42° C. in hybridization chambers (Corning) for 16 to 24 hours, washed and scanned using a GMS 418 Array Scanner (Affymetrix). Images were processed and hybridization signals quantified with ImaGene and GeneSight (BioDiscovery, Inc).

The total signal intensity for each gene was corrected by subtracting the local background, merging identical spots by obtaining the average signal intensity value from triplicate spots on the same slide, and normalized by dividing by the mean of the values for all the genes in the experiment. The corrected signal intensity for each gene represents the mean of triplicate samples from three independent hybridization experiments to Cy3-labeled cDNA's derived from independent cultures grown aerobically and microaerobically. Expression ratio data was generated by comparing the corrected mean signal intensity values from arrays hybridized to cDNA generated from aerobically versus microaerobically grown cultures.

Statistical analysis of the expression data was performed with the Cyber-T Bayesian statistics program from the Institute for Genomics and Bioinformatics at the University of California, Irvine. Genes whose expression ratios had Bayesian p values based on the regularized t test$\leq 0.01$ were considered to be significant in their fold induction.

Reverse Transcriptase-Quantitative PCR (RT-qPCR)

Quantification of licA and hel mRNA expression in *H. influenzae* strain Rhel-licA and *H. influenzae* strain Δrep grown aerobically (10 ml cultures) and microaerobically (200 ml cultures) was performed using the DyNAmo SYBR green qPCR kit (MJ Research) in quantitative real-time PCR measured with the DNA Engine Opticon II System (MJ Research).

Briefly, 0.5 µg of DNaseI-treated total RNA from strains Rhel-licA and Δrep, grown aerobically or microaerobically, was used as template in cDNA synthesis using SuperScript II reverse transcriptase (Invitrogen). licA cDNA was generated using primer licAmid3') while hel cDNA was generated using primer 693int3. 1/20th of the reverse transcriptase reactions was used as template in qPCR for amplification of licA (primers; licArep and licAmid3) and hel (primers, 693-5 and 693int3).

Real-time cycler conditions were as follows, a 95° C. incubation for 2 min followed by 39 cycles of i) 96° C. for 30 s; ii) 58° C. for 30 s; and iii) 72° C. for 1 min, followed by a 72° C. incubation for 7 min.

Fluorescence was read at 78° C. Control reactions were performed in parallel with mock cDNA reactions generated without reverse transcriptase. Samples were electrophoresed on agarose gels to confirm product sizes. A standard curve ($r^2 \geq 0.98$) was generated from a dilution series of wild-type Rd genomic DNA as template using each primer pair in a parallel set of reactions in qPCR.

Quantitation of mRNA expression of the hxuAC, dmsAC, nrfABCD genes from *H. influenzae* Rd wild-type was measured in real-time PCR assays essentially as described above, except random primers (New England Biolabs) were used to generate the cDNA templates used in qPCR. The 5' and 3' primer pairs used in qPCR are specific for hxuA (HI0264), huxC (HI0262), dmsA (HI1047), dmsC (HI1045), nrfA (HI1069), nrfB (HI1068), nrfC (HI1067), and nrfD (HI1066).

EXAMPLE 2

Aerobic Modulation of Phosphorylcholine (PC) Epitope Display and licA mRNA

This example presents data regarding whether redox growth conditions could affect *H. influenzae* glycosylated LOS-PC epitope display; a feature shared by LOS structures of non-typeable strains. Risberg et al. (1999); Cox et al. (2001); Mansson et al. (2002); and Mansson et al. (2003).

Validation of Aerobic and Microaerobic Redox Growth Conditions

To attain different aeration levels, the volume of shaken cultures was varied as previously described. D'Mello et al. (1997). An unaerated culture was generated using a sealed tube filled to exclude air. The effect of these conditions on redox responses in *H. influenzae* was defined by global expression profiling using a microarray procedure outlined in Example I. Three replicate cultures grown under aerobic redox growth conditions (i.e., for example, a 10 ml culture volume) and a microaerobic redox growth condition (i.e., for example, a 200 ml culture volume). (See FIG. 1A, Table 1 and Table 2).

Figure 2:
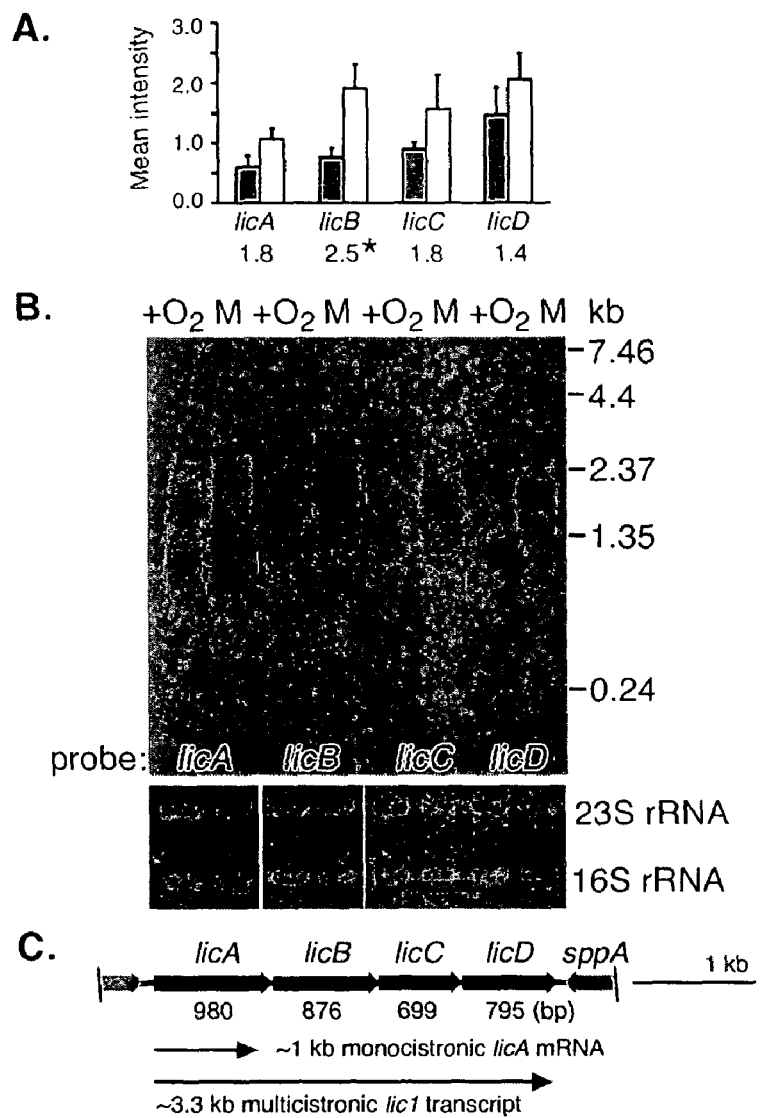
FIG. 2A shows exemplary data regarding differential expression of the lic1 putative operon containing a licABCD gene complex (i.e., for example, HI1537-HI1540). Each bar represents the signal mean intensity (y-axis) from 3 independent microarray experiments quantifying the expression level of a gene (x-axis) from cultures grown aerobically (crosshatched bars) and microaerobically (open bars). The fold induction is indicated underneath each gene. An asterisk represents an induction ratio with a p value≦0.01.
FIG. 2B shows an exemplary Northern blot containing H. influenzae Rd total RNA grown under either aerobic ($+O_2$) or microaerobic (M) redox growth conditions. Replicate blots from each redox growth condition were hybridized with probes specific to: licA (Lanes 1 & 2), licB (Lanes 3 & 4), licC (Lanes 5 & 6), and licD (Lanes 7 & 8). An ethidium bromide stained gel prior to transfer is shown in the gel directly below.
FIG. 2C depicts one embodiment of a genomic organization of the lic1 operon containing a licABCD gene complex with putative licA monocistronic and multicistronic transcripts locations illustrated directly below. The molecular weight sizes (bp) below each locus are the estimated gene lengths predicted from the whole-genome sequence.

An increased microaerobic expression of putative *H. influenzae* homologues of microaerobically-induced *E. coli* genes was detected including, but not limited to, genes encoding nitrite reductase (nrfABCD), dimethylsulfoxide reductase (dmsABC), and the hxuCBA genes that encode the heme-hemopexin uptake system (See FIG. 1A). Choe et al. (1993); and Cotter et al. (1989). Although it is not necessary to understand the mechanism of an invention it is believed that this latter result is consistent with *H. influenzae's* use of exogenous heme sources for aerobic growth. White et al. (1963); and Evans et al. (1974).

The above microarray results were confirmed by RT-qPCR (data not shown). Results from two experiments with cultures grown independently under the same conditions used for the microarray analysis showed aerobic induction of hxuA (2.5- and 3.5-fold) and hxuC (1.7- and 2.1-fold). Microaerobic induction of dmsA (22.5- and 8.8-fold), dmsC (11.2- and 5.9-fold), nrfA (19.4- and 10.5-fold), nrfB (10.6- and 6.5-fold), nrfC (10.3- and 4.3-fold), and nrfD (5.6- and 3.1-fold) was observed. These results provide validation of the culture conditions defined herein as aerobic and microaerobic.

Measurement of LOS-PC Epitope Display

To evaluate LOS-PC epitope display under varied redox growth conditions, Western immunoblotting of whole-cell lysates from cultures grown under a range of aeration levels was performed with monoclonal antibody (mAb) TEPC 15, which is highly specific for the PC epitope. (See FIG. 1B).

Control lysates from a mutant containing a mariner transposon insertion in licA exhibited no reactivity with anti-PC mAb, confirming the antibody specificity (FIG. 1B, lanes 1 and 2). In wild-type *H. influenzae* Rd, the LOS-PC epitope display was poorly expressed under aerobic conditions (10 ml volume). But under increasing microaerobic redox growth conditions, with maximal levels seen in cultures grown in 200 ml and 300 ml volume, LOS-PC epitope display progressively increased. (See FIG. 1B; lanes 7 and 8).

Because the licA gene is required for PC biosynthesis, modulation of PC epitope display might also be regulated by licA mRNA expression. A primer extension analysis using RNA isolated from wild-type *H. influenzae* Rd, grown under conditions of varied culture aeration, mapped a licA transcriptional start site to a distance of approximately 46 bp upstream of putative licA ATG start codon γ. (See FIG. 1C). The increased expression of licA mRNA transcripts containing a common 5' transcriptional start site correlated with increased culture volume (i.e., progressive microaerobic redox growth conditions), with the most abundant primer extension product seen in the 200 ml culture. (See FIG. 1C, lane 5).

In summary, these results indicate that redox growth conditions modulate *H. influenzae* LOS-PC epitope display and licA-hybridizing transcript expression in a similar manner. For example, an increased LOS-PC epitope display was observed concomitant with an increased expression of licA RNA primer extension products using microaerobic cultures as compared to highly aerated cultures. Although it is not necessary to understand the mechanism of an invention, it is believed that modulation of LOS-PC epitope display may be partially mediated through regulation of licA mRNA expression.

Based on these results, three growth conditions were used for subsequent experiments in the Examples below to examine a possible mechanism for LOS-PC epitope display modulation. For simplicity, these conditions will be termed aerobic ("+$O_2$", a 10 ml culture), microaerobic ("M", a 200 ml culture), and unaerated or anaerobic ("−$O_2$", a sealed 50 ml tube).

EXAMPLE 3

Microaerobic Redox Growth Condition Induction of Lic1 Transcript Expression

This example presents data showing LOS-PC epitope display modulation by the licABCD gene complex (i.e., lic1 operon) mediated by lic1 mRNA transcript expression changes in response to aerobic and microaerobic growth conditions. It is known that these mRNA transcripts may be present as predicted from the genomic DNA sequence. Fleischmann et al. (1995).

*H. influenza* Rd grown under aerobic and microaerobic conditions were subjected to the microarray procedures in accordance with Example I. The results showed a microaerobic induction of the licABCD gene complex in comparison to the aerobic condition. (See FIG. 2A).

Northern blot hybridizations with probes specific to each gene of the lic1 locus performed in accordance with Example I, further verified these results. (See FIG. 2B). Each probe detected RNA species of lengths consistent with sizes of monocistronic or multicistronic lic1 RNA transcripts. (See FIG. 2B and FIG. 2C). In each case (i.e., licA, licB, licC, and licD), the abundance of monocistronic RNA species detected by probes specific for each of the lic1 genes was markedly increased under microaerobic redox growth conditions; particularly with respect to the multicistronic transcripts.

EXAMPLE 4

LicA Phase Variation does not Modulate LOS-PC Epitope Display

This example presents data regarding LOS-PC epitope display modulation by licA gene phase variation in response to redox growth conditions.

LicA phase variation is believed mediated by slipped-strand base mispairing within tandem tetrameric repeats of a sequence 5'-(CAAT)$_n$-3' within the N-terminal coding sequence. Weiser et al. (1989). The *H. influenzae* strain Drep was created in accordance with Example I. Strain Drep contains a deletion of the CAAT repeats and also positions three licA ATG initiation codons in-frame to allow full-length translation from all three initiation codons.

Figure 3:
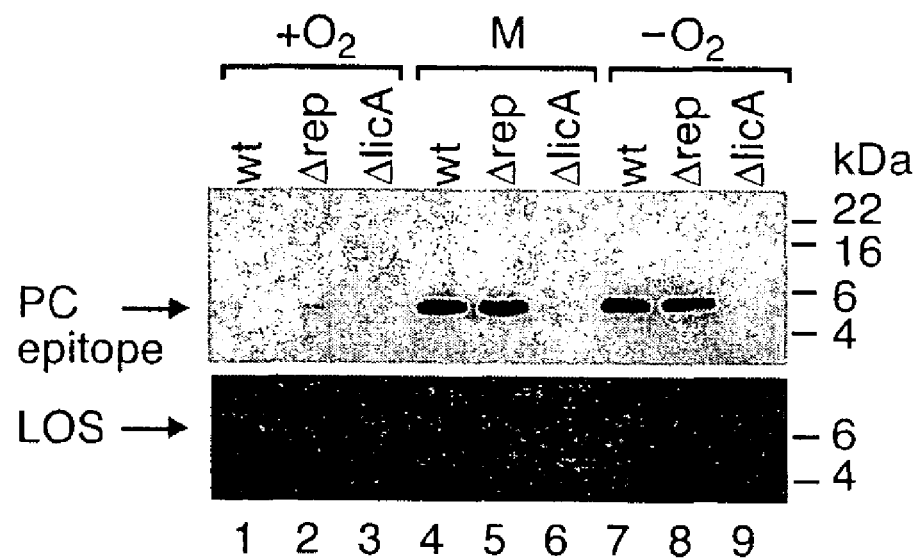
FIG. 3 demonstrates exemplary data regarding LOS-PC epitope display of the licA CAAT repeat deletion mutant of $H.$ $influenzae$ by Western blot of whole-cell lysates under varied redox growth conditions: +O2: 10 ml aerobic; M: 200 ml microaerobic; and −O2: unaerated. All samples were separated by SDS-18% PAGE and immunoblotted with anti-PC mAb. Lysates are from wild-type (lanes 1, 4, and 7), CAAT deletion strain, Drep (lanes 2, 5, and 8), and licA deletion strain, ΔlicA (lanes 3, 6, and 9). The panel below shows $H.$ $influenzae$ LOS from replicate samples stained with the fluorescent dye, Pro-Q Emerald 300 (Molecular Probes).

Western blot analysis was conducted to compare LOS-PC epitope display in strain Δrep versus wild-type *H. influenza* Rd strains. Control lysates extracted from a licA deletion strain (Strain ΔlicA, see Example I) did not react with anti-PC mAb. (See FIG. 3, lanes 3, 6, and 9). LOS-PC epitope display between wild-type *H. influenzae* Rd and Drep were similar under each redox growth condition. (See FIG. 3). These results indicate that the Drep mutation does not affect redox growth condition LOS-PC epitope display modulation.

Fluorescent staining, performed in accordance with Example I, of a replicate gel that detects LOS carbohydrate structure revealed no appreciable differences between wild-type and Drep strains. This data indicates that changes in total LOS production does not account for the modulation of the LOS-PC epitope display. (See FIG. 3, bottom panel).

In summary, phase variation of licA is not the exclusive means of regulating LOS-PC epitope display because CAAT repeat deletion did not abrogate modulation of this phenotype. Furthermore, a phase-locked Δrep strain displaying redox growth condition regulation of LOS-PC epitope display that is identical to wild-type *H. influenzae* Rd is useful as a negative control by removing a mechanism that can spontaneously turn off PC production.

EXAMPLE 5

LicA mRNA Overexpression does not Restore Aerobically Decreased LOS-PC Epitope Display This example presents data regarding LOS-PC epitope display modulation by licA mRNA overexpression in response to redox growth conditions.

LOS-PC epitope display and associated lic1 transcript levels are similarly influenced by redox growth conditions. (See Example 3). This example investigates whether licA mRNA regulation mediates LOS-PC epitope display. Although it is not necessary to understand the mechanism of an invention, it is believed that if decreased expression of licA mRNA under aerobic redox conditions also accounts for decreased LOS-PC epitope display, then increasing expression of licA mRNA under aerobic redox conditions will also cause an increased LOS-PC epitope display.

The *H. influenzae* strain Rhel-licA was engineered according to Example I. In strain Rhel-licA the native licA gene is under the transcriptional control of a strong promoter from the hel gene (The Institute for Genomic Research, TIGR locus HI0693). Rhel-licA contains the hel promoter immediately 5' of three in-frame potential licA initiation codons and an in-frame deletion of the CAAT repeat units. The hel promoter was demonstrated by Northern analysis to result in a high expression rate (data not shown).

Total RNA was extracted from strain Rhel-licA grown under either aerobic or microaerobic redox growth conditions. Reverse transcriptase quantitative real-time PCR (RT-qPCR) assessed the level of abundance of licA-specific mRNA transcripts in accordance with Example I. Control reactions using primers specific for the hel gene verified that equivalent amounts of RNA were analyzed for each strain.

Using primers specific for licA, the RT-qPCR conversion of mRNA to cDNA was compared between the Rhel-licA strain and parent Δrep strain. Under aerobic conditions, Rhel-licA showed an ~7.5-fold induction over Δrep. (FIG. 4A, column 2÷column 1). Under microaerobic conditions, Rhel-licA showed a ~13-fold increase over Δrep. (FIG. 4A; column 4÷column 3). Despite the licA mRNA induction, a Western blot analysis demonstrated that LOS-PC epitope display was not concomitantly increased in the Rhel-licA strain under either aerobic or microaerobic redox growth conditions. (See FIG. 4B, comparing columns 1 & 2, and comparing columns 3 & 4). Specifically, the ~7.5-fold Rhel-licA licA mRNA increase under aerobic redox growth conditions was not mirrored by increased LOS-PC epitope display and the ~13-fold Rhel-licA licA mRNA increase under microaerobic redox growth conditions was not mirrored by increased LOS-PC epitope display.

REFERENCES

Akerley et al. "A genomescale analysis for identification of genes required for growth or survival of Haemophilus influenzae" Proc Natl Acad Sci USA 99:966-971 (2002).

Ausubel et al, (eds) Current Protocols in Molecular Biology. New York: John Wiley & Sons, Inc., (1995)

Barcak et al. "Genetic systems in Haemophilus influenzae" Methods Enzymol 204: 321-342 (1991).

Begley et al. "Thiamin biosynthesis in prokaryotes" Arch Microbiol 171:293-300 (1999).

Bouchet et al., "Host-derived sialic acid is incorporated into Haemophilus influenzae lipopolysaccharide and is a major virulence factor in experimental otitis media" Proc Natl Acad Sci USA 100: 8898-8903 (2003).

Campagnari et al., "Lipooligosaccharide epitopes shared among gram-negative non-enteric mucosal pathogens" Microb Pathog 8:353-362 (1990).

Chatterjee et al., "Inactivation of rsmA leads to overproduction of extracellular pectinases, cellulases, and proteases in Erwinia carotovora subsp. carotovora in the absence of the starvation/cell density-sensing signal, N-(3-oxohexanoyl)-L-homoserine lactone" Appl Environ Microbiol 61: 1959-1967 (1995).

Choe et al., "Identification of the regulatory sequence of anaerobically expressed locus aeg-46.5" J Bacteriol 175: 1165-1172 (1993).

Compan et al., "Interaction of six global transcription regulators in expression of manganese superoxide dismutase in Escherichia coli K-12" J Bacteriol 175:1687-1696 (1993).

Conley et al., "Lack of IgA subclass restriction in antibody response to phosphorylcholine, beta lactoglobulin and tetanus toxoid" Immunology 53: 419-426 (1984).

Cotter et al., "Oxygen, nitrate, and molybdenum regulation of dmsABC gene expression in Escherichia coli" J Bacteriol 171:3817-3823 (1989).

Cox et al., "Structural analysis of the lipopolysaccharide from the nontypable Haemophilus influenzae strain SB 33" Eur J Biochem 268:5278-5286 (2001).

Cui et al., "Identification of a global repressor gene, rsmA, of Erwinia carotovora subsp. carotovora that controls extracellular enzymes, N-(3-oxohexanoyl)-L-homoserine lactone, and pathogenicity in soft-rotting Erwinia spp." J Bacteriol 177:5108-5115 (1995).

Cunningham et al, "Co-regulation of lipoamide dehydrogenase and 2-oxoglutarate dehydrogenase synthesis in Escherichia coli: characterisation of an ArcA binding site in the lpd promoter" FEMS Microbiol Lett 169:403-408 (1998).

D'Mello et al., "Role of bacterial Mn-cofactored superoxide dismutase in oxidative stress responses, nasopharyngeal colonization, and sustained bacteremia caused by Haemophilus influenzae type b" Infect Immun 65:2700-2706 (1997).

Ehrlich et al., "Mucosal biofilm formation on middle-ear mucosa in the chinchilla model of otitis media" JAMA 287:1710-1715 (2002).

Evans et al., "Haemin and nicotinamide adenine dinucleotide requirements of Haemophilus influenzae and Haemophilus parainfluenzae" J Med Microbiol 7:359-365 (1974).

Fleischmann et al., "Whole-genome random sequencing and assembly of Haemophilus influenzae Rd." Science 269: 496-512 (1995).

Greiner et al., "Nontypeable Haemophilus influenzae strain 2019 produces a biofilm containing N-acetylneuraminic acid that may mimic sialylated O-linked glycans" Infect Immun 72: 4249-4260 (2004).

Heeb et al., "Regulatory RNA as mediator in GacA/RsmA-dependent global control of exoproduct formation in Pseudomonas fluorescens CHA0" J Bacteriol 184:1046-1056 (2002).

Herbert et al., "Aerobic growth deficient Haemophilus influenzae mutants are non-virulent: implications on metabolism" Int J Med Microbiol 293:145-152 (2003).

Herbert et al., "Signature Tagged Mutagenesis of Haemophilus influenzae identifies genes required for in vivo survival" Microb Pathog 33:211-223 (2002).

Hood et al., "Use of the complete genome sequence information of Haemophilus influenzae strain Rd to investigate lipopolysaccharide biosynthesis" Mol Microbiol 22:951-965 (1996a).

Hood et al., "DNA repeats identify novel virulence genes in Haemophilus influenzae" Proc Natl Acad Sci USA 93:11121-11125 (1996b).

Hood et al., "Sialic acid in the lipopolysaccharide of Haemophilus influenzae: strain distribution, influence on serum resistance and structural characterization" Mol Microbiol 33: 679-692 (1999).

Lawhon et al., "Global regulation by CsrA in Salmonella typhimurium" Mol Microbiol 48:1633-1645 (2003).

Leon et al., "Specificity for phosphorylcholine of six murine myeloma proteins reactive with Pneumococcus C polysaccharide and beta-lipoprotein" Biochem 10: 1424-1429 (1971).

Lynch et al., "Transcriptional control mediated by the ArcA two-component response regulator protein of Escherichia coli: characterization of DNA binding at target promoters" J Bacteriol 178:6238-6249 (1996).

Ma et al., "Molecular characterization of global regulatory RNA species that control pathogenicity factors in Erwinia amylovora and Erwinia herbicola pv. gypsophilae" J Bacteriol 183:1870-1880 (2001).

Macfadyen et al., "Life in mucus: sugar metabolism in *Haemophilus influenzae*" *Res Microbiol* 147:541-551 (1996).

Mansson et al., "Structural analysis of the lipopolysaccharide from nontypeable *Haemophilus influenzae* strain 1003" *Eur J Biochem* 269:808-818 (2002).

Mansson et al., "Structural diversity in lipopolysaccharide expression in nontypeable *Haemophilus influenzae*. Identification of L-glycero-D-manno-heptose in the outer-core region in three clinical isolates" *Eur J Biochem* 270:610-624 (2003).

Marra et al., "*Streptococcus pneumoniae* causes experimental meningitis following intranasal and otitis media infections via a nonhematogenous route" *Infect Immun* 69:7318-7325 (2001).

Moxon et al. In: *Mandell, Douglas, and Bennett's Principles and Practices of Infectious Diseases*. New York: Churchill Livingstone (2000).

Murphy et al., "Biofilm formation by nontypeable *Haemophilus influenzae*: strain variability, outer membrane antigen expression and role of pili" *BMC Microbiol* 2:7 (2002).

Nesper et al. "Characterization of *Vibrio cholerae* O1 E1 tor galU and galE mutants: influence on lipopolysaccharide structure, colonization, and biofilm formation" *Infect Immun* 69:435-445 (2001).

Pessi et al., "The global posttranscriptional regulator RsmA modulates production of virulence determinants and N-acylhomoserine lactones in *Pseudomonas aeruginosa*" *J Bacteriol* 183: 6676-6683 (2001).

Rioux et al., "Isolation and characterization of mini-Tn10 lipopolysaccharide mutants of *Actinobacillus pleuropneumoniae* serotype 1" *Can J Microbiol* 45:1017-1026 (1999).

Risberg et al., "Structural analysis of the lipopolysaccharide oligosaccharide epitopes expressed by a capsule-deficient strain of *Haemophilus influenzae* Rd" *Eur J Biochem* 261: 171-180 (1999).

Romeo et al., "Identification and molecular characterization of csrA, a pleiotropic gene from *Escherichia coli* that affects glycogen biosynthesis, gluconeogenesis, cell size, and surface properties" *J Bacteriol* 175:4744-4755 (1993).

Romeo, T. "Global regulation by the small RNA-binding protein CsrA and the non-coding RNA molecule CsrB" *Mol Microbiol* 29:1321-1330 (1998).

Sabnis et al., "Pleiotropic regulation of central carbohydrate metabolism in *Escherichia coli* via the gene csrA" *J Biol Chem* 270:29096-29104 (1995).

Schweda et al., "Characterization of the phosphocholine-substituted oligosaccharide in lipopolysaccharides of type b *Haemophilus influenzae*" *Eur J Biochem* 267:3902-3913 (2000).

Shao et al., "Overexpression and biochemical characterization of beta-1,3-N-acetylgalactosaminyltransferase LgtD from *Haemophilus influenzae* strain Rd" *Biochem Biophys Res Commun* 295:1-8 (2002).

Shaw et al., "Natural antibodies with the T15 idiotype may act in atherosclerosis, apoptotic clearance, and protective immunity" *J Clin Invest* 105:1731-1740 (2000).

Sundararajan et al., "Biochemical observations on *E. coli* mutants defective in uridine diphosphoglucose" *Proc Natl Acad Sci USA* 48:2187-2193 (1962).

Swords et al., "Non-typeable *Haemophilus influenzae* adhere to and invade human bronchial epithelial cells via an interaction of lipooligosaccharide with the PAF receptor" *Mol Microbiol* 37:13-27 (2000).

Valverde et al., "RsmY, a small regulatory RNA, is required in concert with RsmZ for GacA-dependent expression of biocontrol traits in *Pseudomonas fluorescens* CHA0" *Mol Microbiol* 50: 1361-1379 (2003).

Vander Horn et al., "Structural genes for thiamine biosynthetic enzymes (thiCEFGH) in *Escherichia coli* K-12" *J Bacteriol* 175: 982-992 (1993).

Weilbacher et al., "A novel sRNA component of the carbon storage regulatory system of *Escherichia coli*" *Mol Microbiol* 48: 657-670 (2003).

Weiser et al., "The molecular mechanism of phase variation of *H. influenzae* lipopolysaccharide" *Cell* 59:657-665 (1989).

Weiser et al., "Decoration of lipopolysaccharide with phosphorylcholine: a phase-variable characteristic of *Haemophilus influenzae*" *Infect Immun* 65:943-950 (1997).

Weiser et al., "Phosphorylcholine on the lipopolysaccharide of *Haemophilus influenzae* contributes to persistence in the respiratory tract and sensitivity to serum killing mediated by C-reactive protein" *J Exp Med* 187:631-640 (1998).

Weissborn et al., "UTP: alpha-D-glucose-1-phosphate uridylyltransferase of *Escherichia coli*: isolation and DNA sequence of the galU gene and purification of the enzyme" *J Bacteriol* 176: 2611-2618 (1994).

White et al., "Hemin Biosynthesis in *Haemophilus*" *J Bacteriol* 85:842-850 (1963).

Wong et al., "Inducible expression system and marker-linked mutagenesis approach for functional genomics of *Haemophilus influenzae*" *Gene* 316:177-186 (2003).

Yang et al., "Coordinate genetic regulation of glycogen catabolism and biosynthesis in *Escherichia coli* via the CsrA gene product" *J Bacteriol* 178:1012-1017 (1996).

We claim:

1. A method, comprising:
   a) providing;
      i) a bacteriophage capable of infecting an *H. influenzae* cell, wherein said bacteriophage comprises an oligonucleotide sequence complementary to a portion of the coding region of a wild type CsrA gene of said *H. influenzae*; and
      ii) one or more of said *H. influenzae* cells comprising said wild type CsrA gene, wherein said one or more *H. influenzae* cells have colonized a host animal; and
   b) contacting said cells with said bacteriophage under conditions such that said oligonucleotide sequence hybridizes to said portion of the coding region of a wild type CsrA gene, wherein expression of said *H. influenzae* wild type CsrA gene is reduced.

2. The method of claim 1, wherein said host animal is a human.

3. The method of claim 1, wherein said oligonucleotide is completely complementary to said portion of said coding region.

4. The method of claim 1, wherein said oligonucleotide is between 15 and 30 bases in length.

5. The method of claim 1, wherein said bacteriophage is selected from the group consisting of HP1, HP2, S2A, B, C, N3, and ɸflu.

* * * * *

UNITED STATES PATENT AND TRADEMARK OFFICE
CERTIFICATE OF CORRECTION

| | | |
|---|---|---|
| PATENT NO. | : 7,838,502 B2 | |
| APPLICATION NO. | : 11/123761 | |
| DATED | : November 23, 2010 | |
| INVENTOR(S) | : Akerley and Wong | |

It is certified that error appears in the above-identified patent and that said Letters Patent is hereby corrected as shown below:

Col. 1, Line 7 - 9, should read;
-- GOVERNMENTAL SUPPORT

This invention was made with government support under Grant No. AI049437 awarded by the National Institutes of Health. The government has certain rights in the invention. --.

Signed and Sealed this
Eighteenth Day of January, 2011

David J. Kappos
*Director of the United States Patent and Trademark Office*

SEQUENCE LISTING

```
<160> NUMBER OF SEQ ID NOS: 12

<210> SEQ ID NO 1
<211> LENGTH: 192
<212> TYPE: DNA
<213> ORGANISM: Haemophilus influenzae

<400> SEQUENCE: 1
atgttaatct taactcgtaa agttggcgaa agtgtactta ttggagatga tatttctatc      60
acggttttga gtgtacgtgg aaaccaagtt aaactcggtg ttgaagcgcc taaagaagta     120
tccgttcacc gagaagaaat ttaccaacga attaaacaaa cgaaagatga accctattta     180
```
ggttcctctt ag    192

<210> SEQ ID NO 2
<211> LENGTH: 63
<212> TYPE: PRT
<213> ORGANISM: Haemophilus influenzae

<400> SEQUENCE: 2

Met Leu Ile Leu Thr Arg Lys Val Gly Glu Ser Val Leu Ile Gly Asp
1               5                   10                  15

Asp Ile Ser Ile Thr Val Leu Ser Val Arg Gly Asn Gln Val Lys Leu
            20                  25                  30

Gly Val Glu Ala Pro Lys Glu Val Ser Val His Arg Glu Glu Ile Tyr
        35                  40                  45

Gln Arg Ile Lys Gln Thr Lys Asp Glu Pro Tyr Leu Gly Ser Ser
    50                  55                  60

<210> SEQ ID NO 3
<211> LENGTH: 31508
<212> TYPE: DNA
<213> ORGANISM: Haemophilus phage HP2

<400> SEQUENCE: 3
cttcctcccc cgccgaattt acgttaaaaa tttgtgtttt tcagttagaa tttcaaaata    60
aaaattaatc taacttattg aagtaaaaga gatcattaat gcaactgaat agagatctta   120
actgtaaaaa tttcaatctt tttcatcatt tttcacttaa aatagatcat tgataataag   180
aataacaaga taacctaatg attttttaaat tgttttaaaa ttttccgtgt gaaatatgag   240
agtaattgat ttcagttaat tgactggcgg ttatcgccat tgtttaaaga taggtttaaa   300
agtaaagata aaaactagat atttataacc gccactttgt cgccagttga atattattgg   360
tgggtcgtga aggattcgaa ccttcgacca acggattaaa agtccgctgc tctaccgact   420
gagctaacga cccaattaga tgattttaaa gtaaatttta aaatctttgg attggtgttt   480
aaatggtgcc cgaagccaga cttgaactgg cacgcctcga aaggcgaggg atttttaaata  540
ccatagttaa accagtataa acaataactt atagcaacat taattgcttg ctcgtgcaaa   600
taagggcata taaggtaaa tataagacag aaccgccagc caatcgccag taaaatagag    660
gaaaaagtac aagggatttt ttgaaaaaca atcccttttt actgtgcagg attagaaagc   720
gggttgaatt tgaccgcact ttctaagtgc gaaggggcga agtgcgcata acgcatcgtc   780
atttcgatag ttgaatgacc gaggatttct ttcaacacta aatattccc accgttcatc    840
ataaaatggc tggcgaacgt atggcgcaaa acgtgggtta gttgccctt gggtaactca    900
atttcagcac gcaaaacagc atttttcaaag gattcgtaag catcattgaa taatctgcca   960
cgcttttcg gtagcatatc gaacaattct ttactgatcg gcacggtcct attttttcttt  1020
gatttcgtat tcacgaacgt gatttatac ggcataactt gtgattgggt cagtgttttcc  1080
gcctcactcc aacgtgcacc agttgccaaa caaattcgta caatcaagcc caaatcaggg  1140
ttgcgggagt tatcgcactc agctaataaa cggtaaatat cccgctcata taaaaacgct  1200
agttctgttt ctcgttcttt aaataagcgc acaccgtcaa ggggattttc agctgtccac  1260
tttcgcaatg atttcagttc gttaaacacc gcccgcaaat aagcgtgttc acggtttact  1320
gtggcttctt tcgggggatt gtttttattt accgaaaatt ccccatcaag gcggcgtttg  1380
cggtagtcgg caaagatttc agcgttaaat tcattggcag gcggatcgcc caagttcgcg  1440

```
cacaagttct ttagtttggc taaacgtgcc tcaccgtctg acaacgtttt accgtgcaaa    1500
tcaaaccatt cctgcacata aaacttaat gcgggcaagt cgcttgattc caaaacttgt    1560
acggaatcaa ccgcacttgt cgtttgttct ttggcttgat tgtaaaaacg tagcgcatcg    1620
cctttggtta aaaccatttt gcgtaaccgc ttgccgttta cataaacttc cgcaagccat    1680
ttaccgtttt ttgtgtcttt gcgaactgcc attactcaac ttcaggaaat ttaggtaaag    1740
atttaaacca ctcttacca tatttatcaa taagtgtttt catgtgggcg tcaagatcat    1800
ttgattcttt acttttagtc ttagggtaaa attttgattt ctttatatta tccatattgc    1860 agtttttac atcattttca caactttat taagaacatc atcgggaaaa tcagttgcta    1920
tgagcgacag catacccctcc atttgtgatt ggggtttata atcctggcta tctgccttta    1980
acaaattttc tttatggga tttaagattt tatctaagaa ttgttcggta aatatgcatt    2040
gattaaaact aagcgaatct aaagaaaact catcaaactt acacatcaaa tcaacagtat    2100
cgttctttga taattctaaa attttaggat ctttctcatt gactttaaaa tgagcacttc    2160
caatcattga atttttatt tttgatatga taaaggcgtt gccaaaagca tcttctttaa    2220
tctgattaat ggttgttttt attctcaaat ttttatcttt atattttta ttagctgcca    2280 attcattatt tgtatagtct gaataaattt catctaccga taaaacattg ccagaaacat    2340
ggcttttatt actcttcaat acataattct taaaatattc aagagaattg ctaataaaaa    2400
gttctttaga atggctgaac gctaatatag agttggaaga aatgaggatt aaaacaagca    2460
aaaatatttt acgcatatta tttacctatc ttctacaaat ctgtttagaa cgagaaaccg    2520
atccatcatt acaaataaac ttgccaccgg aacaatgcga aacgccgcct tttttacctg    2580
agcaaggctc acgcccacgc gcatctgcca tattggcaac cataaagaat gagcttgcaa    2640
ttaaaactgt tgaattaat ttttcatta cattttctcc attttaagaa tcaccttccc    2700
caccacatca atatcactca attcacattc aaaactgaat ttgccaccgt ccacacggat    2760
ttttcctgca ggtaacacag tgatataacg gataagatgg gagttttcga cgatgacgaa    2820
gtattcgcca tccactaaat tgccgtaatc gctagtggca aagtaggtgc gattgtcttc    2880
atcaatacga aacactttgt cataactttc acggctgtct aaattcggta agtaaggcaa    2940
aagaaagggt ttattttcca ttatgaaaga ttttccgctt tctagcttta ttgcatgaaa    3000
atatttcagg tagtctgaat tatcgaaaat cggctcattt ccataggcca cataatccaa    3060
tcttgcgccc gtttctttca cgcaacggat cactaattct gcagggaaaa aaccacgttt    3120
agcccaagtg ccaaaggtac tgtgaggcat tccaagatgt tcagctaata attttctatt    3180
cgcaaaacca tacgcttcca ttatgcgaga ataacatcc ttgccaccga taaattcttt    3240
catttagcaa attgacctta atattttat tgacagggtc aaatgacccg aagtatattt    3300
aaggggtcaa atgacccaaa ggtaatatat accattattt acagatggag gagtttaagc    3360
aatgaacggc caaatgcaa tttgtataaa tgtacagatc cacgcgcctt acgtcacgtt    3420
gaagaaatat gctgagctta ctgggctttc gttagacaaa gtgcgaaaga tgagagcggc    3480
aggcgaactg cctattgcag ataaaaaagc ggaaagaggt tcagtgttag tgaatttaat    3540
cgcgattgcc aaacaggcgg caaaacaaga ataaaaaacc acacaaaagt gcggtcacaa    3600
aaaacaaggt ttttgaacg ttggctatgc caacggctgc gaagcagcga acaatcctta    3660
caaggattgt gagtaatttc caaaagattt tagttataag gggaagacaa tgactaaatc    3720
atcattcacg tttttctttc aagaatattg cgagaaacac aatttaacca acgaagaaat    3780
tcaagaaaga ttcgctattc ttcagtatca ggcagaagtc gagcgagata ccactcaaga    3840
```

```
tcatcagcag ctttcggcga ttttttgcgaa atggcgtgaa aactgcccac gcaaacaagc    3900
taataacgat gagacaactt cccaatatac gggagcagaa catcaagcaa ttcgggattt    3960
gtttgcttca ctgaagcaat cagtgcgtga agctcattct ctacatcatc aatcacatca    4020
gggtgacgtg caagtccacg caaaaggcaa cccatcacgc gttcttgaag tgccagttgt    4080
aaatgctgct gatgaatctg tgcttgcata tcttgaagcg ttttttgcat ctgatcgttc    4140
atcttctgaa ctccttaaat taagtaatcg tttattcaat ttagggcaag catacaacaa    4200
aacaggtaaa taaaaaagcg agggcgcggc aatgtatgtg tctgaaaacg aaagtgcggt    4260 agaaaatgg catcgtttaa acggtgtgcc catgtcgaaa gcaagaaata gcgaagaaac    4320
cttgcatgaa atgggcttga gtaaatatcc cactgaacgc gcttttaatc atctttccga    4380
tgagcaaaaa ggcatgttaa aagcgttagc agatattgaa ccttttgaag attacatctc    4440
gcccgatctg actggcgata agttatggca ttacaacgaa aaaggcattg ataaattaac    4500
caaagcattt cacgccatgt cagcacttcg cacgccttt ccgcacgctt taacccgtcg    4560 tgattttttac aatatcgacc cacacacaag ggggaaataa tggcaacgaa aaaccgaacc    4620
attatcaaaa aatatgctga tcgctggcac aaagaagcct gtcatttata cgcaaaatgg    4680
ctcaacgcaa aacgccaagg cgatgaagaa gccgcaaatt attatttcag caaatatatt    4740
acggctggag acaactggat caactacacc aaatttgccc attaaggaaa actcttatgc    4800
aagaacacat tattgattta tctgaacgtt atgcccttaa gttaaacgaa aaccacgttt    4860
atatcctgta caaaattgaa ctcaatgaaa acggcactta tcagcgcaaa ggcggcgcag    4920
tatgtaagga tttaccttcc ttgttggaca agctgattta ctgtgaattg atgaatgaga    4980
aagtagaaac tcttgaagat atgcgcaacg tgctacacgc cattcacagc gaagtaacac    5040
gcatcgccga aattcaagcc acttatgcac aggcataaac cctttttttac ccatatctat    5100 taatttaatt catacaaaat aaatatttat gactaaattt aatctagagc aagcattaca    5160
aggtgcgcca gtccgtctta acaacggttt taaagcttat attttttgcgg atgtgagctt    5220 gcttgctatt aatgaaccat acccactgat tggcggatat gcctattcga tcagttcatt    5280
ttacgacaat caagaacatc aacgatttga agaatgccgt tgggcaaaag acggcaaatg    5340 tgatcgtttta agcgcattag ggtcgattgc tgggatgtgg aagattagc tatgcaatca    5400 atgtgggaac aacaacgcaa caacaacctc actgccaaaa atgcacacat ggcggtggtt    5460
gcctgtgaac gttatcaagc cgcagaaaat gggcataaat ttgaccgcac tttactgcct    5520
tttgatgaaa gctgctatac gccactacag ctagaattat tcgccacaaa ccctgttgat    5580
tttgagttta tcgaacaaaa acttgaaaac ctcccacgcc aacgtcagcg tgaatatttc    5640
cgtaaacttt atcttaaagc ctatcgctct gtaaaagacg atggctcgat tgtgttttgcc    5700 ctcggcaata acaacgtcg atatgccaat gattatttgc gcaatgtatt agatgtgcgt    5760
ttacaaaaag tcttttcaca atacaacgtg aacgtagatt ttttgcaagc gttcatcaac    5820
accccacaat ggttgttatc tgtcaaagat gaaatgcaac aagccgtgca gttctccacc    5880
gtaccaaccc gtgaagaact tgccaaacac tacaacgaat tacattacag cggttttcat    5940
tttcgactgt taggcaccca acaaaagcaa aaacaattac ctttctatttt aatcaccgaa    6000 agcaaattga aaaaaatggc gtatgaaatg gcaacggcat ttattcgatt tcaatgtgat    6060
tgctcccact ttttaaaaaa tggcatcgaa aaagacaacg agggcgacat tcaaggctat    6120
ttctatcagc tctataaatg gtgtggcgaa atcgcctttt ctgcaggttt caaaatccct    6180
```

-continued

```
cactgggaaa aaatagaaaa tgacaaacgc atcaaagccg aacatattga tagcacttta      6240
attcgcttga cgtgcgaaaa atggtggttt aagcaaatgc gagacataca aaaacgtatg      6300
gtcgagcata tcgctattgc ctgtggcgag gtgcgcgcca atgccgccag ttatatctct      6360
aatcaaagtt tccaagaatg gcaactgcaa caacgcaaga atcacgatta cttgcgtgcg      6420
atgattattg agaacatcga caacccagaa gaacaggtcg agcttttcga catgttcttg      6480
aaatcatctt ctaacccagc attacgcaga aatgaaatga tggtgcgctt gcgtggtttg      6540
gaagagtggg cagaagaaaa caacaatgaa gccttatttt taaccctcac tgcgccatca      6600
tcattccacg caggaaacgg caataagaaa tggttggggg tgaatccacg cgagacacaa      6660
aattatctaa acaaagtgtg gcaacagttc cgtgcgttat tgtcgaaacg taatattaaa      6720
ttttacggta tgcgagtggc agagccgcac aaagacggca cgccacactg gcatgcgcta      6780
gcttatgtgc cagcagaaca taaagaagaa gtcatccgct tatttaaaca aaaagcccta      6840
gaattagacg gcaatgaaaa aggcgcagca gaacaccgct gcaaagtgga aaaatgcgac      6900
aaaacaaaag gcagcgcaac ggcgtacatt gccaaataca ttgcgaaaaa tattgacggt      6960
tttgcccttg ctggcgaagt gtcagatgaa gacccgacac taagcctaca cgacaatgcc      7020
ttgcgtgttc gtgcatgggc gagccgttgg ggcattcgtc agttccaatt ctacggcggc      7080
gcatccattt gtgtttggcg tgaattgcgc cgattaatca gcggtcaagc cgatgatgaa      7140
attatcaata aagcccaagc agccgcaggc atcgcgaatg actatgcggc atatatggaa      7200
attcaaggtg gtgcgcttgc taaacgtgct gatcaaccta tcaagctcga ttatgaaact      7260
aaacctgcta ataaatatgg cgaacaacgc aaagccatta ttggtttagc gaatagattc      7320
agcctaaaac aagtcatttc acgcaccaaa aaatggcaaa ttaaaaaacg cccacaagat      7380
tttgcacaac gcacagaatc tatggttgag cgtagctcaa ccgctaacaa tagcgcacgc      7440
agtgcgcctt ggacttgtgt cagtaactgt aaccgctcaa atcttgagca aaagatcaaa      7500
ttactgacac aaccgatctg cacaccactt agcgcacaaa aattagacta tttattcaag      7560
tataaacggc taaccataga taatatataca gccttagaac tcaccgaaaa cgatgtgcag      7620
ttagtgaaac ggaatcaaaa catgatgacg tcccttccc ctgtgccaag aaaccttcaa      7680
aaactcaaaa attttcataa aaaacaacgt attcaatagg agaaaacgca atgaataaaa      7740
gaaaacagaa acaaatcagc cgaatcttag cagcaaaacg tgtaaaaaag tgcggtcaaa      7800
ttgatctgaa aaatttacaa gcgcaagtct gggatcttgc tgtgcaatcg caacaaaccg      7860
caagttgggt aaaaacacaa ggcgaaacta atcgtcttat ttgtcgctat ttttcaaaag      7920
aaatagaacg gcttgagcaa cgtaatatgc ctggttattt tgaattaatt ctgcttgcga      7980
ttgctgcagg gtttatcggt ggtgtagtgg gtcttttttc gtggttatta gcaattcttt      8040
gagtaaaaat aatgaacaaa tccaatacca aaaaatcaga taaagactta tgggcgacac      8100
cttggtgggt tttccattat gcagaacaat atttcaacat aaaatttgat ttagatacat      8160
gtgccatgga acacaacact aaagtgaaaa actttatcac cccagaacaa aacacgctaa      8220
cagcagattg gcaagggcgt tactgttgga tgaatccgcc ttatagtaac ccgttgccct      8280
ttgtcttacg tgctatttcg caaagcgtgt tacataacaa aacggtggtg atgttgctta      8340
atgtggacga tcaacaaaaa tggttcgata tgtgtgtgcg taatgcaaaa gaatcgtgt      8400 atatcaccaa ttctcgtatt cctttcatca ataacgaaac aggcgaggaa actgaccaaa      8460
acaataaacc gcaaatgctg gtgctatttg agccaaaagc accttacggc agtttgaaat      8520
cgtcttatgt gtcgttgcat gaaatgaaag aaaaagagat gttgcaataa ttttttaaaa      8580
```

```
aagtggttat tatacctata aaatagttgt tttattttt taagtgggta taataaccac   8640
cattgaaagg caagagggag aaacagtgga tagcaaaaca gcaataaaaa tgatagaaga   8700
ggacggttgg tatttagata gagttaaagg tagtcatcat caatacaaac atcctacaaa   8760
aaagggaacg gtcacgattc cccacccaag gaaagacttg gggcatttag aaaaaagcat   8820
taaaaaacaa gcggggctgt aaagcccccc ttataagaat aggagaaaaa atgttatacc   8880
cgatttgtat cgaaaaagta atgatggtt atgtggtatc tgtgccagat gtgccaggct   8940
gttttttctgc tggggatacc ttatcagaag cgatgttaaa cgcaaaagaa gcaatctctt   9000
ttcacattga agggatgtta aagatgatg aagaattgcc taaatctaac ccaatagaac   9060
aatatattaa tcagcccgaa tataaagatt ttattgtcac tgttgttgat gtagatttaa   9120
ctcatttaat gggtaaggca gaaaaaatta atattacggt tccagcgtta ttactgcacc   9180
gcattgatca gtttattgcc acccatccag aatataagaa tagaagtaac ttttttgtctc   9240
aactagcaac aaatagatta cttctgcat aataaaagcc gctatttcta gcggcttttt   9300
attcatctaa tatcttcctt aaattagttt tttcttcttc tgaaagtttg cttaaaacta   9360
gttcaagtaa tttatcttta gttaatttgc tacttcgtgt tgtgtggcta aattccatat   9420
tcatgacaaa tctgtgaccg cacaggggggt tttacacgc acaataatat cttgtaaatt   9480
cactgtgtat ccgttcagat ctttcgatta ctgatttcgc attgcaaaca gcgcagtaaa   9540
tatctgttgt tcttgccatt ttccccaaag ccatcacaaa ataactgca aataattata   9600
tcaatgaatg gcttttgta caggttaaaa acaaaaatta ttttgcgaaa ttttgttcgc   9660
ggaacttaat ttttaataag ttttgattt ctggatcttg atttattgtt ctgcaataa   9720
tctcttgtaa tggcattact tcatcatagt gatacacttc acgatatttc aacggatcgc   9780
caagcccgcc cgtatttgtc ggaataatac cacttaaacc tgcagggaat cggtgtgcgg   9840
ttagcacatc ttgtgcagag atgttttga tattcgcaaa ttcatctttt gtcccagtgt   9900
cgccaatagg aatcactttt aacccgtcag gatgaccgtt cgcaatattc acaaacatgg   9960
aacgaaagtt tccaactccc ttagattcac tgatctttct tgcgatctct tcttccattt  10020
cttcggttaa gtcgggatct gtggagtaca aaataaagcc catatgcgca ccattgctaa  10080
aatagcgacg gcgaaatact gtcgcatcag aatttagcaa tgctgattga ataccgccta  10140
cataatcggg cgatccataa acttgttgca tagggtcgta aagtttaata aagataatat  10200
ctttcgcatc atagcgatag atttcttgtg cggtatcata aagcgatttt ttcattaaat  10260
aagaatagcc gccatcttta cgcacgcgta aataaaggct agataacggc acaagacgca  10320
ccacttgccc aaacccatta cgcacttttta aagccccac atcaccaaac tgaattaagt  10380
taaggcaaag tgcacgcata tccatacgag ataatgcttt gccgccttcg tagagggagc  10440
tcaccatatt ggcacgacta tgcagaattc cgccgtgttg tgcgttttgg tgtggtagtt  10500
ttgccagtgc atggcgattt actggtggta aatagcaatt gtaattttca tcaaagccta  10560
tgccgacata atctagtgca ggcgaggcac tgatttcatt taatgaaaaa gtgcggtcat  10620
taattggggc aataacaatc ccttttttat tgtctgtttt tacattagtt ttcatttagt  10680
acgctccatc cgcgacgttt gcgaggttta tcacttaagg attttttatt aatggcgtta  10740
caaatggcaa aaaacacatc ggcgtgctgt gttttcacag tgccgttcagc cgtaaatgtc  10800
atcgtattgc cacttttggt tgattggtgc ttaatcatta aaaagctcgg tacaatatct  10860
aattcgcttt cgctccactc aatttgccca tgctcaacca aatcatgtac tttcagcacc  10920
```

```
atacccgtct tactttctgg gttgtaaata atggcagtgg cggcacggcg tgcaaactct   10980
ttcaccaact cataaacccc atagcccacg cctgtggcat caatgccgat gtaagtcata   11040
ttgtatttt  cataaagggc acgaatttga ttggcttgat agacatagga aagtccattc   11100
cattgataac gtgcaagcac gcgatatttc tcactgggta aggctggcgg agcaataatc   11160
acaaaacttg ccccatcgcc actgtgtgcg gggtcgaatc cgccccaaac ttcacgatca   11220
ccaaagggc  gatccgcttt cgggttaaag tcttccatt  tcgaaatatc tacaccacat   11280
tttaaaagtt gatgaacggt gaaaatagaa tccgcatcat caatccaaac gcacatataa   11340
agctgattaa acgcatattt gctatagcgt tgtttcagtt tttcaatgtt aaataacgtg   11400
cccgcaccgc cttttagtgc gtcttcaatg gttaccacat aacgccactg accatctgga   11460
caaagtcgcc caccgtcacg caattctgca aaagttggga atggcacgtt tttgcgttta   11520
gggtcgccat ctcgccagtt atcgccactc cagaacgaat aagattcgtg gaattttgaa   11580
gacggtgtgc tgaaataggt ttcgcgccat ttcgcgtgtg ttgccatcgc agaagccaca   11640
tcattgaatc gttggaaatc tcgaatccat gcgtattcgt caccatacac atggccactg   11700
ttaccttgtg acgtgttttt gttggtcgat aaaaaatgca gttccgcgcc attgcttaaa   11760
ataatcgggt tgccagtcag ctcaacaccg aaatattccc tcgccatctt cacaatgtaa   11820
ttttaaaga  tttctgcttg ccgtttactg gcggataaga aaatttgatt gtcaccgctg   11880
aaaattgcat cttccaacgc ttcaaaacta aaataatagg tcgccccaat ttggcgcgat   11940
ttcagaatat gcgcacatc  gtggtgcttg ttagcgcgga tgtgtttttg ataatcaaat   12000
aacgaatcaa taaacggctg gcacatttcg ggcgagacgt gggaaatatc attttttacc   12060
cgcttttct  tttatgttc  gtcaccatcg ccactatcgg caaaggaacg atcactgctg   12120
gaaacatcgg cagaattgac cgcgcttttt gctgtcactt tagctaccgt tgcggcacgt   12180
tgctttttat actgaatatc tttatcgatc agggcttcaa gttctttgat ttcttgatca   12240
cttttgtttt cacgttctgt cagcgtaata atgcgtaacg caattaattc ttcaatcccg   12300
ctttcgctga ttaaattgcg ccagttgtat ttttccgccc aatagtaaat cgggcgtgtg   12360
ctatttaaac ctaattcttc agcgatctct ttcggcgtgt attttttaa  atataaaaac   12420
tttgccgcat aaatcacttc gtcatcgtag cgttttgttt ttcttttct  tagcttagat   12480
tccgtcattt tttatcttgc tgttgttttg tggatgtatt gtggcaacaa aaaccgcaaa   12540
aatttaatgg caagatttgg atatcttcgg atatagcacg ttatccgtct atatccgaag   12600
atatccaaat tttgcccagt gattttgtaa aaaagatcgg caaaaatgac cgcacttaag   12660
caaacaaagc gaaaacgcag gcattttaa  aatgaataaa tcaaaactaa aaactgattt   12720
tatttgtatc gctacatcgg gctacaccgt ggacggccgc caaatcaccg cccaagaatt   12780
gcacgaaatg gcagaaacct acgatcccga acactacact gcgaatctat ggccagaaca   12840
tcgtcgttgg ttcaatatgg acaagtgat  cgagctgaaa accgaagaaa acgaaaaagg   12900
cgaaactcaa cttttttgcca tcatcgcacc caataaagaa ttaatcgaat acaaccgtgc   12960
aggacaatac ttattcacca gtattgaaat taccccgaat ttccgcaaca gcggaaaagc   13020
ctacttatca ggtttaggtg taacagattc cccagcatcc ataggtacta cagaattaaa   13080
attttcaat  gttgaacaaa aaggcagtgt ttgcggtgaa tttatcaaag tagatttttc   13140
tgcaaaagaa gatgttgaag aagataaggc attacgcacc ttagcgaatg cttttaaaaa   13200
gttattttca tcttccaccc aaacggaaga acaactaact cccaataaca acaataataa   13260
agaggacgat gcaatgaacg ataaacagtt cgagcaacta attgaggcgg tgaatggttt   13320
```

```
aggcgcaaaa attgacaatc atttttcagc caaagtagaa accaaagaac caaaaaacaa   13380
accagaagaa aagaaagatg aacagccgca aagcgtaaca gcagagcagt tcaatcaact   13440
tttaacaacg gttcaggcgt tggataaaaa attcaacgaa ttaagccaag aacaaaccac   13500
tgtgccaagc ggtgtaccaa cagtagaaaa cgaaaatgtt tatagcttaa acggttacaa   13560
catcgactta tcaaaaggat tctaacaatg aataaacaag cgtattacgc cctagcggca   13620
gcattagcga aacactttaa tcaacctctt gattcagtgt tgcgtggaga agttttgca    13680 cttaaagcac ctgaagcagc attattgggc gaaaacattc aacagcgttc tgatttcttg   13740
aaaggaatta acatggtgca agttgcgcat actaaaggta ctaaattatt cggtgcaacc   13800
gaaaaaggcg taaccggtcg taaacaaaca ggccgaaacc ttgcaacatt agatcactct   13860
caaaacgggt atgagttatc cgaaaccgat agcggcattt tagtgaattg gtcgttattt   13920
gattcattcg caattttcaa agaccgtctt gtagaacttt acagcgaata tttccaaaac   13980
caagttgccc ttgatatttt gcaaattggc tggaatggtc aaagcgtggc gactaacact   14040
acaaaaacgg atttatcaga tgtgaataaa ggctggttga aacttttaca agaacaacgt   14100
gcagccaact ttatgaccga atctacaaaa tcctcaggca aaattaccat ttttggtgat   14160
aacgccgatt acgcgaatct tgatgattta gcctttgact aaaacaagg cttagatttc    14220 cgtcatcaaa accgtaatga cttagtcttc cttgttggtg cagacttagt cagcaaagaa   14280
acgaaactca ttcagcaaaa acatggctta accctacgg aaaaagctgc attaggttca    14340
cataacttaa tgggctcatt cggtggaatg aatgccatta ccccaccaaa cttcccagca   14400
cgtgctgcag cagtgacaac ccttaaaaat ttaagtgtgt acaccgaggc tgaaagtgta   14460
cgtcgctctt tacgtaacga tgaagataaa aaaggtttgg tgacatctta ctaccgacaa   14520
gaaggctatg ttgtggaaga tttaggttta atgactgcaa tcgaccacac caaagtgaaa   14580
ttaaacggcg aagtatagga attaacaata aatgggaatg cgagattttc aacgccaaat   14640
gcaggcacta gcagaaatta atcaagtatc agagagcatt acacaacaaa gtgcggttgc   14700
gactcacggt aatgattatg ccgtgcttga atcgcctta caaatgatg tgaacgcagt     14760 acgcgcattc tcgacacgtg ccgaaaaatt agattacaag cgtgaccgct ttttgccgaa   14820
gtggttgccc tttgtgaatg aatatttaga taaaggggca atttatcaga atgattactt   14880
ggtttattgc attgtgtatt tgtttgacat tgctgatttt gaccgagcct tgtcactggc   14940 tgaaaagca attgagcaaa atcaatctat gccgcaaggg tggcaaacca cattgccaaa    15000
ctttgtcgca gaccaaattt acaactggac cgataaaacc gcctcagcag gtcaatccgt   15060
ggagccatat ttttcacaaa cttttaaaaa cgtggcgacc cagtggaagt tgcacgaaat   15120
tgtcacggcg aagtggctca aattagcggc ggcactgctt ttacgcagtc cacaaggcaa   15180
agtacaagcc agtggtattg atgatgccga aacacttgtg ctggctatcc aattgtgtaa   15240
ccgcactttc caactcaatc agaaagcggg tgtaaaaaat atgattgagc gttgtgtcat   15300
gcgtttaaac gcattggcaa aatcgggtaa atatgaccca acaagtcttc cccaagtggc   15360
aggcttgagt ttggaatcaa gtcaaattaa ttttgatctt gtgataaaaa aactcactgc   15420
ctgcccactc caaacagcg aggaaggcaa tgtttaacgg cagaacgcaa gattacgacg    15480
ataccgtcat cacaaataac ggcttttggt cggatattta tgttgaagag tttcaaaagc   15540
aacgcgccat tccattacaa attcctgtgg aaatggtgaa aacggcactc attgccgcca   15600
tgcaaggcgt taatttagat cttgccgaag ttgaagaaaa tcaccgtaaa agtgcggtca   15660
```

```
attctgtgca agaaatttca acacagcgga ttaatggcga aaactacgct gaaacccttt   15720
ataaaaaagc ggtctttgcc cgagcaaaag cggaactatt acccgaattt aacacccttt   15780
cagggcgtga gattcatcaa aatcgtgatt acgtggtcga gcaaaaaagc ctattggcag   15840
aggcaaccca cgctatccgc acattgaaag gtaaaaaacg gggatcggta tggctgctgt   15900
aaagaaaatg ctgtatcagc aactcactga ttttttgctc accaaattgc cgaaacgcta   15960
ccacggcaat ttttatagtt ggatggaaaa cggaaagctg gtgaaccaag gcaagcaagt   16020
gaccaataat gggatcgaaa tttgtcatat tcaatgtgac ggtattctgt tttttaacga   16080
atttcctttt aaggaaatat caccggctta cttaatggca ttaattcaaa tttggctcaa   16140
tgaaaatgac gatatgcgcg attgtctcga caattacgaa acgccctttg acattgaaat   16200
tattaatgat gatgtggctg atatgagttt taccattagt tttcaagagc cattaaccgc   16260
cattgaagac aaaaacggcg aattggacat tgataacaag aaatatagct tatcgactat   16320
tgatgtttgg atcgcaaaag aaatagaact tgaggcgata gtagatgcaa attaggctcg   16380
gattaaagca agaagattta gatgcctttg ttagagattt acgtacatta aacttaaccg   16440
gaaaacaaaa gaaaaaaatt cttacctgga cattaggtgc aataaagcgt aaatctcaaa   16500
aaaacatcag agaacaacac tcaccagatg gaacagcctg ggaaaagcgc aagcccgtag   16560
atggtgaaat caaaaataaa cgattgttaa aaaaagttct tcgttatgct tcaattcttg   16620
cagaagaacg aggaaaaggg cgaatttact ataagaatcc attaacaggt gaaatcgcac   16680
aaaaacaaca agacggattt acagagcatt ttagagtttt tgcaacggac aaaaacaaaa   16740
atggttcagg caatgaccgt gccacaatta gacaagccca aaaattaaga tcattggggt   16800
atagaaaacg taacgggaaa aatagacagg gaaaaacaaa ataccggctt ataccatta   16860 aagaaattcg tgaaagatta acgaggacat gggcgagtat ggagatccgc cgcttagaaa   16920
ataaagtgaa tgcaggcaac ggaaaaacaa actgggaaat tcatgtacca gcaagaccat   16980
tcttagatac aagagaaaaa gaaaacgtag atattctacg agaaattaca ctgaagtttt   17040
tatcaggtga atacaaataa aaaataaccc cgaatcacgg caatgattcg aggttgtaaa   17100 cccccttacaa accattaacc aataaggagt taattaatat gaatgattat attcaattta   17160
tccaactaat caaggagatt tccacgatga acaacgctta tttactcttt gcattattac   17220
tgattgctat tgcagtgtgg cgttcgcctg aaattatccg tgcttggatt gaatacaaga   17280
agttttctaa aaaataaatt ttttatcaca accataagag acagtaacg aatgttccca   17340 tctgtacaaa ttaacgccct taatcagtta agtggcgaaa ccaaggaaat tgaacgccac   17400
gcattatttg ttggcgtagg caccactaat caaggaaagt tattggcatt aacgcccgat   17460
tctgattttg acaaagtatt tggcgaaacc gataccgact taaaaaaaca agtgcgtgcg   17520
gcaatgctta atgctgggca aaactggttc gcacacgtgt atatcgcaca agaagacggt   17580
tacgactttg tcgaatgtgt gaaaaaagcc aatcaaaccg cctctttga atattgtgtc   17640 aatactagat atttaggcgt agataaagca agtattggca aactgcaaga atgctatgca   17700
gaactacttg ctaaattcgg tcgtcgtacc ttctttatcc aagctgtaca aggtattaat   17760
catgatcaat ctgacggtga acatgggat caatatgtac agaaacttac cactttgcaa   17820
caaaccattg tcgccgacca cgtttgctta gtgcctttat tatttggcaa tgaaacaggc   17880
gtattggcag ggcgattagc aaatcgtgcc gtcaccgtgg cagacagccc agcacgggta   17940
caaacaggcg cgttagtgag cctaggcagt gccaataaac cactggataa agacagaaac   18000
gagcttactc ttgcgcattt aaaatccctt gaaaccgcgc gttattctgt gccgatgtgg   18060
```

```
taccccgatt atgacggcta ttactgggca gacggtcgca cgttagatgt agaagggggc   18120
gattatcaag tgattgagaa cctgcgtgta gtggataaag tggcgcgtaa agtgcgttta   18180
ttagcgattg ggaaaattgc agatcgttct tttaactcca caacatcaag cacggaatat   18240
cacaaaaatt atttcgccaa accgcttcgt gatatgagca aatccgcaac catcaacggc   18300
aaggatttcc caggcgaatg tatgccaccg aaagatgatg ccatcacgat tgtatggcaa   18360
agcaaaacca aggtaaccat ttacatcaag gttcgccctt acgattgccc gaaagagatt   18420
acggcaaata ttttcttaga tttagacagc ttaggagagt aaacaatgga acgtattagt   18480
ggaatgagtt ttgacttcta tttattcggg ttgcctattc atgcagagtc tatcagttta   18540
tccattacag ataatagtac cgttgtacaa acacgtggaa ttccagatgg ttgggtaagc   18600
ggtgatgtgg cagcagaagg cgaaattgaa ttagatgcaa aaaatttctc aaaattatca   18660
gctgcagccg ccgcagcagg aagttatcgc agtttacccg aaacggattt taccttcttt   18720
gcacaacgtg gtgggattcg cgacaaagtg gaaacctttg gcaataagat tattttaacg   18780
gatgtgttaa atatcgatcc gaagggcggg gctaaatcca tgaaaaaact aaaatatttt   18840
gtgacaagcc cagattttgt acgtattaac ggggtatcgt atttatctga tgaagataca   18900
cgcgatcttc tcggctaagc gaatttaggg gctgactgtg ctgacgtata acaataataa   18960
acaagcaagt gcggtcagtt tcctaaatgt tttaaggaaa tttatgaat  agcaaaatag   19020 atagcacaat tccgtttatt ggctcactca ctgcgcttat ttcaggatat agcttgcatg   19080
aatgggcatc attattcggt attttatttg gtgcggtttc agtgtggatc gcttaccgaa   19140
aatacaaaga agacgtacaa gcacgcaaag atgaattagc ctacaaaatg ttggtagcaa   19200
aaattgaagc aaaaaaatta gggatagcaa tagatgagta aaaaatttgg tgcaatgatt   19260
ttatgttcag ccgcagctgt cgcagccgct tttttgccc  agcagaaagg cttaccaacg   19320
caacaacaaa atcaaattag cccaaaagcg gtgtcaatga ttgtgaattt agaaggttgc   19380
gtgcgtaatc cgtacaaatg ccctgctgat gtgtggacaa atggagttgg aaacacctat   19440
aacgtagata aaaccaaaat tttaaccatt gatgaagtag caaccgattt acgccaaaac   19500
atcaaagagg ctgaaaattg cattaatgcc gattttaacg gcagaaagat gaatcaagat   19560
caatatgatg caatgacctc actcgccttt aatgtgggct gtggcaacat caaaacctat   19620
tacagcaaaa cccaaggtaa acgtgtcgca accacgattt atcgcgcagc acaagcggaa   19680
aactggatat taatgtgtaa tcgtattgaa gattttaaca aatcaggcgg acgtgtgcta   19740
aaaggcttac aaaaccgcag agcaaaagaa aaagccctat gtttggggga ataatggaat   19800
ttaaagcctt atttatcggt gtattttga  tggtgtttgt gggttgtatt ggttctacct   19860
tgcactataa aaagcaagca gaaaccaccg cacttttact taaacaaagt gaacaaacca   19920
tcaaacaaaa taaagtgatg ttgcaacggt atgaaacaca aaatgcaaaa ttgacttctc   19980
aactcaacca agcaaacaaa aaagccgaac aacgcagcca acaactaaag gacgtgctaa   20040
acaatgcaga aaataaaaat tggacttatg ccgcgtgcc  taacgatgtt gctggcgtgc   20100
tcaaccaccg cacccaagcc aaataatatt cggttgattt gcccacaaac caccgaatgc   20160
agagcattaa gcgtgaatat tcgcactaac ggcgatttag cagagggttt aaatcaagcc   20220
ttagaccgct tggagatttg cactacggct tatgcggcta tcaataagtg catcaccgat   20280
ttcaacaacc aaaacagaaa ccaaaaggaa aactaaaaat ggaaaaaaca caagcgcaat   20340
cattgttaga aaaacttact ggaaatctta aagattccgt cacattaaat gttgcaggcg   20400
```

-continued

```
ttgattttac ctttattcga gataacgcgg cttacgatca aatgttaaat gacattgaaa    20460
gtaacaataa agtgacacct atcaaagatt atttactggc gattgttgcg cgcgaacaaa    20520
aagaggcatt gcttgaaatt attcacgtgc caacactggc ggcacagcta gcagcgaaag    20580
taaatgaagt gtttgtgcca gaaattcaaa ttaccgtaaa aaactaacgg agcgtgtggc    20640
aagtatcgag cgcaacgggt tatcacaagc cattgcgcta cgtatgcact atttaccaca    20700
cgccgataac agcgactaca acttagcacg cgcaatatgg ttacacaaac agtattttga    20760
acaacaggca aacgccgtcg caagcggtat cgccaaagtc ttttaggatt tcattatgtc    20820
agcagcacaa gggcttgaat atatcatcag cttaacagac caactttcag caccgttgaa    20880
aggggtcatg aagtctattg atgatttggg caaacgtggc gaagcagcaa tgaaaaaaat    20940
cgggctgggt gtggcaggta ttgtcggtgc aggctttgcc ttaaaaagtg cgctagatcc    21000
cgccattgag ttaaatcgcg ccataggcga agttcgctcc cttggggttg ccgatgatgc    21060
gttagagaaa ctaagcaaaa ctgcccttaa ttttccagt caatatggcg aaagtgcggt    21120
gaattttgtg cgatcttctt acgatattca atcagcgatt gcagggctaa atggtaacga    21180
attagccgaa tttacccaaa catcaaattt attagccaag ggcacaaaag ccagcgcagc    21240
gaccattacc aattatatgg gcacaatgta cggtattttt gctgaagatg ccgccaaact    21300
aggaaatgca aattgggtaa ataaaattgc agggcagact gcccttgcgg tgaaaatgtt    21360
taaaacctca ggcgatggaa tgagtgcggc atttacctcg ttaggcgcag ccgcaaaagc    21420
cgcaaaaatt gatgtagcag agcaatttgg cgtgttaggt aacttacaag ccacaatgag    21480
cggaagcgaa gcagggacaa aatacaaagc ctttttagct ggcgtgagtg gtgcgcaaaa    21540
agaattaggc ttaagttttg ttgataccaa tggcgatatg ctagatatgg taaccattct    21600
taacaaaatt aaaggtaaat ttggcgatac cttagatgtc gcacaagcag caaaactgaa    21660
aaaagccttt ggcagtgatc aagcggtcga tttaattaaa ttactcttgc cgaaaacgaa    21720
agaattaaaa aataacatcg ccgctattac aaaagtcagc gacacaaaag ccttggcaca    21780
aatggctcgt tcaatggttg atccttggtc gcgccttagt caaattataa cgggtgtcaa    21840
aacggcaatt gggggcgaaa tattgaaaaa acttgatcct attatgcaca aggtggcaga    21900
tctaggacaa aaatttattg attggctcaa aacctataaa aatattgcac gctggattgg    21960
ttatgtaatg ggattactaa ttggatctgc gggagttgct gcagctatca cattatttag    22020
tgggttaatt ggtgtaatta aaattttagg tatctcattg ttcacaattt tggcacctat    22080
tcttattttt accgctaaaa ttattttgt agtagctatt gtttataaat ttcgtacaaa    22140
aattcttcaa tttattgatt catttgtaca aggttttaaa ttagctggcg tatcagttga    22200 accacttttta aatgctattt atttaatttg gggagcattt aaaaaattcg gctcggcagt    22260
tatcaaatta tttgatttat ttccagattc atttcaaaca atattgacat tcaggatat    22320 cgcaacagtg gctggctttg ctgtgggaat ggtatttaat ggaattgttg ccgttattga    22380
attaattgca cggcaaattg aagcggtagc gactattttt agcaatgtcg ccgatgtcat    22440
tatcgccact tggcataatg tcattgatga ttgggaaagc aaaagtgcgt gggatatatt    22500
caaaggctta gcgacaggaa ttggtcaaat ttttacaacg attttaaaag ggattaaaga    22560
tcaatttatc aatacgatta attggattat tgataaagtc aatatagtca gtgggaaaat    22620
tggctttgaa ttacctaaaa ttccgaatac ttggttaagt gatgatgcac aggtaacaac    22680
agtaaccgct gcgtcaaata tctcaagttt aggattaaac gctgcagtag ataatacatc    22740
ctggagaaaa tccccaagta ttgatttacc aaatagccta aaaccacaat taaattcaat    22800
```

```
gcctcaagga tctgtaacaa aaacattgac acaaaaccgc acagaacaac gcaccgtaaa    22860
ctatggtggt gtcactatca atagtaacaa cagtgaagaa atttggcaga aattgcgcaa    22920
taaagaacag ttagcagcag ggtgataaat ggaaaaactt taccttgatt tactgattac    22980
gggcgaaaac attacgctag atagcggcaa tcagccgtta atttgcgata accgaatatc    23040
tattgcgcaa gatattaaac acgccatttt agaaagtgga ttggcgacac aacttatcgc    23100
agagcgttcg cgcattttac gccgcgatat tattttgcaa atggtgttat tggttgaaga    23160
agatgtgcgc ttgattccag gtactgtttc cattagcgaa gaacgtttag ggcagttatt    23220
tattaccgct gaaacttatg aatttgggcg acttgatgaa ttggagttac gtttaaatga    23280
gtgaaaattt taaacaaatg ttagctgaaa gtggattgcc cacagaagaa acgcaaatcc    23340
gacaagaatt tgaacgctta accgaaaaag aagggttaat cactaataca agccgaatga    23400
gtccattctg gcgattaatc actgctattg cggttaagcc tgtgaagtgg ctgacagatc    23460
atttaattgc tgaaattctg ccgaatttat ttgtaaaaac ggcaaaagac agttggttac    23520
aaattcaagc ctgggcagtg ggcttagatt ttaaagccgc aacaaaagca gaaggcgtcg    23580
tgcattttac aaaagaaagc gatgtaaccg atctgacaat taaagcgggc acagtgattc    23640
agacagagcg tattaatgat gtgattttcc gtttgattgt cacgcaagaa accattattc    23700
ctcaaggtgt gttgcgtgcg cctgtgccag taatcgcaga gcaggctggc gcaaatttca    23760
atttggctgc aggttattac cgtatttttgc cagaatctat cgcaggggta agtgcggtag    23820
aaaatttaga agattggcta acatcgccag gtgctgacag agaaactaac gacgaattac    23880
gagaacgtta tcgcacgcaa ttttcgagtg ttgggcaaca ccatattgac agtgtttaca    23940
aaggcatgat tgcgaaagtc gccgccttat cggtggacag aatttatttt aaacacgatg    24000
caccacgtgg gccaggtaca gcaaacgctt atttgttatt ggacacgggt gtaaccagtc    24060
agccgtttat tgataaagtc aatcgccatg tacgtgacga gggttttcat ggacacggtg    24120
acgatttaat ttgctacgcc atgccagaaa ctaaacacaa tttaacgtgc gccatttact    24180
tccagccatc tattttttgtc ggcgatgtgc gtaaacaaga aatcgtgcaa caagtggaaa    24240
atatgatccg ctgcgcattt cgcgaaaata taattatgg cgtaacaagg acttacccctt    24300 ttagccgttt tagttggtcg aaattgggcg aggaaattca cgacaacatc agcgaaattg    24360
catctatcgt atgggggcaa atcgacattc aaagcgagtt atctattcca cgcattcagc    24420
aattatccgt cacagtccaa aagtaagggg caaaaatgaa aataaaattg ccctttttgga    24480 tggataaagg cgaattaagc aaaatcgctg tgctattcgg aaaatggtgg gattatgtgt    24540
taagtgcggt caaatttccc ttcaatattt tagatgaaga acactgcagt gaacgcattt    24600
taaatttaat cgcctatcaa cgcgacgtag aacgatttga gggagagccg ttagagctat    24660
tccgcaagcg cgtgaaatat gcctttttaa atgcgaaaga tgctggcagt aaagcgggct    24720
ttatccgcat tttttgaacgc cttggcattg gctatgtaga aattgaagaa cggttcgata    24780
gggaaaattg ggatgtgatc aaaattcgaa tcagtgattc acaattagca agaaaaacag    24840
aattactcaa tttaatcatt cgaaaatatg gccgcacttg tcggcgttat acctttgaag    24900
tgatcactaa agaaaccgta agtatttatc acggcgaatt taaccatgat caccaaagtt    24960
tttatgtgaa agtaaacgga taataacaat aataagaggt ttatttatgg ctagtttaat    25020
tacgccacaa tttgaacgct acgttgcaga acaaactatt gcacgtggca cagtacagtt    25080
tgatgaattt attttttgcca acatcccagg tttaaatgag aacaatcttg cgcaatatct    25140
```

```
cactatgccg acatcggcac aaattgtaca tcgccaagcc gtatcgcaaa gtggcgtgat   25200
taatgaaaat gccgttgtgt attctgtgac gattggtact gaagtcggcg attttgattt   25260
caattttatt ggtttgatta atcgttctaa aaatctttta gctgttgcgg tgcaaaccga   25320
tacagtgaaa aaaatccgaa ataaaaatgc tgtgcaaggc aacagtatta cgcgcaatat   25380
gcttttagaa tttagtggcg caaaagctct aacgggcatt aatgtcaatg cgaacacttg   25440
gcaaattgat tttactgtgc gactacatgg acttgatgaa aaaattcgtt taaccaatcg   25500
tgatctgtat ggcagagcag tattttttcga tgatagtttt ctggttaaac gtaaaacagg   25560
caatcaattt acgattcaac caggcacggc ttatgttgaa ggcgttcgta tggatttatc   25620
cgcactttat aacctcacag caaacaattt gccatgttca gtttatgccg atctagtaca   25680
tcattgcacc gtaacgggag aataccaaac cgaaattaag tatctcaccc aatcaaaagc   25740
agattatgta gatactgcaa accgccaaca ttatgtacaa attctggcgg atattgatag   25800
ccaaggcaat gtgacagatc gccgcttgct ttcgccgttt ttaggcatga atccgctcac   25860
attagatgac acaaccgaaa cacccaaga taaatggggt catacgcaca agttaccaat   25920
tgccagcatc acaaaaaaag gcattgtgca actaagctca gctactaaca gcaacagcga   25980
aaccgaagct gcaacatcaa aagccgtgaa aaccgcctat gacaaagcag tagaagccaa   26040
aactacggcg gacggtaaag tggggttaag tggcaatgaa gaaatagcgg gggataaatt   26100
attccgtagc cagactaaat tccaaaatgg cgtgttgatt tctgcaaata aaggacactg   26160
ggataatggg tataaagtct atattggtgc agattctgat aatgcacatc tggtatttgg   26220
cgatgataca ttgagattac acggctcaaa tcatcgtatt tcgtataata attatcatct   26280
tttccatgag ggctacaaac ctcgttttaa cgaacatatt ataaacaaac ctaatacact   26340
tgcaggctat ggtattggga atttttaaagt agaacaaggg cagggcgatg ccaatggcta   26400
taaaaccgat ggcaattatt acttagcaag cggtcaaaat ctaccccgaaa atggggcatg   26460 gcatattgaa gtagttagcg gtggggcaac aaatgcggtg cgtcaaattg cacgtaaagc   26520
aaatgataac aaaatcaaaa cacgcttttt taatggctca aattggtcag aatggaaaga   26580
gacaggcggc gacggcgtgc ctattggtgc ggtggtgtca tttcctcgtg cggtaactaa   26640
tcccgttggt tttttaaaag ccgatggcac gacatttaac caacaaaccct ttcccgattt   26700 ataccgcact ttgggcgaca gcaaccaact tcctgattta actcgtagcg acacaggcat   26760
gacggcttat tttgccgtgg ataacattcc tgcaggctgg attgcctttg attcaatcag   26820
aacaaccgtt acacagcaaa attaccccga gttatatcgt cacttagtcg gtaaatatgg   26880 ttctcttttca aatgtgccat tagctgaaga ccgattatt agaaatgcat caaacaattt   26940
atcggttggt gaaacgcaaa gtgacgagat taaaaagcac gttcacaaag tgagaacaca   27000
ctgggttaat tcaagtgata gtaatatttt ttatgacaaa acgaaaacag ttatagattc   27060
acgattacgc actgcaacta caactgatga taatctcagt gataatggat ttatgcatcc   27120
gctattagat agcccaatgg caacaggtgg aaatgaaact cgccctaaat cattaatcct   27180
caaattatgc atcaaagcca ttaacagcct tgatgacgtg caattctggg tgaaggcttt   27240
cggtgttgtt gaaaatgcag gggtgcttga tgcgggtaca cttgcgcaaa atatgcaaag   27300
tgttgaacaa aaaatagaag agaataaaca atcaactttg cgagaaatca ccaatgcaaa   27360
agctgatata aatcagcaat ttttgcaggc acaaaagaat ttatctcaaa ttggcacatt   27420
aaaaaaagtc tgggaaggta gcgtgagtac tgggtcaatt actatatcag agagttgcta   27480
tggcaaaacg ttaattttttt atattcagac agcagatgat caaagtaatt acggtgattc   27540
```

```
cattgaaata gtcagttttg aagcgggtgc agaagatgaa ggcggaggtc gtttgactag    27600
tattcgtgaa atagtatcca aatataatta tcgccaagta gtacccaaag agttcactgt    27660
gtatattgct ggtgacggta aaactataac cattggccaa cttgatgcac gttctataaa    27720
acgtatttat attcgataaa ggagcgttaa atgaaagtct atttttttaaa agaaaatttg    27780 aatagttatc aaattttccc tattccgcaa aacttaaatg attttgtgga aatggaagta    27840
gaaaacgaat cagagcttga gactaaacaa cttatttatt ttaaaagtca atacattcta    27900
gttgatagac aaccaacaga attacacaaa tggaacggaa acagctggat tgtcgatgaa    27960 aaaagaaaa ctgaaattaa gcgtaaactc attaaaaatc tagttgatag cattgatgat    28020
acagcggcta acattagtgc aagatggaca aggtttgccg aagagtataa ggagcgagaa    28080
gctgccgcta ttgcctttaa agaagcaaat tttactggcg aagtaagcat ctatatatca    28140
agttttgcaa ctgtcgcagg acttgataat aaatcagcaa cattgctaat tttaaaacag    28200
gctgaaggat tacgaacact gcaagaacaa ctcgcggtgc agcgtatgcg taagtatgag    28260
ctcaagcacg aagaattgag tgaagaagaa ttacagcaaa ttcataatga cattatcaga    28320
aaaatgaaag cattagcgga ggctcaacaa tatccagaag gttttaaaac taatgaattt    28380
taggtgatgt ttaatatgtg gaaacaacaa aaactaaaat tatccccaca ggcaaaaaca    28440
acattacaaa acgcacaaaa ggggattatt tccccttttt cgctatctgt aagtggtact    28500
aaattaggtg tgcataattg gtcgcacggc atcaaagaaa aatcaaatca ctatttgtca    28560
cccgaaaatg ccgtgaaagc actggcggca aagttggtcg attatgccga tccgaatcgc    28620
cctaaaggtg tgcaggatgt tgtggtcatt atggtgacaa gtagcaatat tgatcagttt    28680
attgcagagt tggaaaaagt gcgtgagcta ttgccagagc caacatttaa gcaagcacta    28740
gactatgcga aatcaagtaa agatttacaa gaaacaaaaa tgataaaaac gccaactatg    28800
gcaagtccat cattttccaa tagtgccgat attacgccag gttccgcccg cacaatgcaa    28860
agtattttac gtaatgccac atccgcagcg gttgcggcac aaactaaaga tccgatggcg    28920
atgattgagg cgttaaaggc agccaaaaaa gaacgcgaca agcgaataa cgaaaaagtt    28980 gaaaaaatgt tgaatacatc ggctaatatc tatgcttttg ttgtttcaga ttatcttgaa    29040
atcgcagaaa gtaaaatgaa agtgaatgtg ccaaagtcaa gcaatatatt taccacttgc    29100
gttatgttta ttggcgcaga tttaaccaat attagaggaa tgttgcaaaa tgcagaaacg    29160
taatcccagt gtacaacttg cactaaatgg cacgccaatt tatttaaaca atattttaat    29220
gtcggtttcg gtcaaacgtg aagaaaaaga catgagcggt caaaaatcaa gtaccaaaaa    29280
atcagataaa ggcgtaaaag ccaaagagtt aagcgtaacg gggtttattc catacaacag    29340
aaaagagtgg ctgacgcagc ttttcaattt agctgaggca gaaacgggta aaggcgagca    29400
aacaaaatat cgggtatctt gtactgtggc tgaagccgtg aatatgcgcg aagtgcaatt    29460
tagtggagag gtatccgcaa ctgagcaaaa tgggcagttg gggtggtcga tttcatttag    29520
gttgcgtgaa gtcaattccg ttgccgagaa aaaagaccag cgaaagaaaa aaccaaaggt    29580
aaaaactcaa ggtgagaacg caccagtagc aaaaagtgca ggtgaaaatt cggggaaatc    29640
tggagaagaa aacaagtcgg acgaaagaaa aggcttggca aaagatttag atgattggat    29700
tggttcataa atgaaaatta taaaaacatg cattattgat gatgaagaat tggaacttgc    29760
tgatgaactt atcgttttag aacttaataa tacggggcgt gggtttgtca cggttcgcac    29820
agataaagat tgtatcggca aaagtgcagt ttttgagatg gagaatatg agcactatta    29880
```

-continued

```
caaatggttt gacggtattg ttgagcgtga acaaagtgcg gaaaacggct ataaaaaatt    29940
attcattcgt gaaaaagtgg cagtatttga aaagccgtta aattgctctc atcgtcatat    30000
tactttgcgt gatttgtgtg cttggataac aagccaaaca aaaatccccg tcaaggtgcc    30060
gcaggcagat tatgcggata cgccgatttc gttgtttact cacaacggca gcggttatca    30120
gcttttagcc aatattgggc gacaatatca aatagcagat tatatgtggc aacaatcgcc    30180
agacggctct ttgtttgttg gttcgcataa agattcacgc tgggcaggta agaatattga    30240
atttgacgaa agcatgacat taacaagcgg cagcaatgat atgaccattc cgattactgc    30300
tgctattcga ccaggtgcga ttatcaatgg caataaaatt cagaaagtag aattgtctgg    30360
cgatgattat gtgctttcgt gggaaaattt aggcaaagat ggtaagccag aacaaaaaag    30420
cccagaacgc cgccaaatgg aaaaaacatt ccccgaactg gctggcggtt atcatttgcc    30480
gaagtatgct aaagttgttg gtatagcaga tccctcaagc ggcggcgata tttccgatcc    30540
gttccgacca aaatatgctg tcgagttgca actactggac gaaaacggaa acgaggataa    30600
aacggtgcca gtttacccag ctgtgccttt gcctgtaaca agtacaggtt cacaaggtgg    30660
ggattttgcc tttcctgaag tgggcacaat ggttgaagtc ggttttgctt atgggcgaag    30720
tgatcagcct tttgtacgca ctatgttagc acaaggaaaa acagtaccga gtgttgcacc    30780
tggagaacaa ctcaagcagc aacgccccga agtgtatgag cgcaccgatg ccgcaggcaa    30840
taagattcgc gaaaccgatc agaagattac agataaatcc tttgaacgac acatcgaaac    30900
agatagtgaa gtaaaacaaa ttggtacatc gacaaaaaca gtagattcag atagtacgca    30960
aactataggc ggaaataaaa ctgttagcgt attgggtagt atcaatgaca cgactgcaag    31020
caatcgtact gtgggaactg gtggcacgtt acaagaaaaa atcgtgggac tagcgcaacg    31080
tgtttcggac gaaaagaata aatttgtggc accgctaagt tatataggaa cagaaagtca    31140
gaatattttt agattgttag aggacactat tcagctatta ggcgaagttg cgagtgcagt    31200
ggcaacgcat acgcatagag gatcgccacc gccagatcaa gcaagcacat tcaaccagca    31260
ggcaaacaaa gcaaaaacaa tcaaaagtaa actcacgcct atcattgagt aacaaccgca    31320
attcatatca aaccaaagcc gcacaatgtt gcggcttttc tttatgtttc cgacatgtat    31380
gtcggaaaca tcagccacgg aaaatctaag ttattgttat aacaaataaa tctacgtaat    31440
aagcaatata aaacaattcc acggaaattt ttcacgtaaa aacacaaggc acggaaaatc    31500
cacttcct                                                            31508
```

```
<210> SEQ ID NO 4
<211> LENGTH: 32
<212> TYPE: DNA
<213> ORGANISM: Artificial Sequence
<220> FEATURE:
<223> OTHER INFORMATION: Synthetic

<400> SEQUENCE: 4
gagacggatc cgtttgcaca actacgggct ta                                   32

<210> SEQ ID NO 5
<211> LENGTH: 36
<212> TYPE: DNA
<213> ORGANISM: Artificial Sequence
<220> FEATURE:
<223> OTHER INFORMATION: Synthetic

<400> SEQUENCE: 5
gagaccgctc gagcggatgg cttgcggaag tttatg                               36
```

```
<210> SEQ ID NO 6
<211> LENGTH: 35
<212> TYPE: DNA
<213> ORGANISM: Artificial Sequence
<220> FEATURE:
<223> OTHER INFORMATION: Synthetic

<400> SEQUENCE: 6
gagaggaaga tctcccggtc aaaatctacc cgaaa                              35

<210> SEQ ID NO 7
<211> LENGTH: 34
<212> TYPE: DNA
<213> ORGANISM: Artificial Sequence
<220> FEATURE:
<223> OTHER INFORMATION: Synthetic

<400> SEQUENCE: 7
gagacggaat tccgctttag tttgctccgc aacc                               34

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
gctgctctac cgactgagct a                                             21

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
agacggtgag gcacgtttag                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10 aaggggggaaa taatggcaac                                              20

<210> SEQ ID NO 11
<211> LENGTH: 19
<212> TYPE: DNA
<213> ORGANISM: Artificial Sequence
<220> FEATURE:
<223> OTHER INFORMATION: Synthetic

<400> SEQUENCE: 11
aaaggattgt tattgcccc                                                19

<210> SEQ ID NO 12
<211> LENGTH: 242
<212> TYPE: DNA
<213> ORGANISM: Artificial Sequence
<220> FEATURE:
```

```
-continued

<223> OTHER INFORMATION: Synthetic

<400> SEQUENCE: 12
actagttatt gctccagttg ttagttttca cactttaaaa aaggctttca attataaaat      60
ctttctccat tattacgttt tttcacaact gtgatccacg ccacagttgc aaataatcaa     120
catagaaaaa ttaaataaca taattgatga aaagttagtt tttcacaaaa atacgaaaaa    180
tttcatcacc tagagaggaa ttccatatgg gaagagcggc gcgccgctct tcgtaaggat    240
cc                                                                    242
```